(12) United States Patent
Vetter et al.

(10) Patent No.: US 11,490,924 B2
(45) Date of Patent: *Nov. 8, 2022

(54) EXCISIONAL DEVICES AND METHODS

(71) Applicant: TRANSMED7, LLC, Portola Valley, CA (US)

(72) Inventors: James William Vetter, Portola Valley, CA (US); Eugene H Vetter, Portola Valley, CA (US)

(73) Assignee: Transmed7, LLC, Portola Valley, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 16/929,522

(22) Filed: Jul. 15, 2020

(65) Prior Publication Data

US 2021/0007767 A1 Jan. 14, 2021

Related U.S. Application Data

(63) Continuation of application No. 14/864,146, filed on Sep. 24, 2015, now Pat. No. 10,736,651.

(Continued)

(51) Int. Cl.
*A61B 17/3207* (2006.01)
*A61B 17/3205* (2006.01)
(Continued)

(52) U.S. Cl.
CPC ...... *A61B 17/3207* (2013.01); *A61B 10/0266* (2013.01); *A61B 17/3201* (2013.01); *A61B 17/3205* (2013.01); *A61B 10/06* (2013.01); *A61B 17/32053* (2013.01); *A61B 2010/0208* (2013.01); *A61B 2017/00685* (2013.01);
(Continued)

(58) Field of Classification Search
CPC ...... A61B 17/3207; A61B 2017/00778; A61B 2017/320064; A61B 10/0266; A61B 17/3201; A61B 17/3205; A61B 2017/32007; A61B 2017/320082; A61B 10/06; A61B 17/32053; A61B 2010/0208; A61B 2017/00685; A61B 2017/2903; A61B 2217/005
See application file for complete search history.

(56) References Cited

U.S. PATENT DOCUMENTS 5,100,424 A * 3/1992 Jang ............... A61B 17/320783
600/463
5,658,302 A * 8/1997 Wicherski ........ A61B 17/32075
606/159

(Continued)

*Primary Examiner* — Jing Rui Ou
(74) *Attorney, Agent, or Firm* — Young Law Firm, P.C.

(57) ABSTRACT

A platform device for material excision or removal from vascular structures for either handheld or stereotactic table use may comprise a work element or elements configured to selectively open and close at least one articulable beak or scoopula configured to penetrate and remove intra-vascular materials or obstructions, or follow a central lumen of another device or over a wire in a longitudinal direction. Flush and vacuum tissue transport mechanisms may be incorporated. A single tube or an inner sheath and an outer sheath which may be co-axially disposed relative to a work element may be configured to actuate a beak or beaks or scoopulas and provisions for simultaneous beak or scoopula closing under rotation may be incorporated.

9 Claims, 48 Drawing Sheets

Related U.S. Application Data

(60) Provisional application No. 62/063,848, filed on Oct. 14, 2014, provisional application No. 62/056,983, filed on Sep. 29, 2014.

(51) Int. Cl.
*A61B 17/32* (2006.01)
*A61B 10/02* (2006.01)
*A61B 17/3201* (2006.01)
A61B 17/00 (2006.01)
A61B 10/06 (2006.01)
A61B 17/29 (2006.01)

(52) U.S. Cl.
CPC ............ *A61B 2017/00778* (2013.01); *A61B 2017/2903* (2013.01); *A61B 2017/32007* (2017.08); *A61B 2017/320064* (2013.01); *A61B 2017/320082* (2017.08); *A61B 2217/005* (2013.01)

(56) References Cited

U.S. PATENT DOCUMENTS

2002/0010483 A1* 1/2002 Follmer ......... A61B 17/320783
606/159
2002/0103459 A1* 8/2002 Sparks ............... A61B 17/3207
600/585

\* cited by examiner

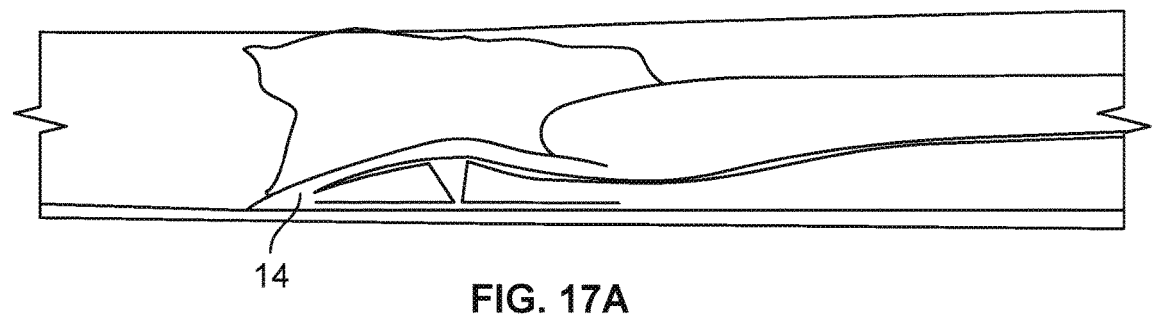
14  FIG. 17A
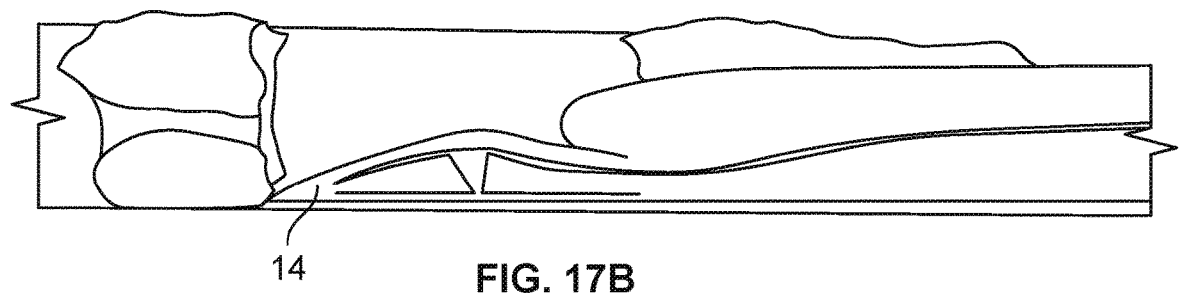
14  FIG. 17B
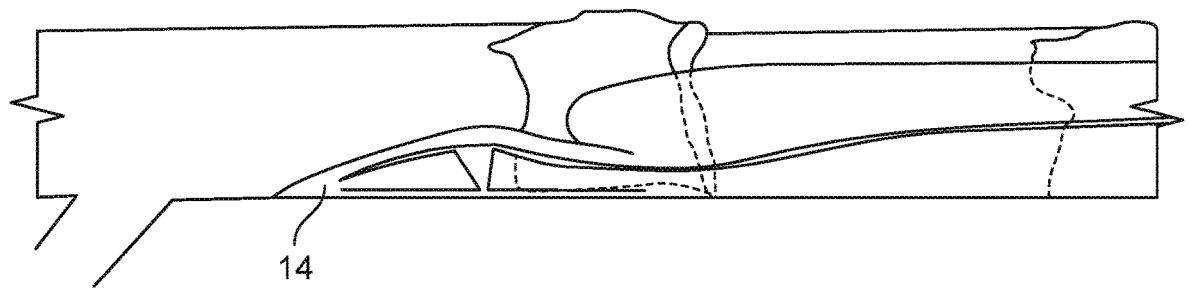
14  FIG. 17C

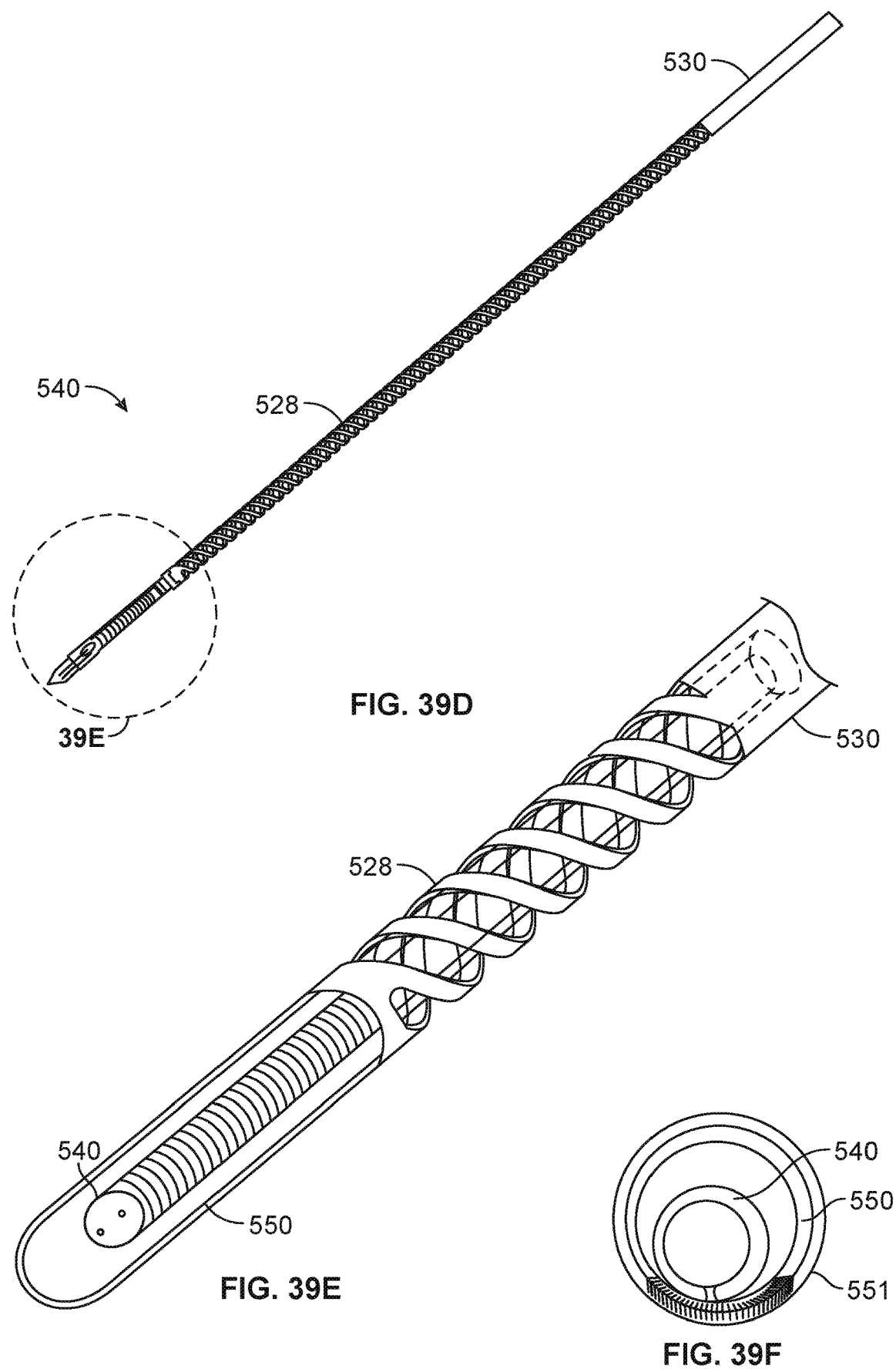

EXCISIONAL DEVICES AND METHODS

BACKGROUND

Embodiments relate to medical devices and methods. More particularly, embodiments relate to hand-held or mounted single or multiple insertion, single or multiple excisional devices and corresponding methods for vascular clearing and restoration applications. Embodiments further relate to improvements over currently used chronic total occlusion removal systems, specifically in providing minimally invasive and more widely capable reliable cardiovascular excisional devices and methods.

SUMMARY

Embodiments are drawn to various medical devices and methods that may be used for intra-vascular procedures. According to one embodiment, an excisional device may be configured to remove liquids, solids, semi-solids and single or multiple material samples during a single insertion through the skin (percutaneous procedure) into any vascular area of the body. Embodiments may comprise structures and functionality for different phases of a multi-phase vascular clearing or restoration procedure, which may be performed by hand or by device attachment to a stereotactic table stage or Magnetic Resonance Imaging (MRI) stage. Embodiments may also comprises devices configured for insertion through the central lumen of another compatible excisional device. Embodiments of a device, along with associated related subcomponents described herein, may provide the capability to retrieve solid, contiguous and/or fragmented materials as well as liquid and semi-solid tissues for analysis, diagnosis and treatment and exhibit improvements in functionality and performance relative to present devices and methods for clearing chronic total occlusions and other vascular anomalies. Although some embodiments find particular utility in cardio-vascular intervention procedures, other embodiments also find utility in, for instance, urologic and gynecologic applications, and are not limited therefore to vascular applications described, shown and claimed herein. Embodiments and elements thereof may be deployed in interventional procedures in coronaries, including bypass vessels (veins, internal mammary arteries, free radial grafts and in the case of peripheral vessels, synthetic grafts, native and bypass peripheral vessels including carotid arteries, renals, iliacs, femorals and distal vessels including venous and arterial vessels in various locations). Embodiments may include atherectomy and thrombectomy devices (those that remove plaque and other components of diseased vessel walls), which also contain a subset that may be used to treat both acute and chronic thromboembolic lesions and another subset that may be used to remove restenotic "scar" tissue obstructions (intimal hyperplastic lesions); chronic total occlusion devices, which include a variety of devices some of which may be considered variants of atherectomy devices and finally, delivery devices to deliver medications, implants, and devices such as other interventional devices performing functions listed above as well as guiding elements including catheters and various types of guiding and interventional wires, imaging catheters and wires, contrast media, oxygenation elements, sensing instruments, radiation delivery elements, protective and shielding devices, downstream safety devices and others. Embodiments may be configured to be portable, disposable or reusable and may be, for example, electrically/electronically-, mechanically-, hydraulically-, pneumatically- and/or manually-, powered, controlled and operated.

BRIEF DESCRIPTION OF THE DRAWINGS

FIGS. 17A, 17B and 17C illustrate views of a work element of a device in a vascular structure, according to one embodiment.

FIGS. 39A, 39B, 39C, 39D, 39E and 39F show details of a helical expander element, according to embodiments.

DETAILED DESCRIPTION

Figure 1:
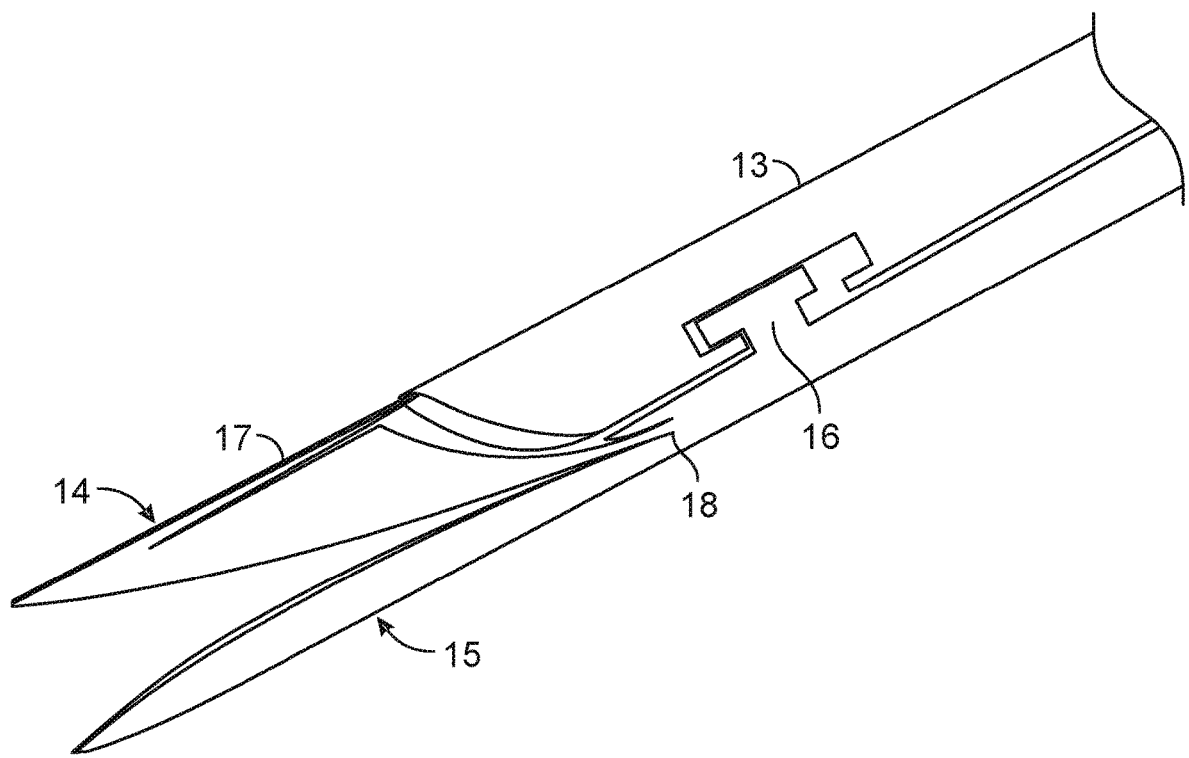
FIG. 1 is a perspective side view of a work element of an excisional device, according to one embodiment.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, a device for material or tissue excision may be configured to remove intra-vascular materials, and may comprise a range of work element dimensions ranging from, for example, approximately 0.0065" to 0.249" diameter (⅓ French to 19 French), or other appropriate dimensions both larger and smaller depending on applications and field of use requirements. According to embodiments, an excisional device may comprise a single tube or a single tube at least partially disposed within a coaxially-disposed outer tube or tubes, which outer tube or tubes may comprise a fixed or removable distal scoopula(s) or beak(s). A work element, according to one embodiment, may comprise one or more scoopulas and/or one or more beaks. Either may be fixed or articulable, sharpened or unsharpened at their tips or along their side axes, and combinations of the two may be interchanged, according to embodiments. In the case of either articulable beaks or scoopulas, the principles of action as described herein and according to embodiments may be similar or different to that used for one relative to the other.

Herein, beaks may refer to that portion of a work element whose primary functions may comprise coring, shaving or grasping to remove material, and may also be fixed, articulable, sharpened or unsharpened, and may have various features and shapes according to various embodiments. Beaks may comprise a longitudinal living hinge elements such that the beaks may be expanded "out of round" to a more flattened shape, or alternatively a more tubular shape than when at rest. Beak driving assembly or assemblies in the device may have operating characteristics and features to enable rotational speeds advantageously chosen to optimize "sweep" ultrasound imaging using mechanical array or at a different speed to increase the information provided with phased array imaging, for example and may include longitudinal and "off angle" sweep capabilities as they are articulated to "shine" ultrasound or light energy at various structures of interest. These capabilities can also be used to receive signals in return and/or for reference signal processing. These capabilities can also be used together with "light out, sound in" systems that combine light and sound efferent and afferent signal processing to increase information available using a combination of these modalities. These rotational, longitudinal "pullback" and angular speeds may be generally in the same range as useful cutting, pullback/advancement and angular speeds, or they may be outside that normal range and activated separately for diagnostic or other therapeutic procedures (radiation delivery, medication "painting", injecting or other delivery). Driving assembly or assemblies (hereafter, collectively "driving assembly" for ease of reference) for beaks may be controllable at the handle end of the device (e.g., outside the body) and can be quite sophisticated, reusable and electronically optimized for torque, rotational speed (rpm) and frequency (in the cases of translation, angular changes and oscillation motions). The driving assembly may also comprise variable control as needed and may also include the ability to halt work element motions at a part-off phase (a phase at which a cut or cored piece of tissue is separated from surrounding tissue), with automated rearward (proximal) translation for purposes of delivering excised materials (e.g., pieces of tissue) to a transport portion of the device where, according to one embodiment, vacuum along with fluid management flows and swirls may complete the rearward delivery into a serial collection magazine of the device. Driving mechanisms may also include delivery of electrical, mechanical, radiant, ultrasonic, electromagnetic, electron beam and simple magnetic, among other, energies distally to a work element area, whereby conversion or re-conversion to another energy form may be made in the work area. As examples, electrical energy may be delivered to a receiving electromagnetic device to mechanically actuate a distal element, or turbine power generated may be transmitted distally via inert gases or mechanical spinning of elements acting directly on a distal element or simply via fluids that may be present or introduced in the presence of spinning elements according to embodiments, that may function to both create vacuum at the distal work element area while also creating mechanical motion in another or the same element, such as a high speed, low torque rotational element such that simultaneous dissolution and sucking of debris such as clotted blood or particulate matter rearward and safely out of the work area may be accomplished. Yet another example is that an e-beam sent distally may be directionally by elements in the work area in which case energy is precisely redirected and focused by embodiments, rather than converted to another form of energy per se. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

In general, a scoopula may be a portion of the work elements of the device or may be a separate structure from the work element. A scoopula may be characterized by an elongated portion of their morphology, and may have among their principle functions to define and/or isolate a work area within a vascular structure, and may for that purpose be fixed or articulable, with sharpened or unsharpened edges, and with a variety of shapes, according to various embodiments. In one embodiment, the scoopula may for example, refer to a beak element in combination with an elongated half-round cutout section (not necessarily exactly "half" of the whole tubular section) where a portion of a tubular section proximal to a beak element has part of its wall removed, as described and shown herein. Additionally, both scoopulas and beaks may be primarily designated for rotation at low speeds, whereas beaks may be configured for rotation at speeds varying, for example, from 1 revolution per minute (RPM) to several thousand RPM, according to embodiments. However, according to one embodiment, a scoopula may perform functions that are the same or similar to the functions discharged by the beak or beaks. According to one embodiment, a first scoopula may isolate a portion of a work area while a second scoopula may isolate a part of a work area in concert with the first scoopula, and either may be used to core or shave materials as though it or they were a beak or beaks. Another work element having articulable beaks, according to one embodiment, may be configured to capture and remove materials in the thus isolated work area. In this manner, an operator need not be limited to using a beak versus a scoopula at any stage of an intervention, based on the demands of the operation, including for example specific functions or vascular anatomic limitations for which one or the other may be better suited, to be performed and the objectives to be achieved with the present device 10 and the accessories thereto.

Embodiments of devices comprising variations of scoopula(s) may be configured to isolate the working surface(s) from the flow surfaces. In use in a vascular lumen, for example, this means that the lumen and/or potential lumen (tight stenoses and complete occlusions, whether chronic or acute) space will be protected before and additionally as soon as there is sufficient space to permit blood flow, including gently forced flow for the purposes of downstream oxygenation and nutrition, introduction of imaging equipment, and natural flows based on driving pressures relieved by new or widened lumens. This space (the lumen space) is isolated from the working space so that any elements that are released during removal actions will be prevented from impairing flow in the protected flow lumen of the vessel being widened in caliber. This space will be utilized such that vacuum may be maximized in the working side of the vessel as defined by the scoopula, and also in certain embodiments, while protecting the flow side—an embodiment may simultaneously press against the wall on the flow side (opposite to the working side) causing the working side of a catheter to be pressed against the lesion side of the vessel so that the elements on the working side of a device may be held precisely at the desired depth (for example for removing as much or little of a lesion as may be optimal for various considerations such as transport, degree of aggressiveness, rate of removal, particulate size of the material being removed, as the working beak element(s) are given purchase). Embodiments also provide a stable, geometrically straight reference platform. This reference platform may be used to straighten a desired segment of a vessel such that a uniform depth of lesion material may be safely removed without the concern for asymmetrically removing deep-wall elements (for example in an otherwise naturally or as a result of disease, tortuous section of a vessel) that may lead to weakening, aneurism formation or even perforation during the procedure.

The scoopula thus may, according to one embodiment, serve as an isolating element, a reference platform, a delivery platform permitting downstream element introduction, a stabilizing element and as a preventer of distal embolization. Living hinge or hinges may be defined in one or more portions of the scoopula. These may include straight longitudinal (axial) curved longitudinal (spirals, complex diagonals, etc.,) and crossways configurations, as defined by kerfs cut into the tube from which the scoopula may be constructed. Embodiments may utilize any of these for example, depending on particular function, radius and degree of flexion and/or deflection, for use in specific vascular anatomic considerations among other considerations (whether or not more than one scoopula is used for example). Such configurations may enable expansion, variable, controllable rigidity, and geometry changes that enable tailored cuts that function as tip deflections, as well as for the purpose of temporary or permanent vessel expansion, the resultant forces of which may advantageously be directed in a radial direction, and scaffolding prior to stenting implant procedures or as stand-alone therapeutic procedures such as angioplasty of vessels, advantageously without the inherent strength limitations and non-directional expansion (radially) of typical balloon angioplasty technologies. Advantageously, distal flow around and/or through such structures may be less restrictive than balloon technologies that occupy the entire cross-section of a vessel such as an artery. Even when, in certain cases, very narrow spaces for distal flows are provided in specialized balloon devices, these are significantly limited in practical application and make these devices necessarily bulkier and harder to maneuver as a consequence. In contrast, according to embodiments, flow rates can be significantly higher based on expansion methods free of relatively thicker material and inflation materials. These configurations may also be used to enhance isolation and flow control on the proximal and distal ends of the isolation (working, non-flow) chamber. The sides may also be controllable with these living hinges to enhance working chamber isolation control. The back side of a scoopula may be configured to enable pressing the working side against the obstructive material. Such urging may be carried out with, for example, pontoon-type inflatables, struts that are themselves living hinge elements, and/or may be a portion of the existing beak-actuating tendons or may be separate elements, and/or may include structural living hinge portions that change the effective caliber and or geometrical configuration(s) of the device such that pressure may be applied in the direction opposite the obstructive material direction within a vascular structure. Spiral(s), lateral expansions (longitudinal scoopula living hinge(s)), and combinations of the above may all be incorporated into the scoopula or scoopulas, according to embodiments.

One embodiment is a device comprising two co-axially-disposed work elements. Whether a work element comprises of one or more scoopulas or beaks, or combinations thereof, two or more co-axially placed work elements (referred to herein as a complex work element) may have particular advantages with regard to cutting or coring efficiencies in certain tissue types or with certain obstruction matrices. For example, a first work element or portion thereof, may be configured as a tubular structure ending in a fixed or articulable scoopula. A second work element may be co-axially placed inside or outside of the first work element, and may comprise one or more articulable beaks. According to one embodiment, the beak driving assembly and the scoopula driving assembly (which may be one and the same) may differentially rotate the first and second work elements such that the beak or beaks of the first work element may be driven in rotation at a first speed and/or direction and the scoopula or scoopulas of the second work element may be driven in rotation at a second rotational speed and/or direction that may be different from the first rotational speed and/or direction. In such an embodiment, open beaks may be extended distally along the length of the scoopula, and the beaks rotating differentially (at different speeds or in different directions, relatively) may create a shearing action between edges of the beak(s) and the sides of the scoopula(s), for example. Additionally, as the beaks are extended distally up to and even beyond the end of the extended portion of the scoopula(s), the scoopula(s) may serve as a tissue or obstruction anchoring mechanism, and cutting efficiency of the beak tips may be greatly enhanced as a result. As a second example, and according to one embodiment, a complex work element may be composed of work elements comprising two or more beaks. The ability to fine tune the length or degree of beak tip exposure of one work element versus the other, and the ability to fine tune the differential rim speeds (rim in this case referring to rotating beak tips as tissue or obstructions are penetrated and severed) enables a clean coring action accompanied by a gentle attack on such materials to be cored. If oppositely rotating work elements are used, the tissue or obstruction to be cored may be presented with, for example, sabre-shaped cutting surfaces that minimally expose the tissue to the cutting blades and vice versa for maximum coring efficiency, according to embodiments. Additionally, precisely opposed cutting action may advantageously prevent twisting of underlying deeper wall components, which is a known risk factor for tearing, dissection and other unfavorable tissue disruptions with resulting complete occlusion and flow obstruction, as well as frank vessel wall perforation, often requiring emergency open surgical intervention. Even without discernable acute events, deeper subclinical tissue disruption may lead to more aggressive healing responses in time leading to thrombus formation during the initial recovery period and restenosis due to intimal or deeper, hyperplasia of a vessel during the more extended recovery period. A stable scoopula edge in combination with a rotating inner or outer cutting element, according to embodiments, achieves this favorable effect (non-twisting cutting action) as may two or more oppositely rotating, separate beaks or scoopulas with their crossing distal edges, according to other embodiments. These are all included in various embodiments herein as are other elements that further stabilize complex work elements, for example, backside struts among others (asymmetry of expansion forces as another example).

As used throughout this disclosure, work elements may comprise one or more tubes, and the terms "inner" and "outer" tubes may be used with reference to a single work element, or in reference to two or more co-axially located work elements (or "complex work elements", as used herein), each of which may comprise one or more tubes to enable their specific function. A coaxially-disposed outer tube, according to one embodiment, may also comprise one or more coatings. According to one embodiment, an outer tube may comprise a stainless steel hypodermic tubing ("hypo tube"). Such a stainless hypo tube, according to one embodiment, may be provided with (e.g., laser) cuts to define a monolithic distal assembly that defines beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. According to one embodiment, portions of the tube may be rigid. According to another embodiment, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element. Similar elements, structures, features and functionality contained in this disclosure are disclosed in co-pending and commonly assigned U.S. patent application Ser. No. 13/973,898 entitled "SOFT TISSUE CORING BIOPSY DEVICES AND METHODS"; U.S. patent application Ser. No. 14/050,771 entitled "SOFT TISSUE CORING BIOSPY DEVICES AND METHODS"; U.S. patent application Ser. No. 62/052,070 entitled "SOFT TISSUE BIOPSY OR EXCISIONAL DEVICES AND METHODS"; U.S. patent application Ser. No. 62/052,591 entitled "IN-SITU MATERIAL DELIVERY DEVICES AND METHODS"; and U.S. patent application No. 61/876,977 entitled "TISSUE CORING BIOPSY DEVICES AND METHODS", the entire disclosures of which are hereby incorporated herein in their entirety.

FIG. 1 is side view of a work element 13 constructed of a single tube with an articulated beak 14 and fixed (in terms of flexion) scoopula 15, according to one embodiment. As previously described, the features of the work element may be cut from a single tube including the incorporated scoopula, which only needs to travel a short distance in concert with and relative to the flexible beak. Such a work element enables matching lips (of the beak and scoopula—not just at their tips), or tips only, with scissors mating at lateral lips overlap during, and at closure, and includes living hinge element 17, living tendons 18, travel limiting structures such as keystone element 16, and a movable scoopula 15. In this view, the tendon elements are also incorporated into the scoopula to enable simultaneous motion of the scoopula and the beak 14. According to embodiments, living hinge 17 features may include cuts to define their limits such as straight, longitudinal (axial), curved longitudinal (spirals, complex diagonals, etc.), and crossways type cuts or kerfs. Such configurations may thus enable expansion; variable, controllable rigidity; and geometry changes that enable the tailoring of the cutting action of the device, such as tip deflections. These features may also be used to enhance isolation on the proximal and distal ends of the isolation (working, non-flow) chamber that may be established intra-vascularly using a work element of this embodiment. The sides of the work element may also be controllable with these living hinge elements to enhance working chamber isolation control. The sides or lateral lips of the scoopula portion may be slightly tighter in terms of their tubular radius, such that upon flexion of the beak portion, a scissors action occurs advantageously to enhance separation of material from its attachment to host tissues.

Figure 2:
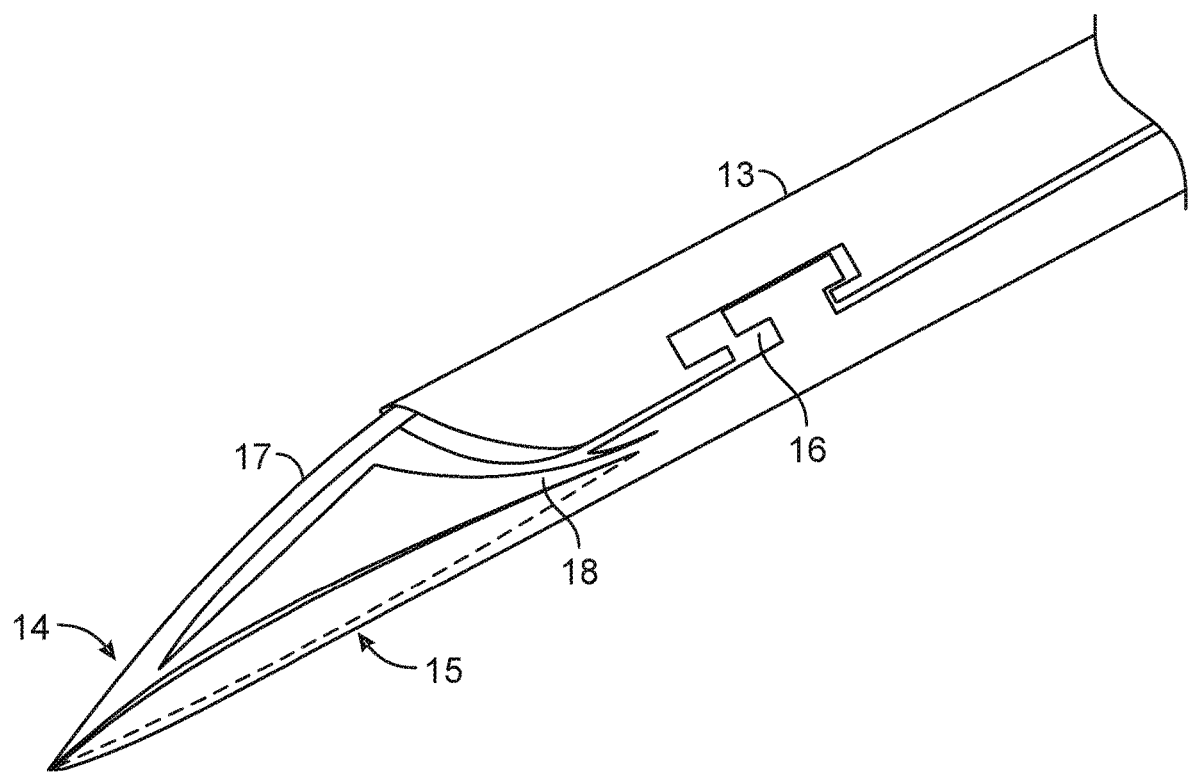
FIG. 2 is a perspective side view of a work element of an excisional device, according to one embodiment.

FIG. 2 illustrates another view of the work element 13 of FIG. 1, this time with the beak element 14 closed down into the scoopula (as may be compared to the keystone 16 position relative to that shown in FIG. 1). The position of the keystone element shows additional space for "diving" overdrive closure of the beak element 14. Additionally, the scoopula portion is in a slightly more proximal or slid back position (relative to the flexible beak element 14) to mate with the tips and/or side edges of the beak element 14. The degree of under- or over-bite may be configured to suit certain clinical needs that may be tissue characteristic dependent in some cases. The degree of extension of the scoopula portion beyond the beak 14 could be used to limit exposure to extremely sharp elements such as beak tips for example. The dashed line at the bottom of this figure represents where the beak tip(s) and side edges will meet the scoopula when fully closed in this example, though those points may change slightly with overdriven closure. Actuating such a work element 13 may be carried out by moving one half or more or less, of the horizontally split tube relative to the other in any number of ways or mechanisms, including a proximal handle 12 incorporating a simple scissors-type action, among others. The back or dorsal side of the scoopula 15 may be configured to enable pressing the working side against the obstructive material to be removed from an intra-vascular space. Such pressing functionality may be carried out by, for example, inflatable structures, struts that are themselves living hinge elements and that may be a portion of the existing tendons 18 or separate elements, and/or structural living hinge portions of the scoopula(s) itself/themselves. For example, an inflatable element may be part of or may replace tendon structures, and may likewise be a part of backbone living hinge elements to enhance expansion to perform directional angioplasty and to augment flow channel spaces. These structures may effectively operate to change the caliber and or geometrical profile or configuration(s) of the distal end of the device, such that pressure may be applied in the direction opposite the obstructive material's direction. Spiral(s), lateral expansions (longitudinal scoopula living hinge(s)), and combinations thereof may all be incorporated as elements and features of a work element 13.

Flexible (non-rigid) "flap" or one-way distal valve element(s) may be introduced to prevent distal embolization or to further isolate areas for pressure augmentation via channels in this and other embodiments, while additional lumens or channels may be used for contrast injection, flow augmentation, guide wire passage, imaging element passage such as phased-array "ultrasound on a wire" intravascular ultrasound (IVUS), fractional flow reserve (FFR) and instant wave-free ratio (iFR) devices among others, which are available on flexible wires ranging from about 0.009"–0.018" for example. The scoopula itself or the beak elements can be a mounting point for imaging technologies such as optical coherence tomography (OCT), IVUS, near infrared and other imaging modalities and combinations to assess such factors as plaque vulnerability among others. Channels may be provided for fluid management including delivery and vacuum. A channel could be used for example, to over-pressurize a proximal segment while measuring iFR or FFR distally, to augment functional gradient measurement to gauge functional significance of stenotic segments before, during and after interventions, particularly in cases where it may be helpful to overcome limitations of abnormally decreased ambient intraluminal pressure as a result of impaired left ventricular function or sequential stenoses, and in cases where there may be a desire to avoid use of pharmacodynamic agents such as adenosine when performing functional studies.

Figure 3:
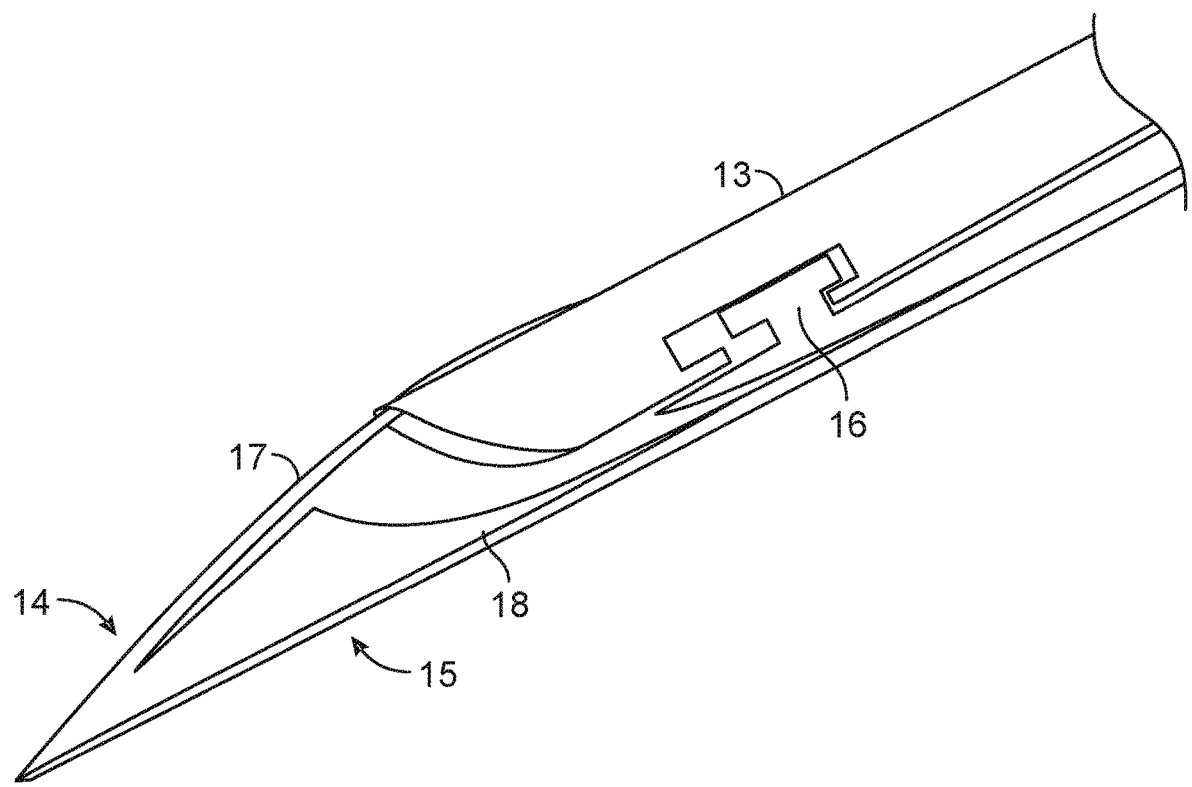
FIG. 3 is a view of a work element of an excisional device, according to one embodiment.
Figure 4:
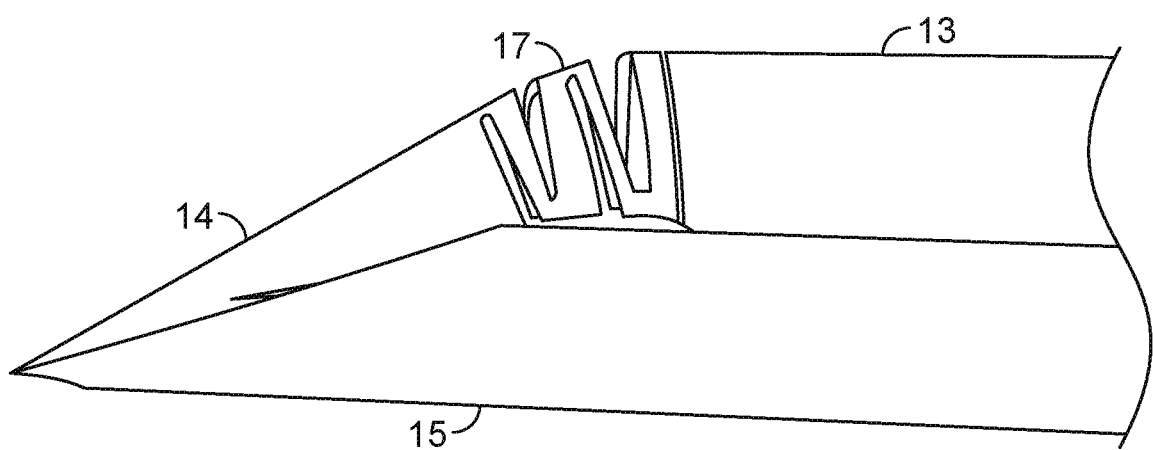
FIG. 4 is a view of a work element of an excisional device, according to one embodiment.
Figure 5:
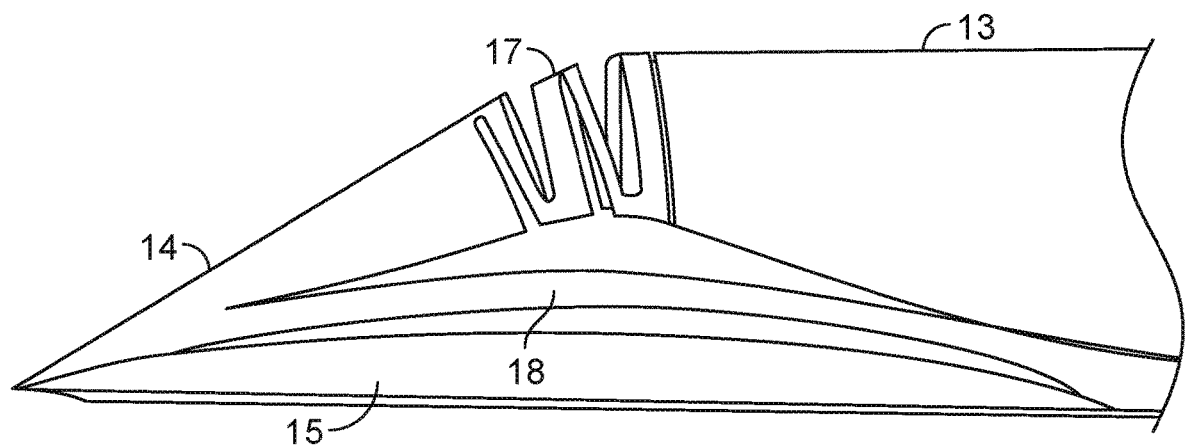
FIG. 5 shows a work element of an excisional device, according to one embodiment.

FIG. 3 shows a work element 13 that features a flattened scoopula or "scoopatula" which could be made from a preformed tube (mandrel/drawn plug techniques), according to one embodiment. Such a work element may be especially useful for tight spaces, potential spaces, and where multi-rotational spinning to excise materials is not required or where such a motion may be replaced by another type of energized motion. Such other type of energized motion may comprise, for example, high frequency mechanical reciprocation and may include delivery of energies ranging among the medically useful electromagnetic frequencies. The bottom tray may constitute one pole of a bipolar-energized system for example, while other components of the beak working element may constitute the other pole in order to enable high concentrations of energy delivered precisely and limited to only those surfaces intended for cutting. This embodiment may also be useful where shaving along a flat surface may be desirable, especially since the top flexible beak would now no longer need to be constrained to matching a circular "beak" shape in front profile, such that the top surface (flexible beak element 14) could be a much-widened shape or may be shaped as a low, flat arch. As an example, skin grafting operations may benefit from such an arrangement that may permit a shallow or skimming cut, taking a different advantage of the living hinge, tendon actuated beak—scoopatula combination. Proper geometry relationships between beak and scoopatula tip edges could, in this configuration, be used to create a slight opening between the two elements during overdrive (permitted by the extra space in the keystone as shown). The degree of opening could be controlled by the extent of scoopatula arching away from the beak forward edge(s) as actuated by the degree of overdriving. This could have the effect of advantageously creating a controlled depth of skim while advancing the device along a tissue plane for shallow tissue harvesting for example. Likewise, more flattened profiles may permit increased flow around devices variously configured in low profile according to embodiments FIG. 5 shows a side view of a work element 13 that is similar to that of FIG. 4 but now depicts a cut-down extremely low profile scoopula 15 for ease of pre-crossing a tight space or a total occlusion using, for example, the scoopula, according to one embodiment. The distal "half-umbrella" element on the scoopula, may be configured as a flap, valve or also as inverted scallop shapes. This element may be made of thin (<0.001") membranous material that lies flat at the "bottom" of the distal scoopula, only rising to function when confronted by pressure differential/flow differentials, or it may be generally upright/expanded but easily squashed down against the distal scoopula bottom as it is passed through a tight spot. Because it forms the distal (forward) wall of the working chamber, to complete the isolation and trap any distal embolization, its resting state can be obstructive. Flows distally to the scoopula configured in this way may be provided by the scoopula bottom, which also forms an isolating lateral wall permitting flow on its back side while completing the isolation for the working side of the device with the help of a distal flapper valve (not shown). The scoopula may be shaped to form a minimally displacing cross section, such that it may be able to pass through even the smallest opening or may create its own opening in an area where there exists only a potential space or no space at all in which case the low profile shape with optionally an extremely sharp or energized distal edge(s) may be used to open a passageway. Its shape may be streamlined like a broadhead arrow or a scalpel blade as an example and may be equipped to pass over a guiding element such as a traditional guide wire that itself may be manipulated with a torque tube passing along or through a scoopula channel (not shown in this illustration) provided for such instruments, such that various guiding wires with a variety of available tip and stiffness characteristics can be introduced and manipulated into a distal lumen beyond a total or near total occlusion.

Figure 6:
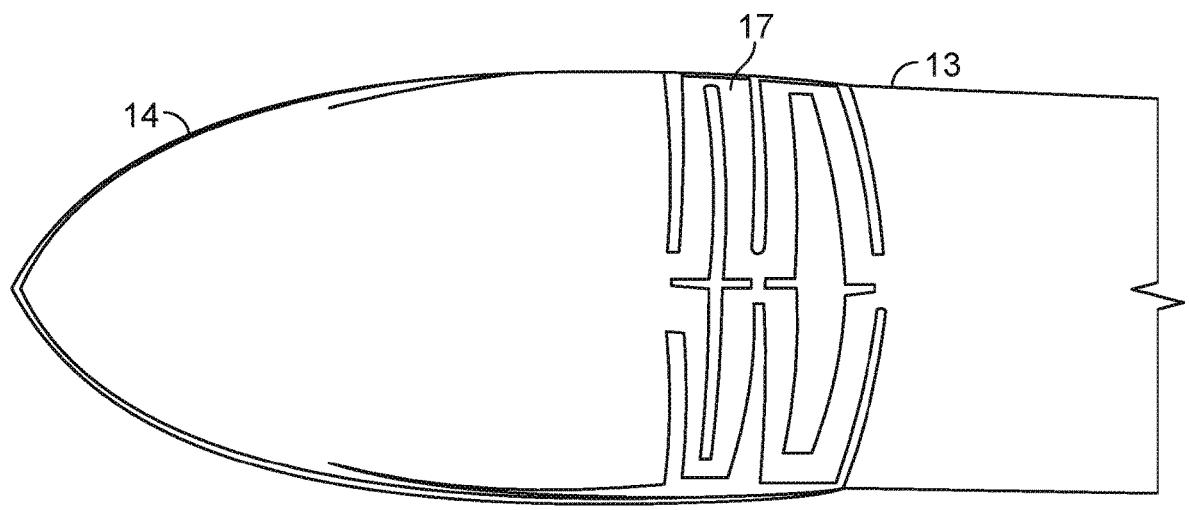
FIG. 6 shows a top view of a work element of an excisional device, according to one embodiment.

FIG. 6 shows a top perspective view of a work element 13 and beak element 14, showing a load-sharing, short axial-length living hinge 17, according to one embodiment. As shown, this particular living hinge 17 configuration may allow for an extremely tight radius of curvature and yet, its pattern would be simple to make for a laser cutter from a single hypo-tube, since laser cutters are already used to creating square geometric cuts for structures like vascular stents. As shown, the living hinge portion of the work element of FIG. 6 has been cut on either side thereof, from outside edges thereof towards the center. Such cuts may be perpendicular to the long axis of the work element or at another angle. Center cuts, extending axially and generally perpendicular thereto, may also be formed between the side cuts, to enable an even tighter bending radius of curvature when the living hinge flexes.

Figure 7A:
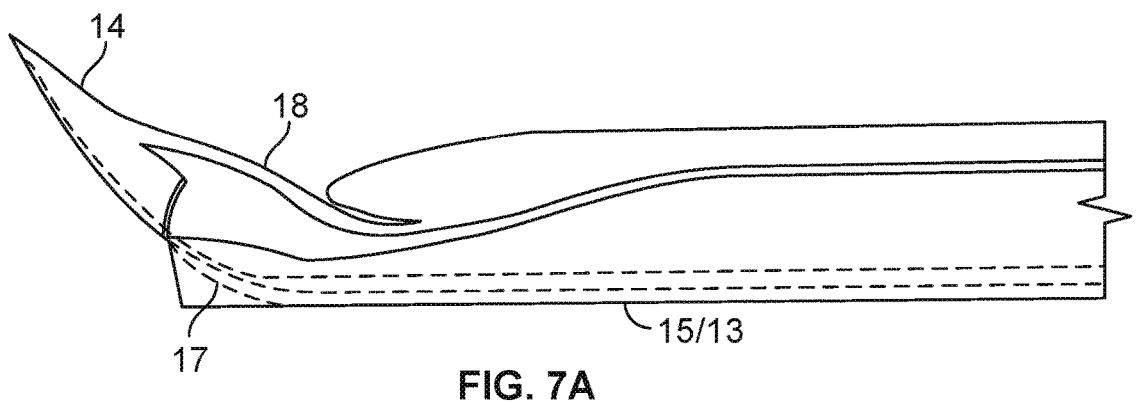
FIGS. 7A, 7B, 7C and 7D show side perspective views of a work element of an excisional device, according to one embodiment.
Figure 7B:
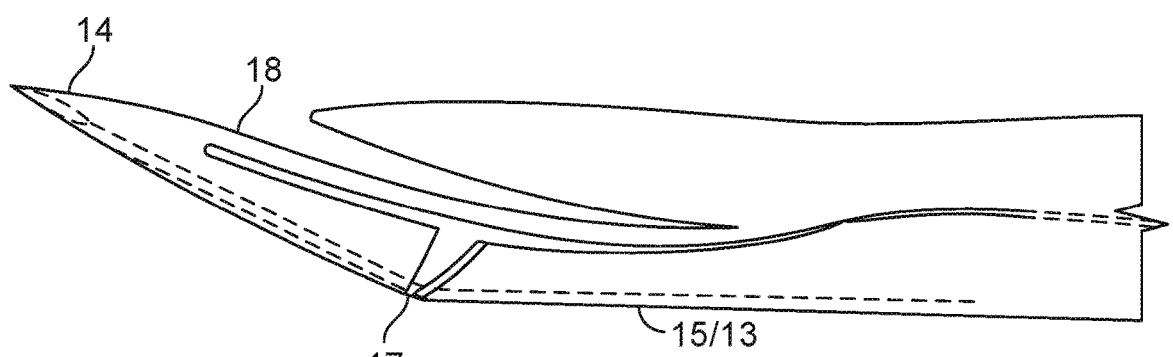
Figure 7C:
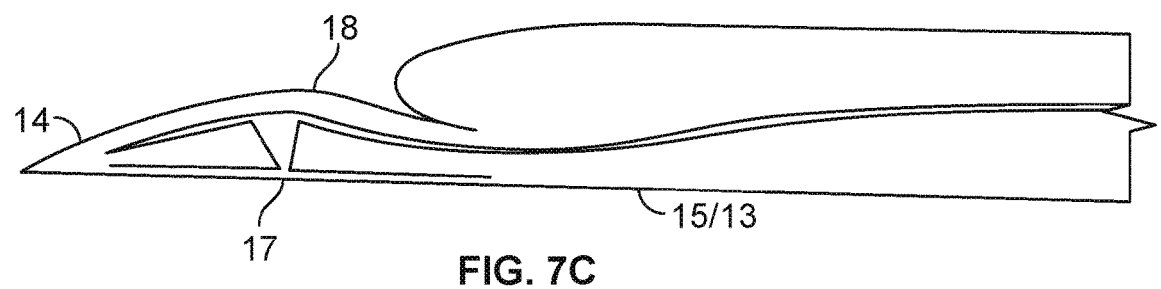

FIGS. 7A, 7B and 7C depict side views of three variants of a work element 13, specifically useful for vascular applications, and rendered in "5 French" "6 French" and "7 French" sizes (three common coronary intervention sizes, shown in scale relative to one another), according to one embodiment. These work elements may be configured to perform three or more basic functions. In this embodiment, the scoopula 15 is configured to be articulated and flex. Such a flexible scoopula is well suited to cross tight spaces with an extremely small frontal area, or low profile. The work elements shown in FIGS. 7A, 7B and 7C are further configured to expand as the flexible beak or scoopula is made to flex, so as to make them able to gain purchase on an opposite wall of the vessel, enabling the device to then press there against for later phases of an operation, or may simply be used to expand a vessel without the need for an inflatable device (balloon) that may disadvantageously block distal flow. The expansion is brought about by a "bow-stringing" effect of one or more of the tendons and this bowstringing effect is augmented by the shape of the more proximal portion of the tendon(s) as shown. The interference of the tendon shape, coupled with a mirroring shape in the main body of the tube, creates a ramp or wedge effect that serves to force the proximal portion of the tendon up the ramp of the tube forcing the whole structure to assume a larger effective cross-section area. The work elements may also be configured to create an "open" pathway for blood flow when the elements are laterally expanded as shown in FIG. 7A. Such work elements are, therefore, configured to permit distal flow of oxygen and nutrient carrying fluid (blood flow), such that the supply of these remains intact (or is established meaningfully for the first time since blockage by plaque or clot may be significantly or completely obstructive prior to device expansion) from proximal to distal vessel outflow. Also shown in FIGS. 7A and 7B is a living hinge element that is also a tubular structure whose distal port is located near the tip of the beak element. This enables passage of fluids, guide wires and others and the location enables placement and directing capabilities using beak flexion alone or in combination with whole scoopula twisting. Between these two actions, any location on the face of an obstruction could be accessed. In effect, elements could in this way be steered along as a scoopula is advanced through tortuous pathways. Additional functions carried out by the work elements of FIGS. 7A, 7B and 7C may include isolating the wall upon which the other parts of the device will be working to clear out materials and to catch any debris that may break off as the device 10 clears an occlusion, for example. Not shown are membranous coverings, which may have pores correctly-sized to catch any downstream-occluding-size debris, while permitting normal blood flow. These scoopula may be used to create a work platform through or over which, other work elements may be introduced to the area for diagnostic and therapeutic interventions. These embodiments may be monolithic in that they may, be created from a single tube, but as shown in FIG. 7A, there may be folds in the backbone structure that may act as channels for flow or for introduction of additional work elements, as indicated by dashed lines, and these may extend into the beak elements such that the distal opening of these channels or tubes may be directed by flexing of the beak element, alone or in combination with twisting of the entire device. The dashed lines may also indicate additional rigid or collapsible tubular structures, for the purposes of introducing various types of diagnostic and guiding wires, and may also be used for introducing vasoactive medications, thrombolytic, platelet inhibiting or contrast agents among others.

Figure 7D:
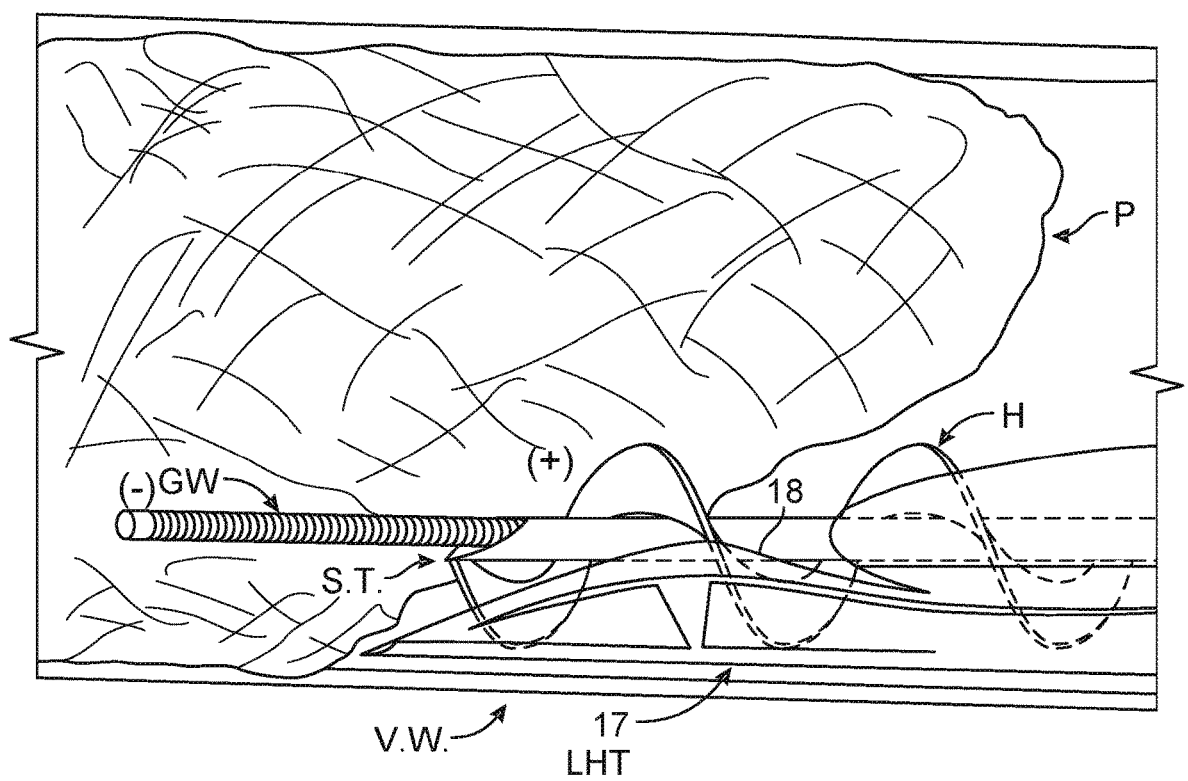

FIG. 7D shows an additional work accessory, in this case a helical element with a central tube or shaft that may be advanced to a distal location within or beyond a scoopula. In FIG. 7D, H=helix, which is a powered helix that pulls the scoopula along, P=plaque, GW=guide wire, ST=sharp tube tip, VW=vessel wall and LHT=living hinge tubular element. The GW guide wire is marked with a (−) to indicate that this element may be the negative pole in a bipolar radiofrequency or other energy system and a (+) sign is located at the tubular front edge of the helical element H to indicate the positive pole completing the circuit in an RF or radiofrequency system. These locations are only exemplary in nature. Indeed, the poles may be located elsewhere, such as along segments of the helical edges themselves among other potential locations, where, by virtue of the shearing motion of these edges constantly clearing away any coagulum, carbonization or other insulating debris from the polar surfaces, cutting efficiency may be enhanced and maintained. Importantly, in such a configuration, the delivery of the RF energy is substantially limited to the area between the bipolar elements and in this case, the scoopula element may serve to further limit the spread of RF effect. In particular, the scoopula element advantageously minimizes any such RF effects directed towards the vessel wall components, which may otherwise stimulate an exaggerated healing response, leading to intimal hyperplasia and restenosis. The helical element may be free advancing with rotation but at any point, it may be used to pull the scoopula along by constraining its relative forward motion with respect to the scoopula within which it rides. In this manner, forward powering (distal translation within a vessel and its plaque) of the scoopula and helix could be advantageously independent of the need to push the scoopula along by applying pressure from the most proximal point of the structure. This action advantageously eliminates or minimizes the need for guiding catheter back up support since the rotating helix and scoopula are pulled along by actions of the helix on the plaque. In this case, the scoopula acts as an important shield to protect areas of the vessel that should not be subjected to the helix action due to the damage it may cause. Additionally, the helix, being flexible in embodiments, could be directed away from sensitive areas by flexing the scoopula tip alone or in combination with twisting of the entire scoopula.

Figure 8:
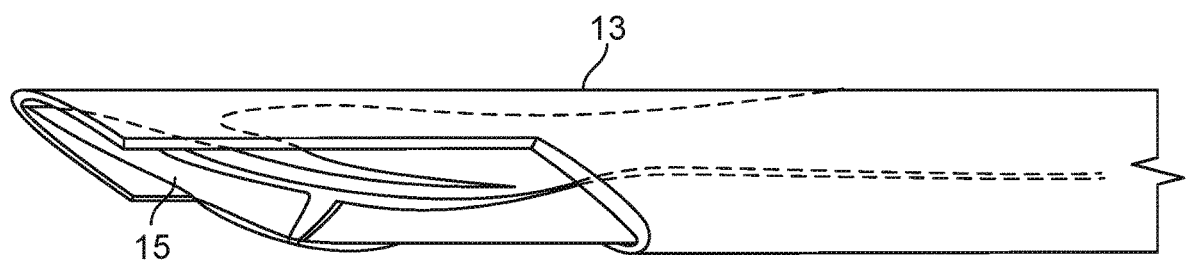
FIG. 8 shows a work element of an excisional device, according to one embodiment.

FIG. 8 shows a side view of a work element 13 according to one embodiment, comprising an external cutting element formed from a separate tube and an internal element, which may be similar to the scoopula 15 of the work element shown in FIG. 7A. The external cutting tube may be differentially rotated, oscillated (rotated clockwise and counterclockwise) or be moved in an axial (forward or backward) direction relative to the internal element to complete an excision all the way to complete part-off. In this depiction, the bottom element 15 may be rotated differentially compared to the top element 13 (which may or may not, in this case, itself rotate or oscillate to shave or core and part-off).

Figure 9A:
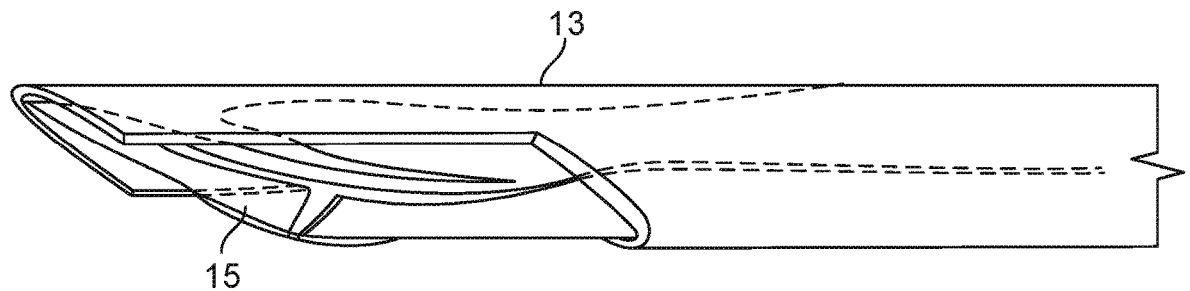
FIGS. 9A and 9B show side views of a work element of an excisional device, according to one embodiment.
Figure 9B:
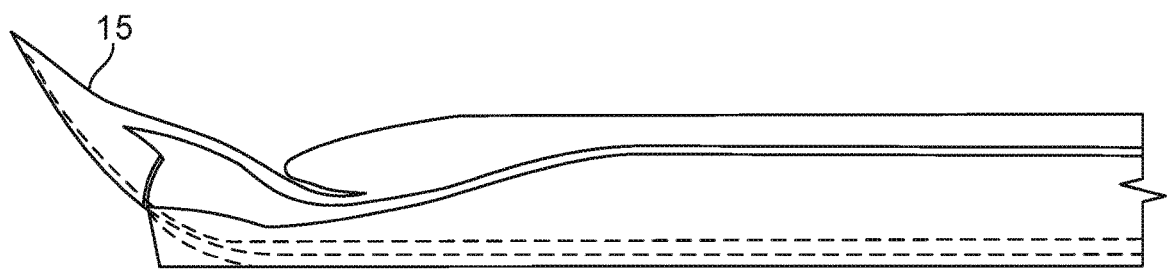

FIG. 9A shows the work element of FIG. 8 with the completed part-off excision shown in the top illustration. In the bottom illustration, FIG. 9B, the flexible scoopula 15 is in its maximally extended position within a portion of a vascular structure, in which position it can remain until forced to be more normally aligned by an advancing top external cutting element or component such as scoopula 13. This would ensure that no bits or chunks of debris from an intervention would float downstream before being captured and transported proximally all the way into a transfer magazine element and storage chamber element of a device. A suitable transfer magazine and other structures are disclosed in U.S. patent application Ser. No. 14/050,771, incorporated by reference above. Again outlined by dashes in FIG. 9A is one or more channel element(s) including exit opening near the beak tip. The location of this exit port ensures that any guidewire or other instrument would remain clear of the part-off mechanism, and at the same time, would be directable by beak flexing or rotation.

Figure 10A:
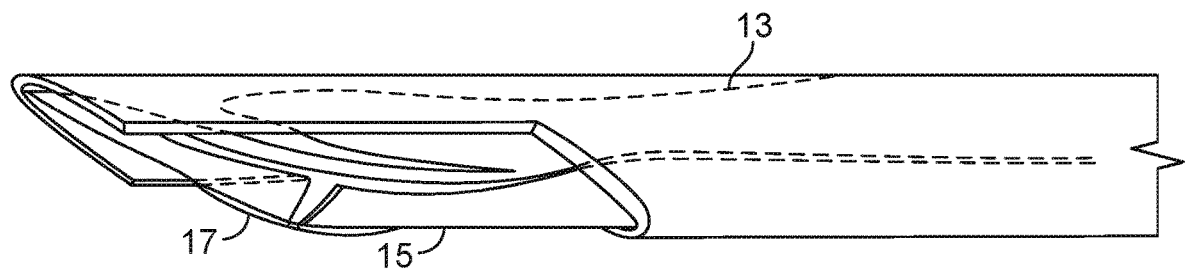
FIGS. 10A, 10B and 10C show a side view, a top view, and another rotated side view, respectively, of a work element of an excisional device, according to one embodiment.
Figure 10B:
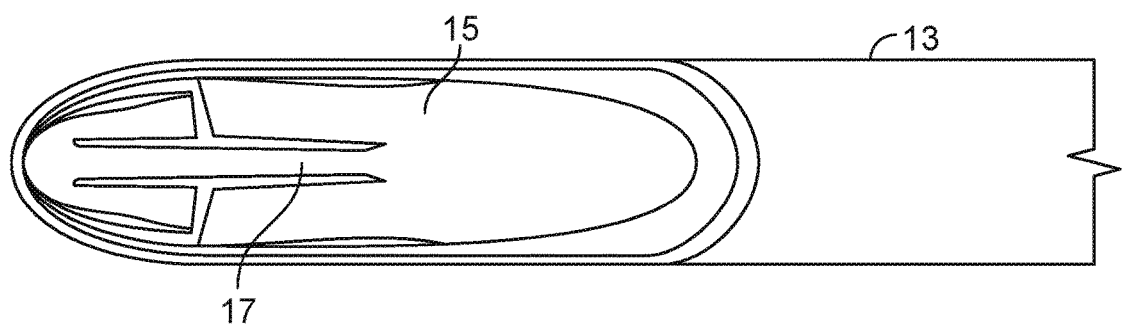
Figure 10C:
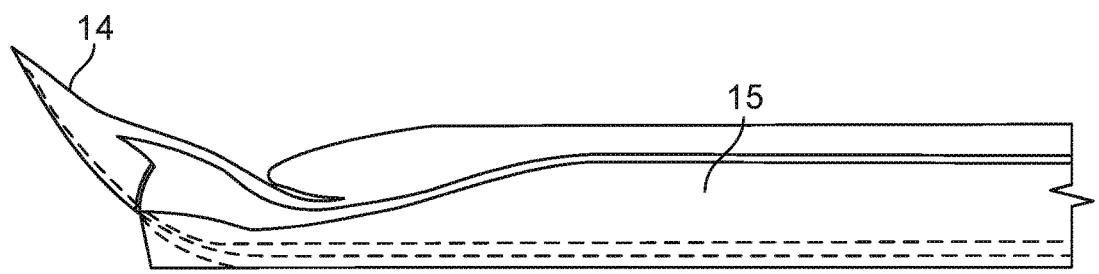

FIGS. 10A, 10B and 10C show different views of the work element 13 described above in FIGS. 9A and 9B, along with a view of an assembly of the two major components of the work element 13 from the top in FIG. 10B, showing one example of the living hinge elements 17 of the articulable scoopula 15.

Figure 11A:
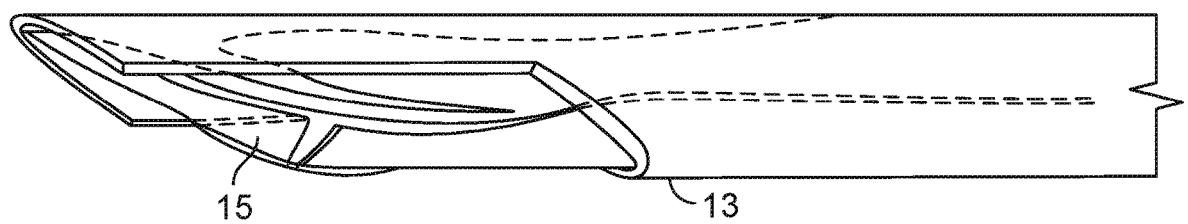
FIGS. 11A, 11B, 11C and 11D show various configurations of work elements of a device, according to embodiments.
Figure 11B:
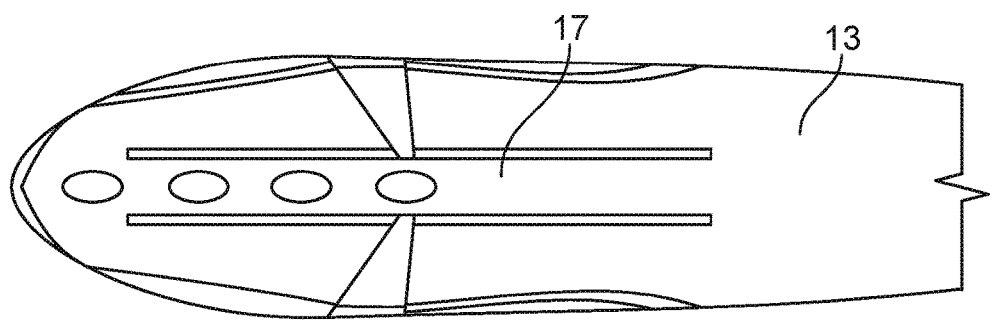
Figure 11C:
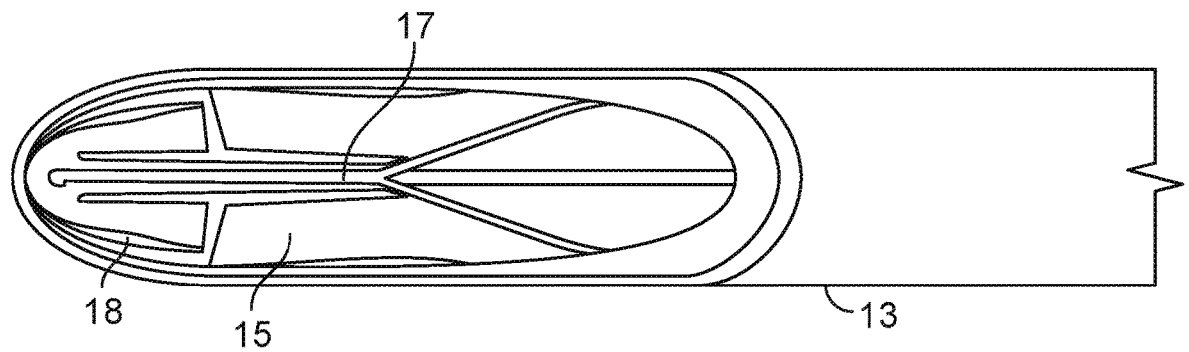
Figure 11D:
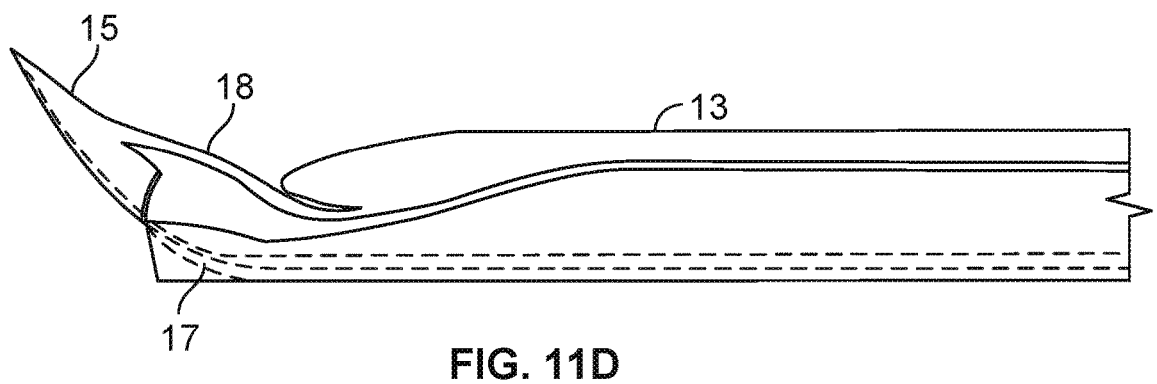

FIGS. 11A, 11B, 11C and 11D show guide element tracks confluence 17 as well as several exit point options for such guide elements, such as locating wires, or guide wires with any of a variety of imaging modalities attached to them or in place of them, according to embodiments. FIG. 11A depicts an external non-articulable-tip scoopula 13 and a work element having a flexible beak-type scoopula 15 disposed co-axially therein as described above relative to FIG. 10. FIG. 11B shows a bottom view of a work element 13 of scoopula 15 and a series of (e.g., laser-cut) apertures along the living hinge 17, according to one embodiment. These apertures may be disposed and configured to precisely place accessory devices, such as guide wires and others, as described below. FIG. 11C shows another arrangement of living hinges 17 and tendons 18 from a bottom view of an articulable beak or scoopula, according to one embodiment. In this example, living hinges 17 are formed of collapsible tubular structures available for introduction of various instruments or fluids as well as (when relatively non-collapsible) for the purpose of evacuation (using vacuum, for example). Other implementations for passing guide wires or other accessory devices from the central lumen of the work element 13 to the exterior within a vascular structure may be devised. FIG. 11D shows a side profile of a scoopula element 15 of a work element 13, with additional material removed between the living hinge 17 and tendon 18, and, substituted with tubular structures as shown in FIG. 11C acting as a living hinge element according to one embodiment.

Figure 12A:
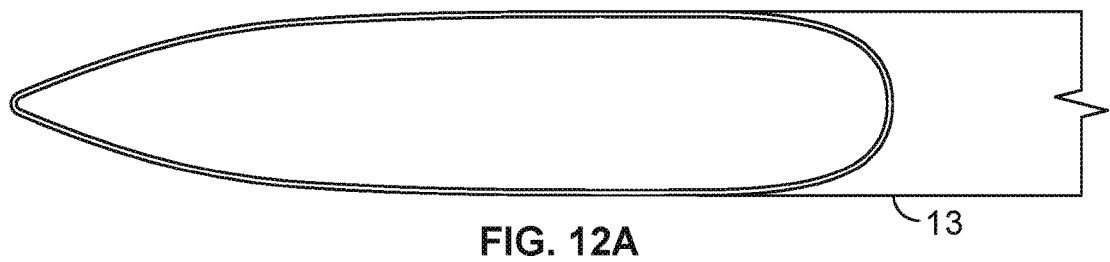
FIGS. 12A, 12B, 12C and 12D show various perspective views of work elements of a device, according to embodiments.
Figure 12B:
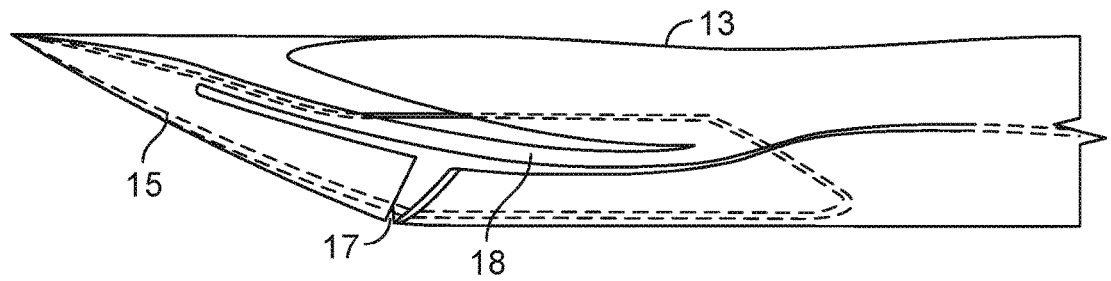
Figure 12C:
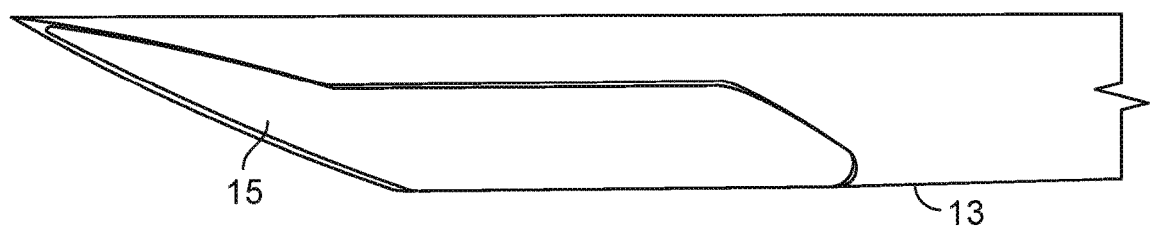
Figure 12D:
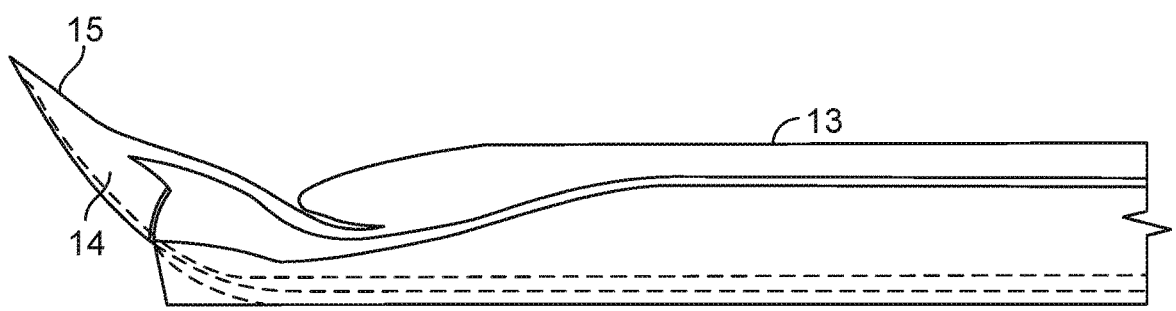

FIG. 12A depicts a fixed part-off structure of a work element 13, according to one embodiment. FIG. 12B depicts such an alternative part-off element of FIG. 12A now located on the inside of a flexible beak of a work element 13, according to one embodiment. Shearing action occurs advantageously between the two elements in a less aggressive way where a vascular wall is concerned, since the shaving/coring scoopula component is on the inner tubular space dictated by the flexible beak-scoopula element. The second or alternative fixed element is inside the inner diameter of the flexible beak element, particularly as shown in this figure and either or both of the elements may differentially rotate, oscillate, translate longitudinally or otherwise be differentially energized (bipolar elements for precisely, controllable RF or other energy). Interventional situations exist that may call for inside or outside shear/core/part-off elements, including provision of accessory pathways among others, the level of aggressiveness desired (cutting within the arc of the first element or outside it), and other considerations such as degree of distal blood flow enabled with each. FIG. 12C depicts an alternate shape with more defined "shoulders" for a fixed part off structure, and FIG. 1.2D shows one example of any number of configurations of a flexible work element 13. Note that the opening in the second fixed structure element may be of different lengths and/or shapes, as shown in FIG. 1.2A through 12D. Indicated by a triangle positioned along dashed lines in FIG. 12 is a living hinge/channel or tubular, combination structure along the "backbone" of element 15. These elements may be plural in number advantageously distributed laterally to add stability for example.

FIGS. 13A, 13B, 13C and 13D depict embodiments of exemplary accessory elements configured to work with devices according to embodiments. Such accessory elements may comprise a variety of imaging modalities as well as configurations of those modalities, depending on where the operator wants to look (forward or at a side wall, for examples) as well as depending on other elements that may be introduced to the working area within a vascular structure by such devices. Such accessory elements may comprise guiding element components such as torque tube(s) including straight, angled, rigid, bendable and torqueable, to work in concert with the scoopula. A guiding torque tube may be custom-made to work within the scoopula. A torque tube may be configured for different guidance modalities, which modalities may include phased array ultrasound, "OCT" (optical coherence tomography), contrast material delivery or any combination of those, as well as laser penetration and feedback elements ("smart" lasers) and may be used to introduce, control or augment functional testing instruments such as functional flow reserve measurement instruments (FFR) and instant wave-free ratio (iFR) measuring instruments as well as those imaging modalities (near-infrared) used to assess plaque vulnerability among others. A torque tube element may include a variant that enables obtuse angle delivery of guiding wire elements in case wherein the initial channel is not in the correct place. For example, it may be that the initial guiding wire placement is outside the potential lumen space. In that case, one embodiment may be configured to regain access to the original lumen (now a potential space) such that the original lumen may be accessed progressively by additional elements leading ultimately to passage of a larger scoopula, for example. Guiding wire elements may include traditional hi-torque, shapeable wires that are commercially available but may also include others devices such as those described in the above cited co-pending and incorporated US patent applications, which are sufficiently small as to enable distal delivery thereof via the scoopula of the present vascular device(s). The guiding wires may also include drilling end elements as optional variant instruments, for penetrating the "cap" face of most CTOs. Indeed, CTOs comprise a hard face—the "cap" component—a softer mid-section and, not uncommonly, a distal (usually softer than the face cap) cap. These variations may include the provision for active pumping of distal relieving fluids—such as oxygen/nutritional synthetics, agitated saline, vaso-relaxing, thrombolytic and antiplatelet agents and others to support the distal vascular bed, according to embodiments. FIG. 13 B is exemplary as a delivery and retrieval device that may include imaging and isolating components. The distal end for example, may comprise a central delivery area with venturi-effect or other vacuum generating structures incorporated therein and may be placed against a CTO face for example, and advanced as enabled by actions of its own functions as well as those functions of other introduced components or mechanisms (burrs, drills, hydro-dissection actions, corkscrew devices, etc.).

Figure 13A:
FIGS. 13A, 13B, 13C and 13D show views of different guide wires of a device, according to embodiments.
Figure 13B:
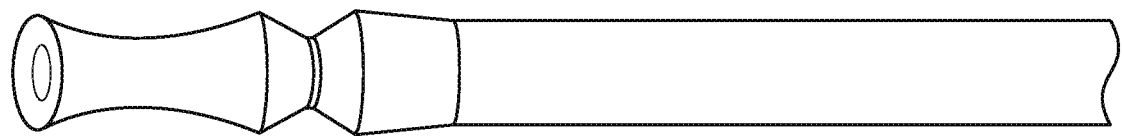
Figure 13C:
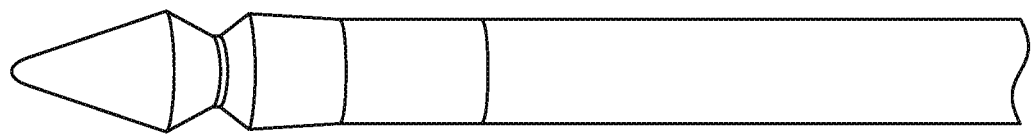
Figure 13D:
Figure 14A:
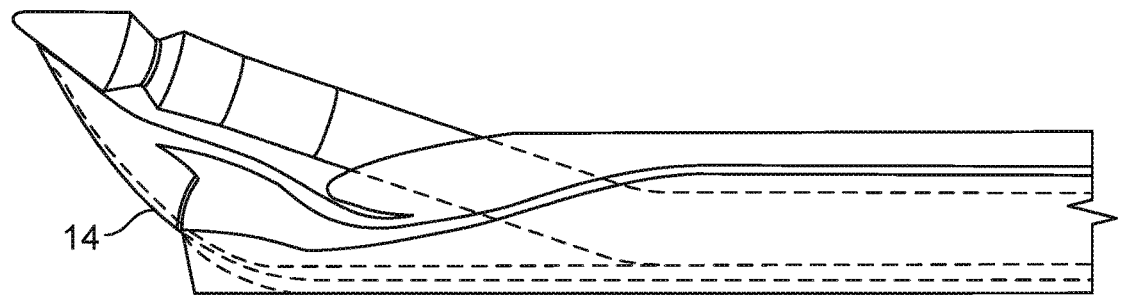
FIGS. 14A, 14B, 14C and 14D show views of guide wires in a work element of a device, according to embodiments.
Figure 14B:
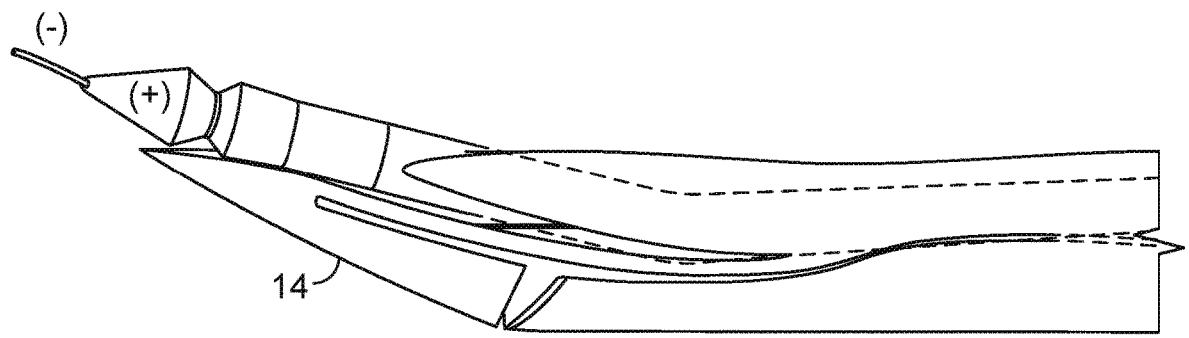
Figure 14C:
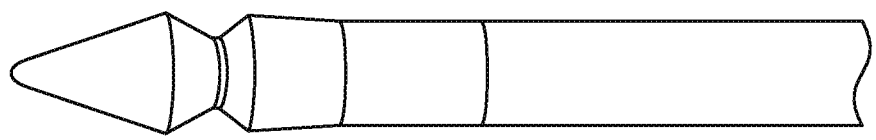
Figure 14D:
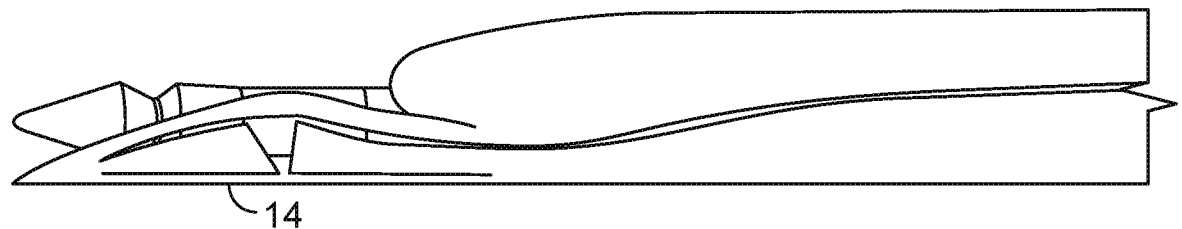

FIGS. 14A, 14B, 14C and 14D show use of one of the accessory elements, in this case the boring double cone element shown in FIG. 13C above, with incorporated OCT and/or Intra-Vascular Ultrasound (IVUS), according to embodiments. In FIGS. 14A and 14B, the flexible beak element 14 is shown presenting the work element of a device in various positions such that the accessory guidance is active on the part of the flex beak, and passive on the part of the working accessory, but only in terms of placement and continued manipulation of its direction. According to embodiments, the working elements may be configured to be active borers, vacuum sources, flushers, or mechanisms for delivery of guide wires; boring guide wire-type elements, RE deliverers or lytic agents, to name a few. FIG. 1.4B for example shows the guide wire marked with a (−) sign to indicate it could serve as the negative pole of a bipolar system such as radiofrequency energy (RF) with the distal tip of the double cone element serving as a positive pole and marked with a (+) sign. Alternatively, the bipolar leads may also be disposed at the two faces flanking the deep "V" in the double cone, which would serve to create and potentially preserve a gap between the two poles for efficient radiofrequency delivery while minimizing potential squelching of the energy transfer dynamic. These concentrated areas may advantageously increase energy density and, in concert with rotation, serve to keep the poles clear of debris, carbonation and other insulating factors that might otherwise diminish cutting efficiency that may lead to increased thermal transfer and damage. Additionally, flush/vacuum of fluids or discharge of inert gasses from the scoopula may also be provided to augment cutting efficiency while favorably diminishing unneeded thermal effects. FIG. 14D illustrates one of these accessories in at rest position in a beak element 14, itself at rest.

Figure 15A:
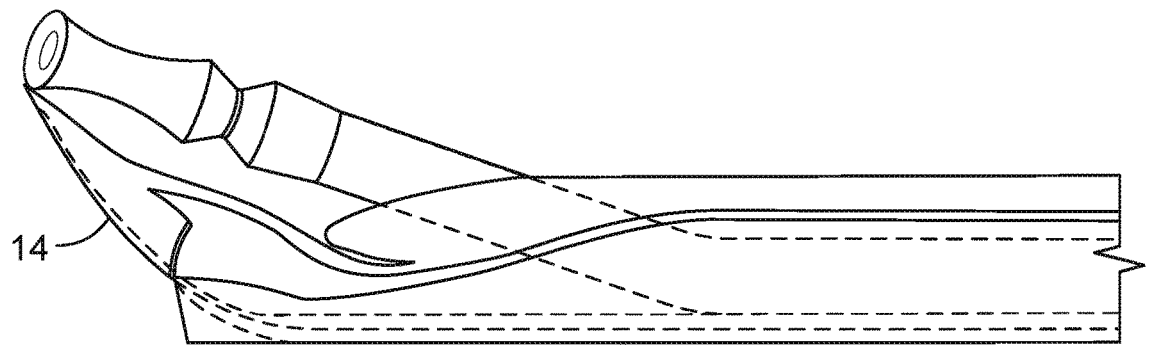
FIGS. 15A, 15B and 15C show a work element of a device at various angles of deploying a guide wire, according to one embodiment.
Figure 15B:
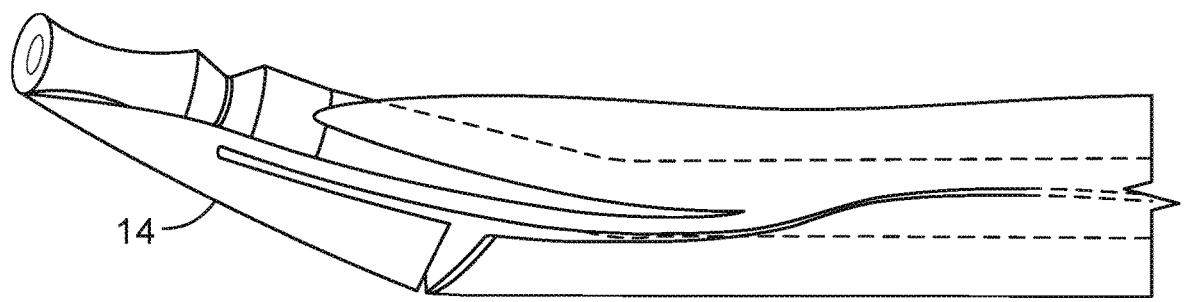
Figure 15C:
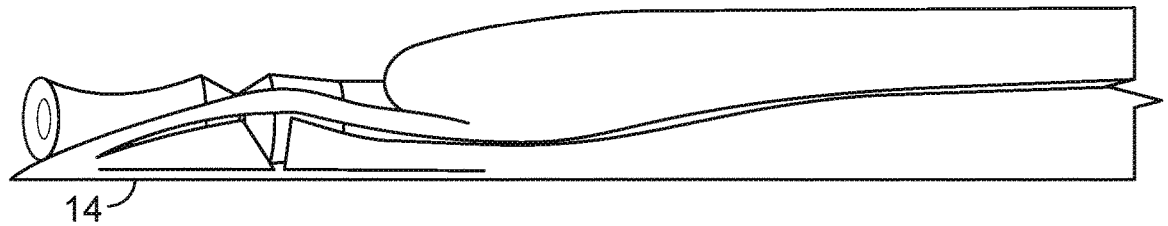

FIGS. 15A, 15B and 15C show another of the accessory elements shown in FIG. 13B, incorporated into the working element of a device according to one embodiment. This accessory element is configured for maximum imaging and support of other elements, against the face of a hard entry cap for example. This accessory may find particular use in CTO re-canalizations, where powerful imaging may detect a channel remnant such as an old thrombosis channel, which is often all that is left to suggest the easiest path forward through a CTO. This type of work element and device may enable maximum physical support while also permitting easy exchange of accessory elements without snagging upon retraction, and likewise permits use of maximally-angled accessory elements exiting its front end. Suction may also be applied to both stabilize the face as well as to retrieve any debris, some of which can dangerously create a local hyper-coagulable milieu that may spread both proximally and distal to the working area. Implied but not specifically shown in these figures are the succession of angles/articulated areas, designed to permit complex angling of accessory elements such as the previously shown one, as well as this element.

Figure 16A:
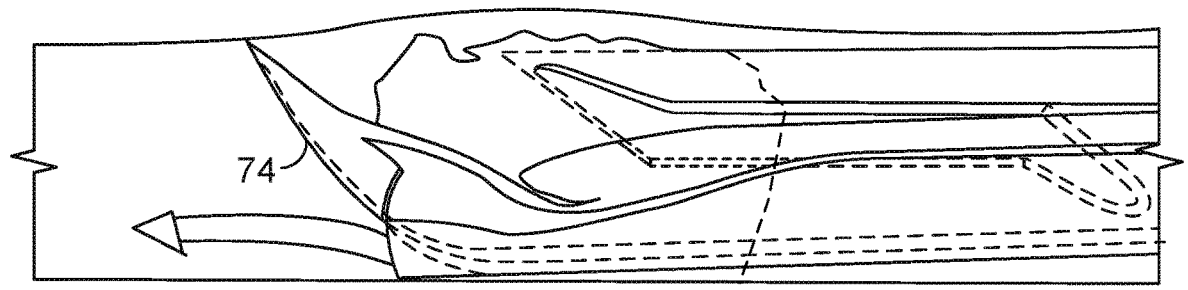
FIGS. 16A, 16B and 16C show a work element of a device in a vascular structure, according to one embodiment.
Figure 16B:
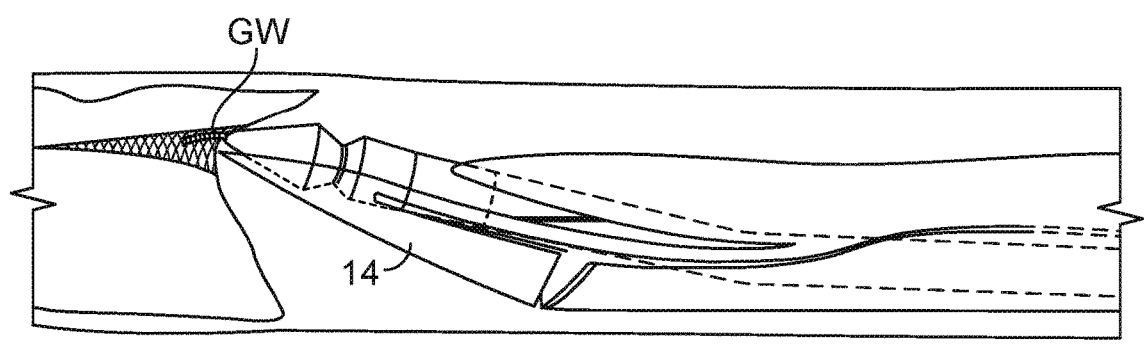
Figure 16C:
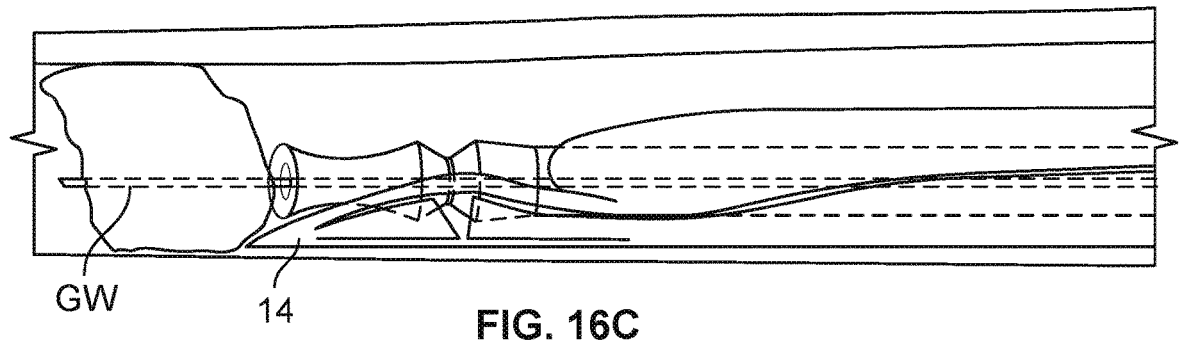

FIGS. 16A, 16B and 16C show three possible strategies when facing a hard total or nearly total occlusion, using a device according to one embodiment. The top figure, FIG. 16A, shows crossing the occlusion using a flexible beak element to scoot across the lesion, between the lesion and the most loosely anchored side. The flexible beak may then be flexed to isolate the lesion, which will be completely excised when the (in this case internal) opposite beak element is advanced (and optionally, differentially rotated). The middle FIG. 16B shows aiming the boring dart accessory element into the area suggested to be the optimal area by the shape of the face of the CTO. This is one of the traditional ways suggested by pioneer Andreas Gruentzig in his early work on CTOs and Acute Total Occlusions ATOs. The Lower figure, FIG. 16C shows use of an additional accessory element being delivered by an imaging/supporting/flush/suctioning element in a central area—in this case a boring guide wire, in scale representing a 0.035" size, which is a common peripheral wire. A smaller more appropriately sized coronary wire such as a 0.018" or 0.014" guide wire may also be used, according to embodiments. The aforementioned central area may be softer, and may represent the last remaining lumen now filled with organized thrombus as visualized by one or more of several scanning modalities delivered to the area and isolated by the accessory elements positioned and stabilized for optimal viewing and introduction of other instruments to reestablish a flow channel. These accessories may also participate in the delivery of cutting energies such as radiofrequency (RF) indicated by the symbols (−) and (+) to represent a bipolar delivery system and other energies that may be useful in ablating tissue that may resist forward progress through the occluded segment. The accessories may be configured to focus these energies to maximize precision of delivered energy while advantageously minimizing unwanted stray energy effects beyond the intended target area(s).

FIGS. 17A, 17B and 17C show a common scenario, particularly in peripheral vessels where more than one "cap" component of a CTO may be present in succession. These illustrations show three views of flexible beak advancement along the diseased intima of an occluded artery, according to one embodiment. FIG. 17A shows a flexible beak of a work element sliding under the first lesion, taking advantage of its low profile and circular shape to slide between intima and hard cap lesion into the fatty portion of the serial obstruction between the two caps. FIG. 17C at the bottom shows the flexible beak of the work element sliding under the second cap and exiting in the clear into some of the fatty plaque elements typically present near branching points, as illustrated. Note that since progress is being made, there is no need to introduce a second scoopula element for excision, part-off and rearward transport until this moment where the flexible beak is about to be flexed to protect the downstream vessels and permit flow. In such case, a guide wire element (not shown) may be advanced along the backbone of the flexible beak and placed distally to ensure continued access to the distal, patent vessel for any subsequent treatments (including the excisions themselves), according to embodiments.

Figure 18:
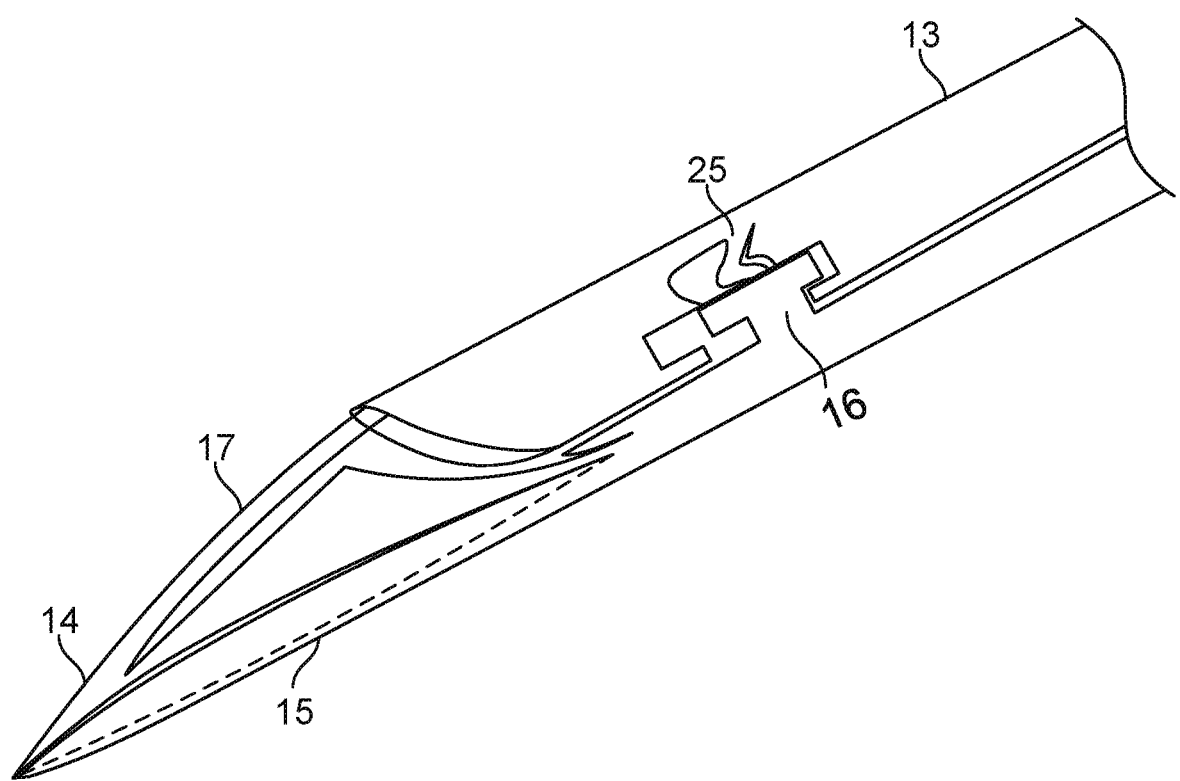
FIG. 18 shows a perspective view of a work element of a device, according to one embodiment.

FIG. 18 shows a perspective view of a monolithic work element 13 of a device, according to one embodiment. In this view, a work element may be configured to flex laterally. The ability to flex laterally may be advantageous in tight vascular spaces where curves may be encountered, and in which a device must not be permitted to perforate a delicate structure or wall. Activation of the beak mechanism may be at least partially controlled by a relative distal or proximal force in relation to the scoopula. In this view, a rolling strut 25 may be seen interposed between a travel limiting structure 16 of a single tube, monolithic work assembly, comprised of a fixed low profile scoopula 15 and opposed by a flexible beak 14. The rolling strut 25 stabilizes the travel limiter 16 laterally, particularly in the closed or at-rest position of the work element. Such rolling (or twisting or torsional) strut features may also be included in other sliding structures of the monolithic work element, according to embodiments. There may be several parallel, staggered, spiraled (around the tubular structure, which if the scoopula is divided in half longitudinally, the scoopula may be laterally displaced one way or another to help with advancement of the device in tortuous vessels) or standalone rolling struts 25 incorporated, according to embodiments. Further, an external coating or membrane may be incorporated to stabilize the work element in its various working configurations.

Figure 19:
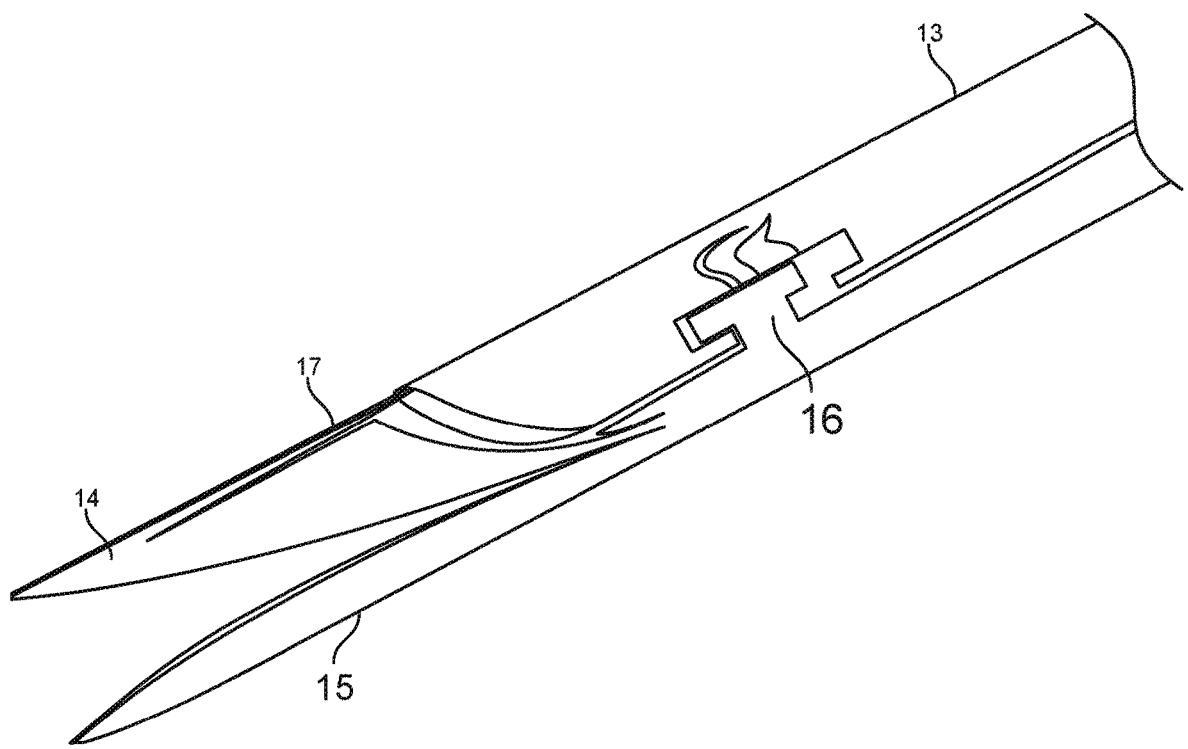
FIG. 19 shows a perspective view of a work element of a device, according to one embodiment.

FIG. 19 shows another perspective view of a monolithic, single tube work element 13 of device according to one embodiment, in an open configuration. In this view, it may be seen that the rolling strut 25 has been twisted as it is displaced, and the torsion load thus placed on it spreads the stresses imposed on the work element without allowing for any monolithic tube expansion at any point. In other words, any lengthening tendencies are minimized in favor of rolling to fill the available space. The lever arm forces cause the derived load to be divided, in conjunction with the void (space) that helps dictate the rolling strut motion. This action may effectively prevent any tendencies for work element expansion by directing the stress (spreading the load factor) and may be effective on its own without the presence of a travel limiting structure 16, working in concert with living hinge 17, for example, and according to one embodiment.

Figure 20A:
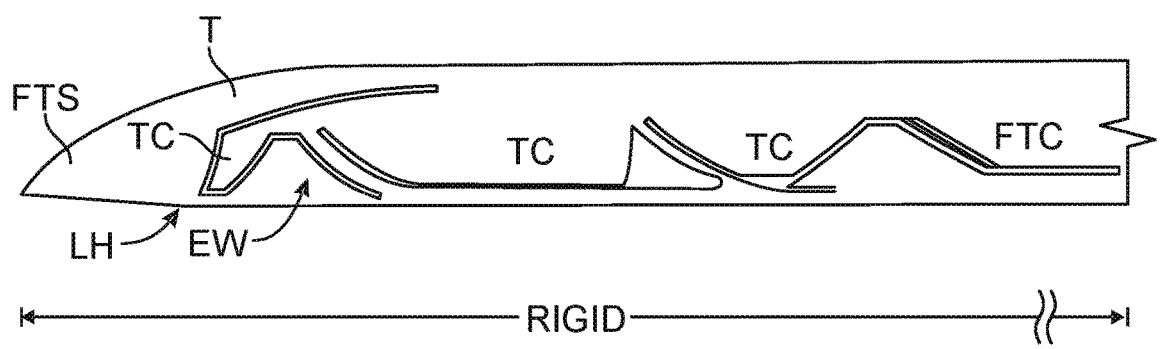
FIGS. 20A and 20B show side views of a work element of a device, according to one embodiment.
Figure 20B:
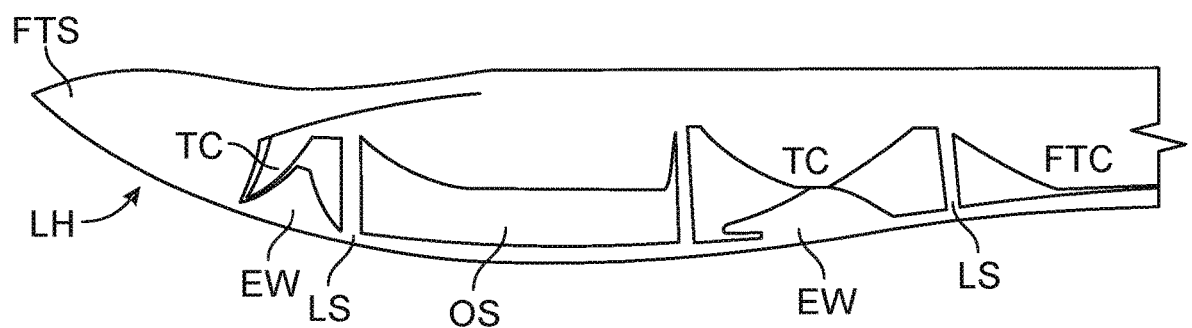

FIGS. 20A and 20B show side views of a monolithic work element of a device, according to one embodiment. As shown, this work element contains configurations that allow for lateral expansion of a supporting work element that has as its primary purpose to maintain its tubular geometry and selectively expose work areas or "exposure windows" external to it, for example, against an intima of a blood vessel, while containing any inner work element, such as a coring device, from escaping the inner lumen and perhaps causing damage to the intima layer. An internal coring or shaving element (not shown) must be presented to the wall of a blood vessel via the exposure windows created by this work element, which presses itself against the opposite wall of a vessel, thus pressing the exposed work area with opposite pressure, against the vessel plaque to be removed. This action also carries the supporting inner lumen of the work element towards the diseased wall (plaque), and this inner lumen, by way of remaining parts of the inner wall (not including the parts that press outward against the opposite wall of the vessel) constrains the introduced, separate coring element such that it too is forced against the diseased area. This apposition stabilizes the working element so that it can effectively remove the plaque and transport the tissue back proximally. As shown, part of the length of this work element may be more rigid, for efficiency of planning actions of an interior work element or device, and part of the length may be more flexible to allow for travel in the lumen of a blood vessel. FIG. 20A illustrates this work element with its beak or scoopula extremity in a relaxed position, and FIG. 20B illustrates a similar work element with its beak or scoopula extremity in a flexed position, which may provide further shielding downstream of the inner device, and prevent debris from being washed downstream in the vascular system. Both figures show adaptations of living hinges, tendons, a beak or scoopula terminus according to embodiments, and various apertures that allow lateral expansion and advantageously, flow in and around these structures, such expansion being controlled and contained by living strut elements, as shown. Flow areas and working areas are at least partially separated by remaining wall sections left behind (non-expanded) when flexible elements are expanded to reach across to the wall opposite the working window.

Figure 21A:
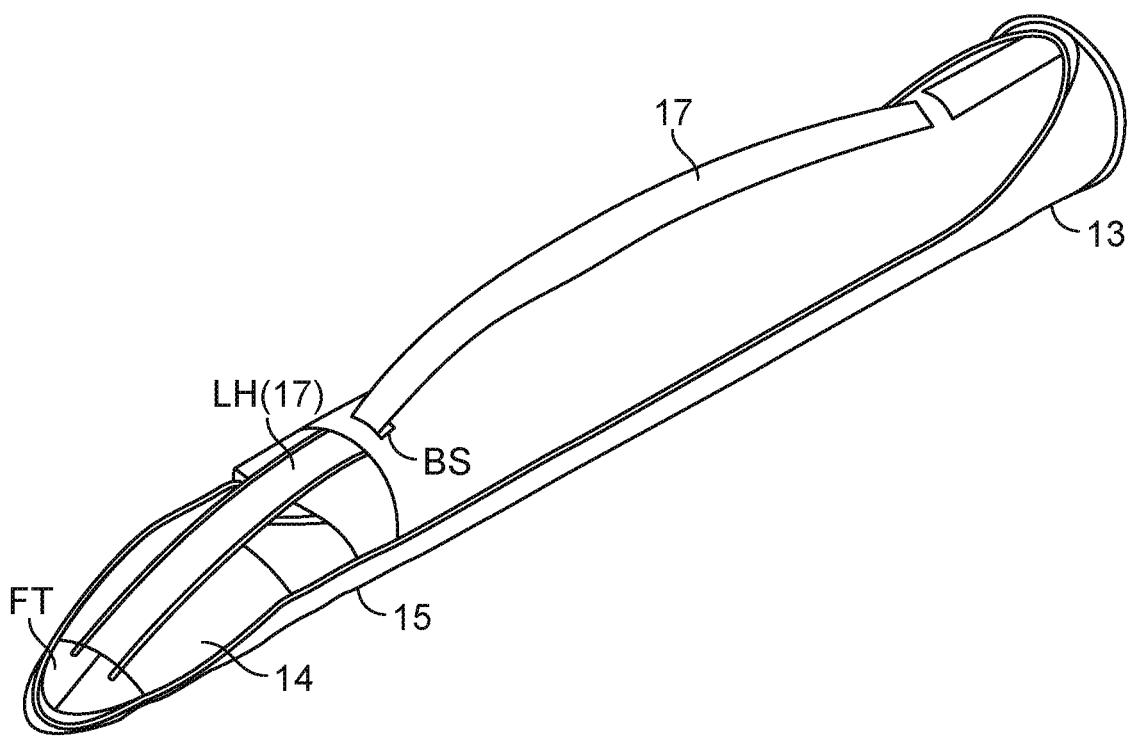
FIGS. 21A and 21B show top perspective views of a work element of a device, according to one embodiment.
Figure 21B:
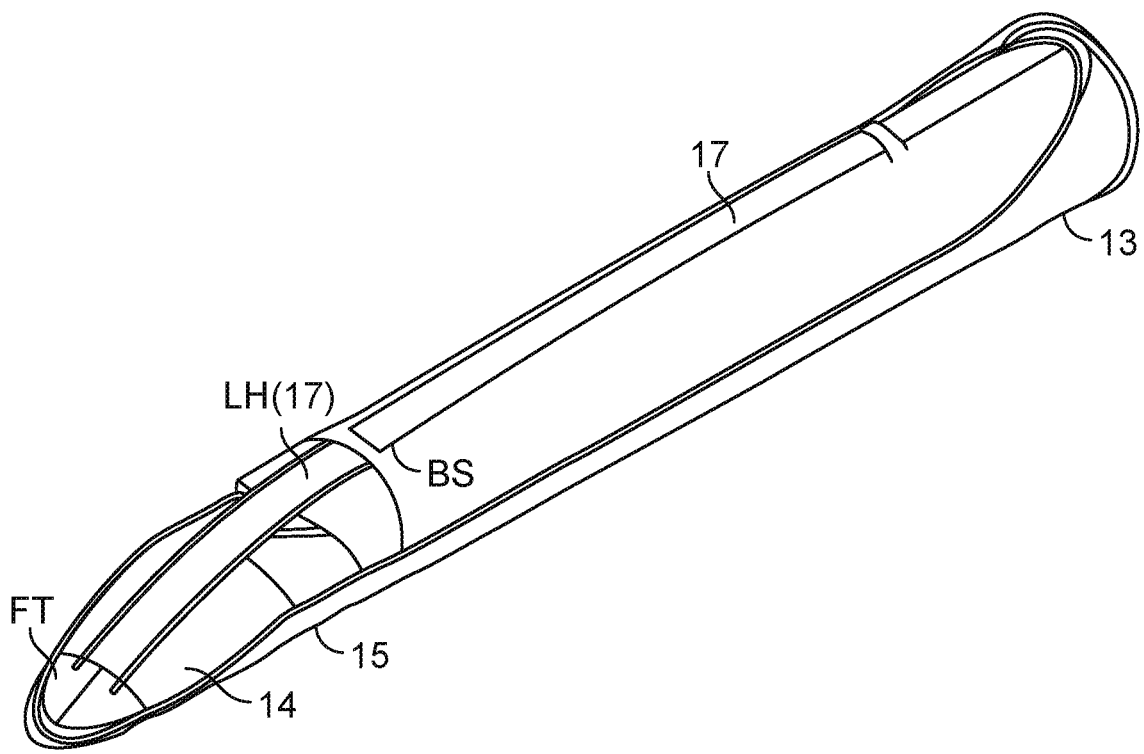

FIGS. 21A and 21B show top perspective views of a work element of a device, according to one embodiment. These views show an extended and flexible living hinge, configured as acting as lateral force mechanism, along the back of an internal work element operating inside a scoopula terminus outer tube, in this instance, a rigid external oscillating scoopula element. According to embodiments, if an internal coring device were to be introduced in the central lumen of this device, it would be forced against the open area of the scoopula to work on an external structure (cutting or shaving or coring). The outer tube scoopula may be rotated differentially to the inner work element to selectively expose work areas against a, for instance, vascular wall. As shown, the internal work element, used as a rotating cutting or coring element, will be forced against the material to be removed from a vascular wall while being constrained by the geometry of the open area of the scoopula of the outer tube. In FIG. 21B and according to one embodiment, the external oscillating rigid tipped scoopula may first be introduced over the lesion to be treated. Subsequently, the flexible work element may be introduced into its internal lumen, creating lateral force inside the outer tube against a work area exposed by the scoopula. Significantly, this configuration has the ability to establish or re-establish a blood flow channel around the complex work element shown herein, and simultaneously, as shown in FIG. 21B, to prevent or limit downstream ischemia.

Figure 22A:
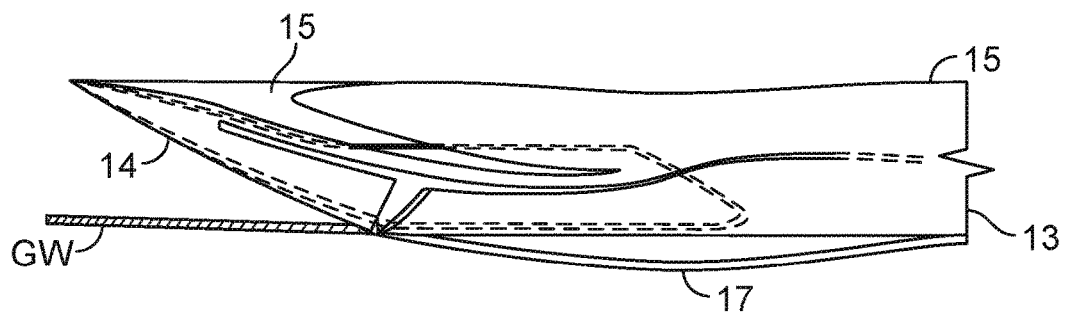
FIGS. 22A, 22B and 22C show side perspective views of a work element of a device, according to one embodiment.
Figure 22B:
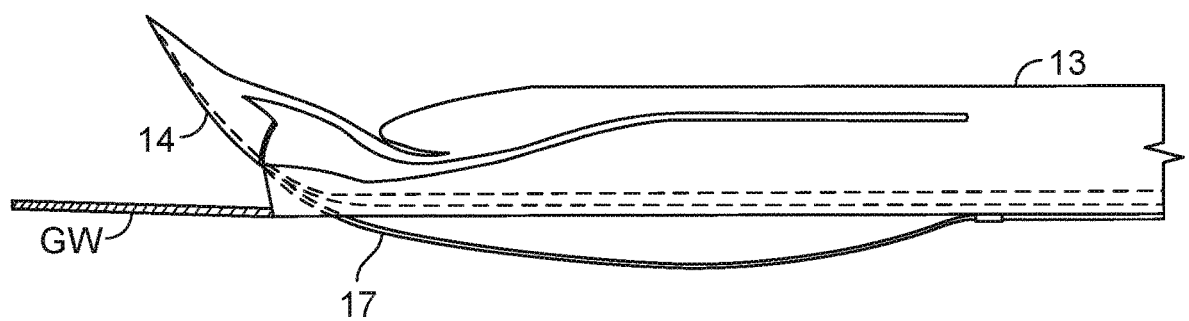
Figure 22C:
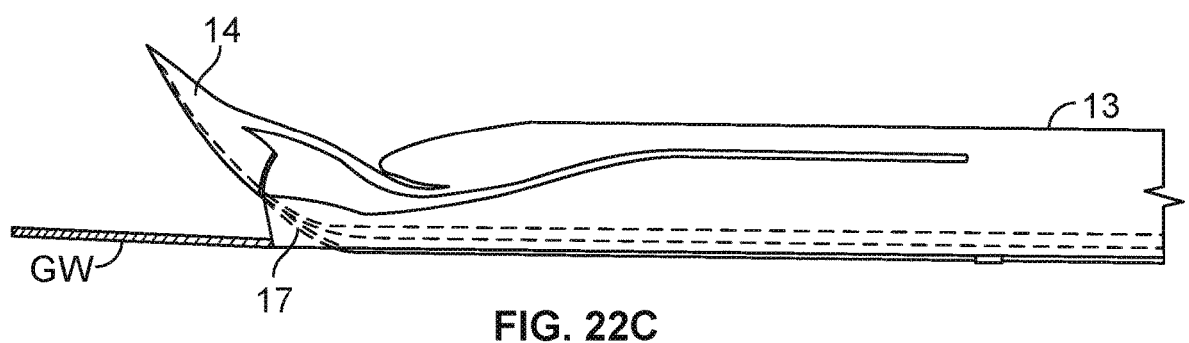

FIGS. 22A, 22B and 22C show side perspective views of a work element of a device, according to one embodiment. In these figures, a work element comprising an outer tube with a flexible, articulated beak or scoopula structure contains an inner tube element with fixed-beak differentially rotating, oscillating or energized scoopula terminus. Also shown in the figures are configurations in the outer tube comprising or defining channels, conduits to accommodate any of a variety of guide wires, which may contain provisions for boring, imaging, flow detecting, oscillating or transmission of any of a variety of energies, such as high frequency ultra-sound, pulsed ultra-sound, or radio-frequency energy, as examples. FIGS. 22A and 22B also show the lateral expansion function living hinge incorporated into this embodiment of a work element.

Figure 23A:
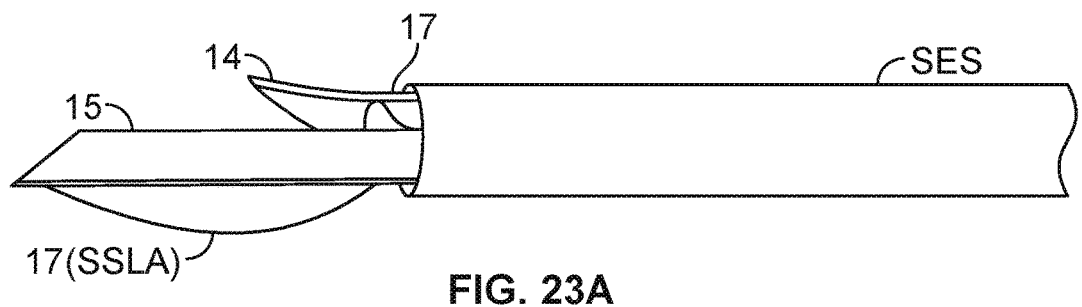
FIGS. 23A, 23B, 23C and 23D illustrate side views of a work element of a device in various stages of deployment, according to one embodiment.
Figure 23B:
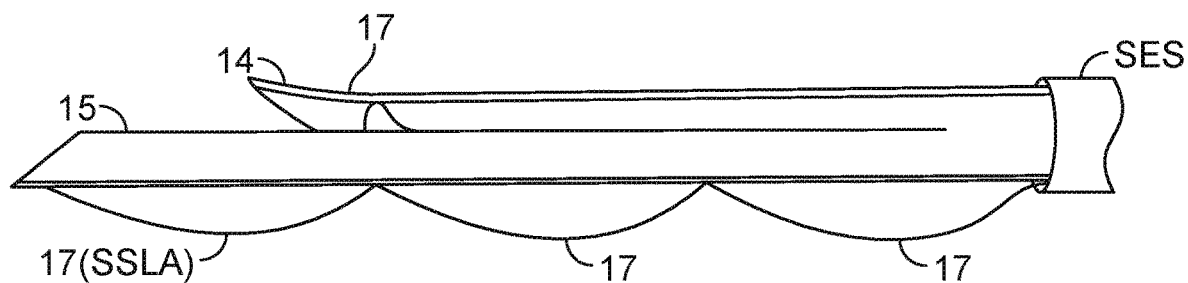
Figure 23C:
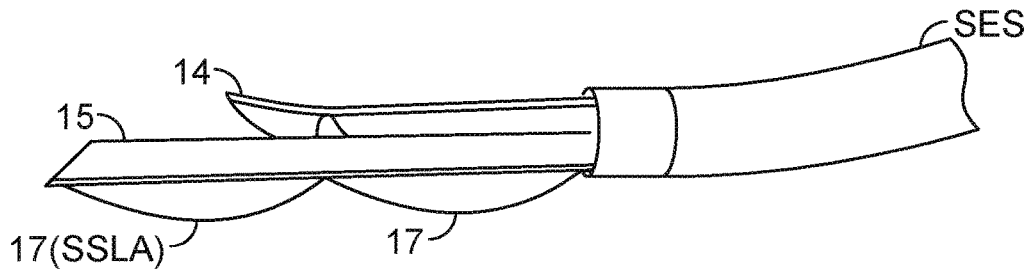
Figure 23D:
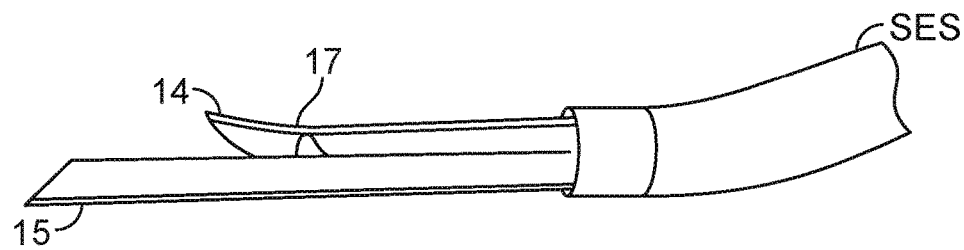

FIGS. 23A, 23B, 23C and 23D illustrate side views of three distinctive, separately controllable and introducible elements that function to create directional lateral (side-load application) force-generation, directional protection shielding and variable window working area exposure with isolation of the area provided by tubular side walls, according to embodiments. The first element may be a working beak or scoopula with a flexible beak element incorporated at its terminus (the latter in this example). The second element is a scoopula (in this case, one equipped with a non-articulating terminus) that is equipped with segmented, bowing side load applicators. These applicator bows may be actuated (bowed outwards) by mechanisms disclosed herein, exemplary mechanisms being embodiments illustrated in FIGS. 32A and 32B, and FIGS. 33A and B. The third element is a sliding exposure sleeve, which may, like the other two elements be configured to differentially rotate, oscillate or be otherwise energized for cutting purposes. Its main purpose is to control the exposure of the window while providing stability, variable rigidity and a "bumper" slider effect to prevent any unwanted vessel wall trauma that might otherwise occur if some of the sharp edges of other components were allowed to be exposed to vessel lining outside the desired work area. This element also serves to control the length of the more rigid working length as well as controlling the length of exposure of side-load applicators (bowing members). Lastly, this sliding exposure control can be used to control the vacuum area and to help internalize excised tissue for transport proximally. In FIG. 23A, the sliding exposure sleeve (SES) element is shown allowing exposure of only one segment of the side-load applicators (SSLA) and also a relatively short open window area. In this figure, the articulated scoopula is shown just emerging from under the SES in an overdriven open state. At this stage it may be rotating, oscillating etc., in order to shave off exposed plaque, using the sharp sidewalls of the scoopula to maximize its cutting efficiency while working in an isolated area (by the tubular walls of the external scoopula and the SES). At the end of its distal translation, its flexible beak will be flexed against the external scoopula and part off of the now completely excised tissue will be transported back proximally in the device as a whole. FIG. 23B shows another scenario where there is maximal window length and exposure due to the SES being retracted proximally, along with maximum support along the entire open window of the non-articulated beak external scoopula. The inner articulated-beak scoopula is again seen in overdriven open configuration and would be more than ⅔d along its translation, nearing its parting-off position (not shown in any of these figures). FIG. 23C shows an intermediate exposure while FIG. 23D shows that the SSLA's and the SES are independently controllable, because while the SES exposes enough window length to allow two SSLA's to be deployed, in this case there may be a desire to limit the sideward pressure, perhaps due to the available vessel diameter at that point being large enough only to accommodate the un-expanded working elements.

Figure 24A:
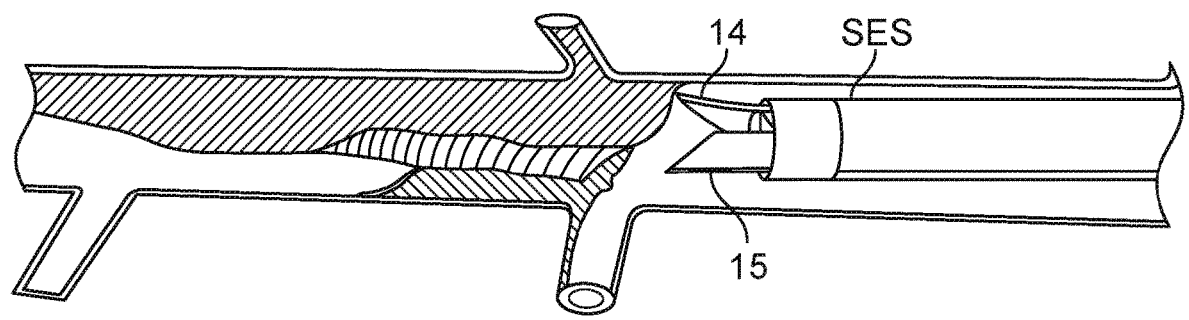
FIGS. 24A and 24B show a work element of a device inside a vascular structure, according to one embodiment.
Figure 24B:
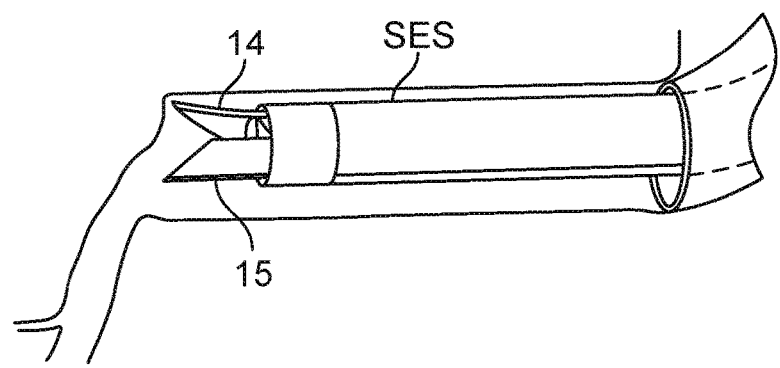

FIGS. 24A and 24B show a work element of a device inside a vascular structure, according to one embodiment. FIG. 24A shows a side view of a vessel completely occluded by elements of hard plaque and a nearly central area consisting of organized thrombus, a major side branch that is still widely paten and additional branches beyond the area of total main vessel occlusion that are now receiving no antegrade flow. Everything beyond the area of complete occlusion (chronic total occlusion or CTO) with thrombus is not visible on angiography, which depends on contrast filling to visualize a lumen. These pieces of information would be available by other imaging modalities however such as optical coherence tomography (OCT) and intravascular ultrasound (IVUS) for example. This figure shows a device combination according to embodiments and as shown in FIG. 23, in place proximal to the area of total occlusion as well as the major, patent side branch. FIG. 24B depicts the information typically available with angiography and again, the combination device of FIG. 23. In this figure a guiding catheter is shown in the ostium or opening of the main artery, through which the combination devices are introduced.

Figure 25A:
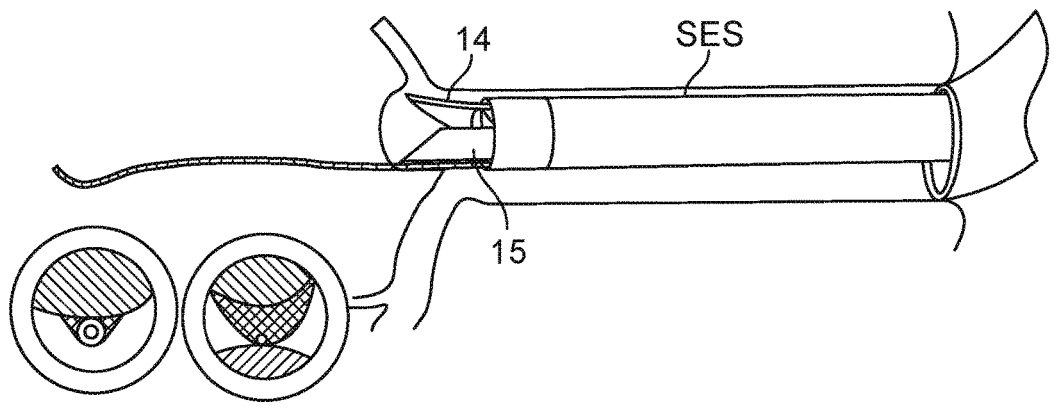
FIGS. 25A, 25B and 25C show a work element of a device inside a vascular structure and details thereof, according to one embodiment.
Figure 25B:
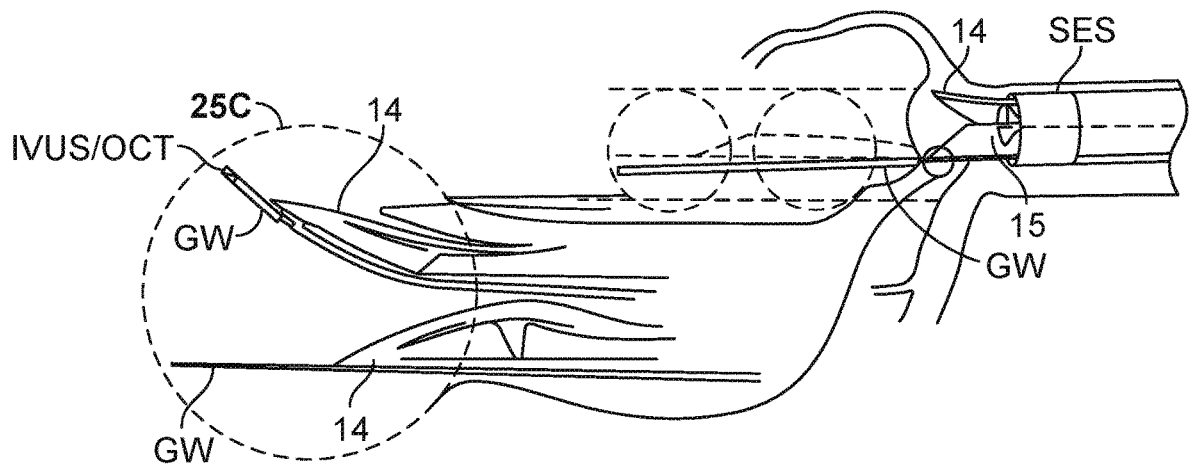
Figure 25C:
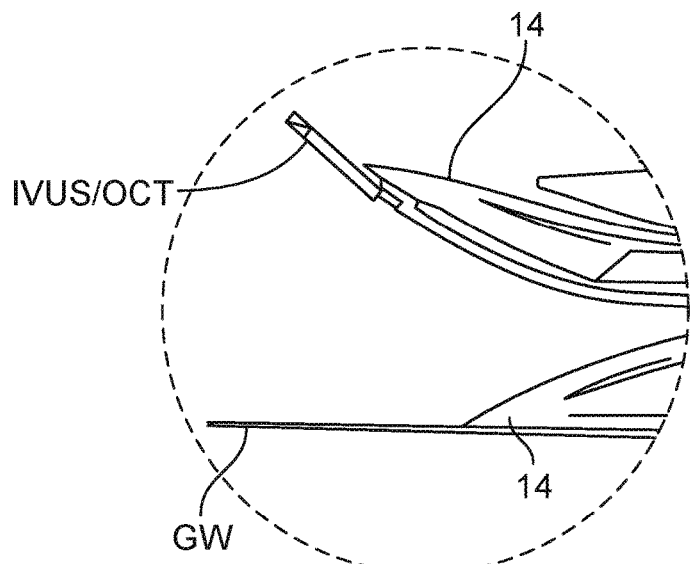

FIGS. 25A, 25B and 25C show a work element of a device inside a vascular structure and details thereof, according to one embodiment. FIG. 25A is an angiographic representation of a first stage of intervention on this CTO. The device elements of FIG. 23 are used to bore ahead by differential rotation of the two scoopula elements, a short safe distance to break down a hard cap of the lesion, exposing a softer portion of organized thrombus. Once a softer area has been thus exposed, a guiding element, which could simply be a steerable floppy-tipped wire, a hydrophilic-coated guide wire, an imaging wire, a gently rotated boring wire or high speed burr wire, can be carefully advanced into this softer center distally. FIG. 25B shows two representations of information that may be displayed by IVUS or OCT as an area distally within and beyond the area of CTO. These depictions show that there is mature plaque replacing healthy intimal vessel lining occupying more than half the circumference of the vessel wall in the initial image within the CTO, and includes organized thrombus nearly (at this level) completing the CTO in the center of the vessel. In the image obtained more distally, there is no significant thrombus and at this more distal stage, the plaque is confined to the upper approximately ½ of the vessel circumference. At this stage, a plan can be made to serially, safely and minimally traumatically deal with each of these abnormalities, using each of the components of a device of FIG. 23 in a logical sequence. FIG. 25C shows a releasing clip element along the back side of a flexible beak element to direct a guidewire, imaging wire or other suitably sized device. The clip element may be used to pick up a wire or tubular element by twisting the device with its beak towards the wire element for example and when desired, the wire element may be released by twisting the beak in the opposite direction as desired. Not depicted is that the living hinge can tighten down on the guidewire element during flexion of the beak to securely hold it in place, then slightly free up the element to enable it to be translated or rotated as desired by relaxation of the beak, for example.

Figure 26A:
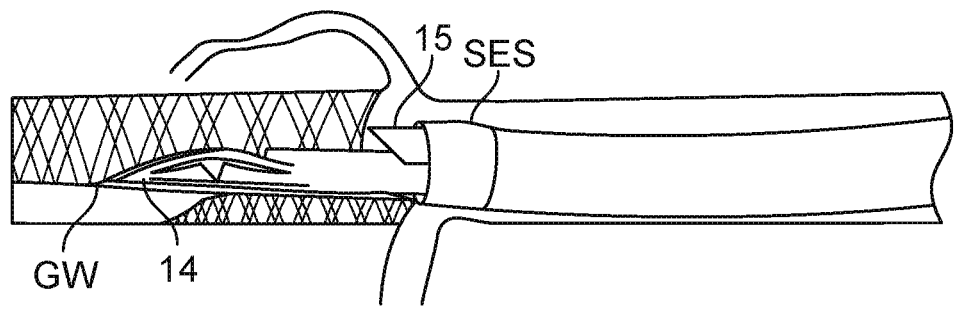
FIGS. 26A and 26B show a work element of a device in stages of deployment inside a vascular structure, according to one embodiment.
Figure 26B:
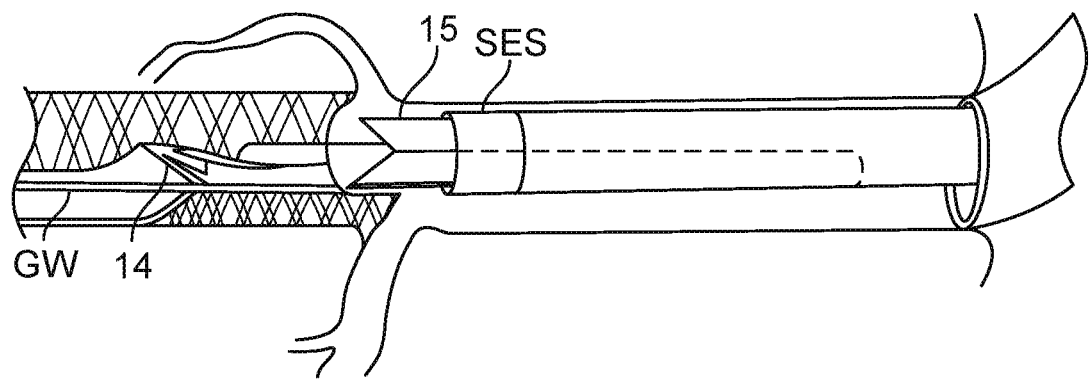

FIGS. 26A and 26B show a work element of a device in stages of deployment inside a vascular structure, according to one embodiment. FIG. 26A shows the advancement of the articulating beak scoopula of FIG. 23 to a position at the end of the organized thrombus depicted by the imaging guidewire introduced and positioned as in FIG. 24. The imaging element is shown released from the beak in FIG. 26B and at this stage, the beak of the articulating-beak scoopula is flexed at the distal end of the organized clot (thrombus), protecting distal vessels from occlusion by any released debris that may otherwise move downstream. Once isolated in this manner, any number of interventions may be used depending on the state of the thrombus, i.e., whether it is well organized and difficult to solubilize or not. If it is relatively soft, one of the devices introduced earlier (hydro-dissection, flush/vacuum for example) may be introduced within the articulating beak scoopula to extract the thrombus, however if it is already harder, then another method as shown in subsequent figures may be employed. Note, the degree to which the SES may be advanced in the area of the major side branch may be determined by flows but if possible, for maximal protection of the ostium (opening) of this vessel, the SES is shown with its soft collar placed over the opening to protect its ostium from trauma caused by maneuvers involving the articulating beak scoopula and guiding element. In this position, the major side branch may also be protected from vacuum forces applied via the SES to help transport thrombus and plaque debris proximally.

Figure 27A:
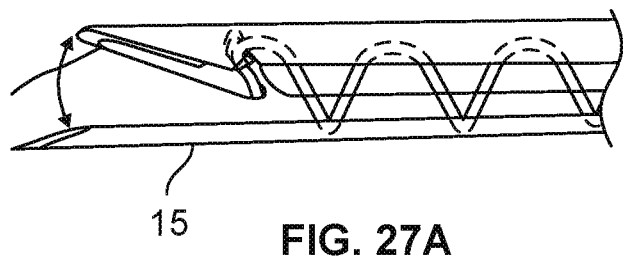
FIGS. 27A, 27B and 27C show details of a work element inside a vascular structure, according to one embodiment.
Figure 27B:
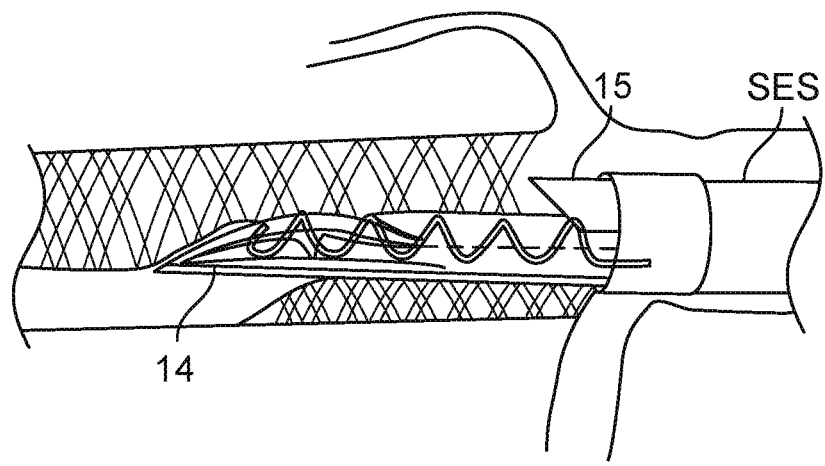
Figure 27C:
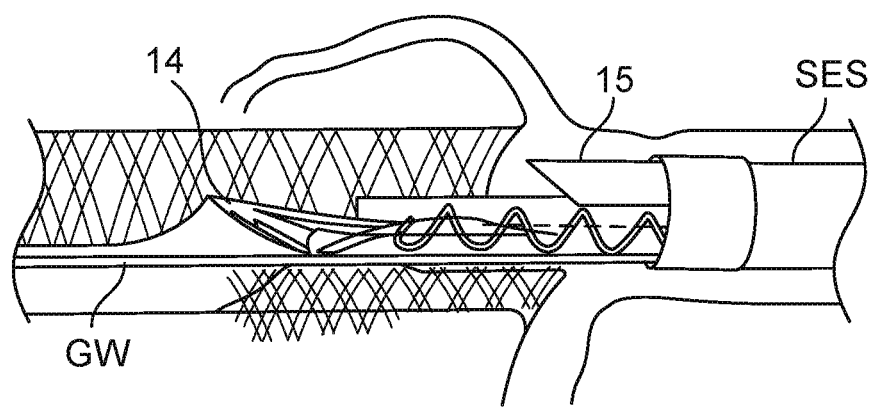

FIGS. 27A, 27B and 27C show details of a work element inside a vascular structure, according to one embodiment. FIG. 27A shows another embodiment of a scoopula in this case equipped with a soft beak that is freely extendable/flexible by virtue of its attachment around the distal end of a helical structure, which is terminated in an axle structure about which the soft beak element may swivel to be more or less flexed. This action enables it by centrifugal force to gently trace a path along a wall or plaque of a vessel while clearing thrombus, which, once freed from these wall structures may be kept solubilized and transported proximally by the action of the helical element or elements, together with swirl action of flush and vacuum through the internal lumen(s). In this case, this specialized device may be introduced inside the articulating beak scoopula in place temporarily of the external non-articulating beak scoopula. This device is shown in action in the vessel in FIG. 27B as it gently frees the thrombus up for proximal transport. FIG. 27C shows that this device may be retracted proximally to a point where it is fully contained within the SES or more proximally, even all the way out of the field together with any remaining adherent thrombus that may not have been fully transported out previously.

Figure 28A:
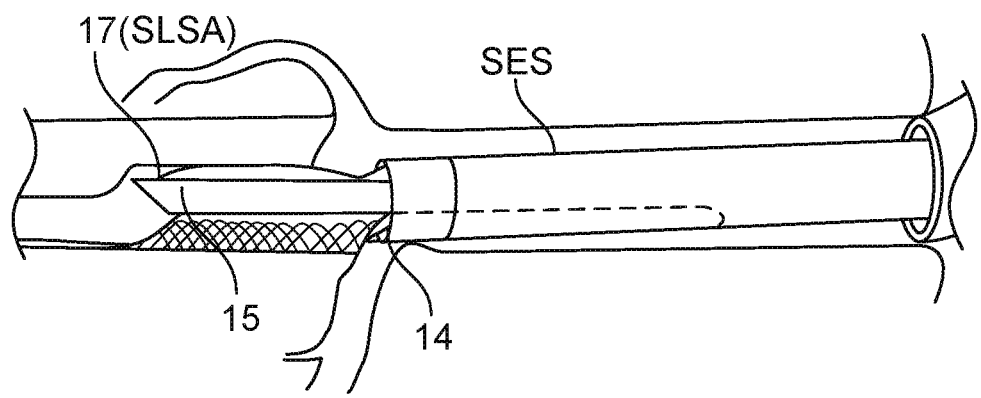
FIGS. 28A and 28B show details of a work element inside a vascular structure, according to one embodiment.
Figure 28B:
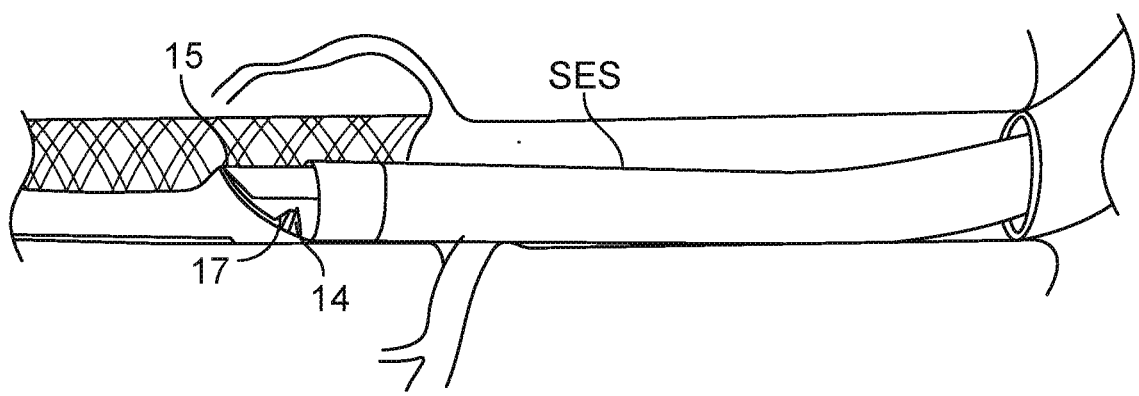

FIGS. 28A and 28B show details of a work element inside a vascular structure, according to one embodiment. FIG. 28A shows the next stage of a procedure where by a non-articulating scoopula with SSLA's is reintroduced and desired, precise levels of directional side force and lateral dimension distances are applied so that a working, articulating-beak scoopula may be advanced distally with differential rotation, oscillation or other energy delivery to shave hard plaque at a precisely determined and stabilized depth. This may be done with imaging, which imaging may be incorporated in an imaging version of an articulating beak scoopula, or alternatively, an imaging element may be incorporated in the non-articulating, supporting scoopula, to monitor depth and progress of the intervention. FIG. 28B shows a completed cut and part-off in this case using a short radius embodiment, and removing virtually all or most of the diseased wall of the vessel on that (working) side, leaving a smooth surface behind for optimum healing. This figure also shows the SES advanced distally with and just proximal to the cutting scoopula, relieving the side pressure as it goes along to disengage the cutting scoopula and help prevent inadvertent deep cutting distally, given a possible tendency for the non-articulating scoopula to "follow" the taper of the vessel potentially causing a deep dive planning action. In this way, the SES acts as a protective bumper element, to lift the cutting scoopula away from the vessel lining. The precise depth may be thus protected to an even greater extent than might be possible if reliant on imaging and SSLA forces alone.

Figure 29:
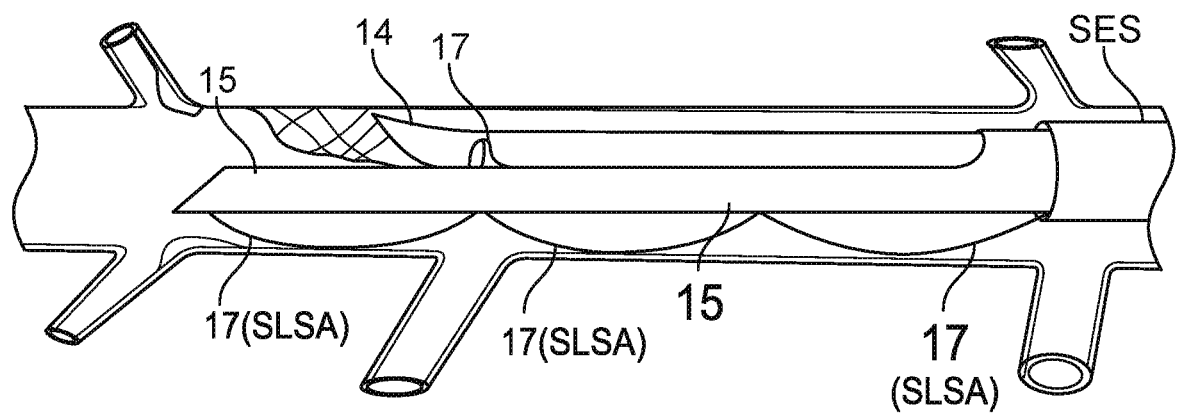
FIG. 29 shows details of a work element of a device inside a vascular structure, according to one embodiment.

FIG. 29 shows details of a work element of a device inside a vascular structure, according to one embodiment. FIG. 29 shows a final interventional step, which may be the only step needed were it not for the initial presentation being a CTO (complex, chronic total occlusion with organized thrombus). If this were a simple stenosis for example, the devices of FIG. 23 could be introduced into this position over a suitable guide wire, or more favorably, over an IVUS wire or iFR wire. If over an iFR wire, the particular configuration of the present embodiments may be especially favorable by not limiting flow during measurements and to allow continuous flow during intervention by way of the open-ness of the segmented side load applicators (SSLA's), thus permitting intra-procedure monitoring of flow improvement as well. Shown here is that the SSLA's as opposed to traditional balloon elements are both directional and non-occlusive, permitting continuous non-ischemic interventions. Additionally, these elements can be selectively deployed and positioned, such that ostia of major side branches advantageously remain unobstructed during the interventional procedure, again, preventing lack of nutrition and oxygenation that may lead to downfield ischemia. In this case the aperture- and force-controlling sliding exposure sleeve (SES) is not advanced since the plaque is located along a straight segment of the vessel, however if depth control were trending unfavorable, the SES could be called upon to recover the shallowness of cutting at any time. In this case the SES is left proximally in an un-needed position to enable maximum flow into side branches and downstream in the main vessel.

Figure 30A:
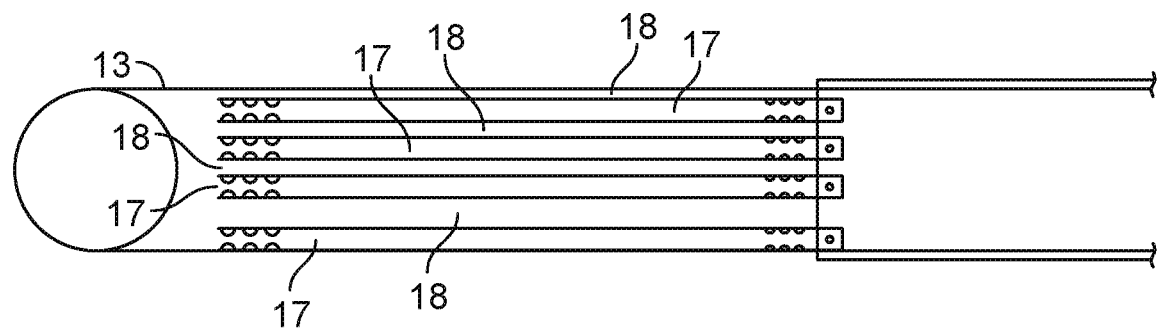
FIGS. 30A and 30B show side views of an expandable work element, according to one embodiment.
Figure 30B:
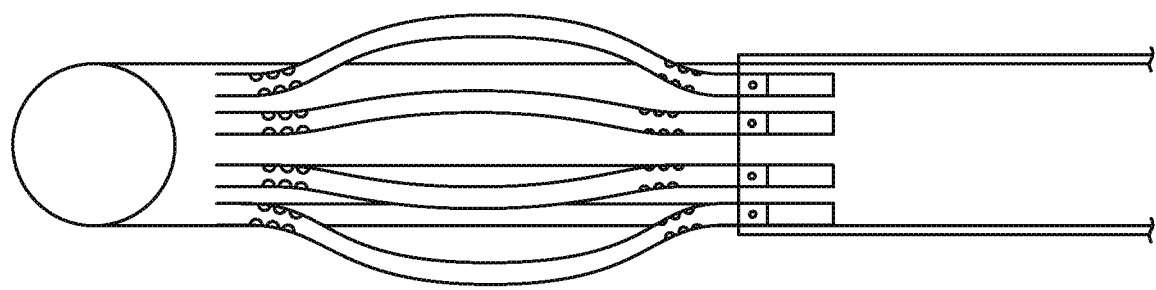

FIGS. 30A and 30B illustrate side views of an expandable work element, according to one embodiment. As shown, such a work element 13 may incorporate a plurality of living hinges 17 and tendons 18 (alternating, in this view) with or without a terminal beak or scoopula element or elements (without, in this view). These hinges 17 and tendons 18 may comprise part of the single monolithic structure defined by cuts effected by laser cutting, for example. As shown, an outer flexible tube may be attached to the work element, such as to the proximal end of each living hinge element, or a collar actuation mechanism, as shown in FIG. 32B below. Other actuation mechanism may be configured to place an axial distal force on the living hinges relative to the tendons, to force the living hinges to expand laterally or circumferentially as shown in FIG. 30B. Work elements, according to embodiments, may comprise any combination and number of living hinges, beaks, scoopulas, tendons or collars. Moreover, outer tubes or other features may be coupled or attached to structures of such work elements. All such combinations are, therefore, considered within the scope of the present disclosure, and each such combination may be specifically configured to accomplish specific work tasks at different phases of an intra-vascular intervention.

At times, living hinges may function as tendons and tendons may function as living hinges. Accordingly, the delineation of living hinge versus tendon may be fluid, depending on the intended function of a particular element, which may change as it is being actuated. In this illustration, a number of adjacent living hinges and tendons are disposed around the circumference of a single tube, such as a laser-cut hypo-tube, and the distal terminus or free end of the work element is configured without beak or scoopula features. However, the distal terminus may incorporate such distal features as castellations or circumferential sinusoidal wave shapes, according to embodiments. Such a work element may also feature additional lateral cuts or shapes at the distal-most and proximal-most ends of each living hinge, or along its length, which may influence the shape assumed by the living hinges as they expand outwardly as a result of proximal force applied to the tendons. Such shapes associated with the living hinges may be different from living hinge to living hinge to cause certain living hinges arranged around the circumference of the work element to assume a particular shape while other living hinges may be induced into asymmetric shapes, as a result of their individual conformations, according to embodiments. Such shapes may include elongated ovals (or tapered right cylinders, for example) and, as illustrated in FIG. 30B, assume a bulbous shape at the distal or proximal end of the expanded work element. Other variations are possible and all such combinations of such shapes are considered within the scope of the present disclosure. Such a work element may be configured to allow for a guide wire, for example, to be passed within its central lumen at the edge of a vascular obstruction, and successive expansion and deflation of the work element may be imposed to gently separate the occlusion from the vascular wall in successive stages to allow such a guide wire or other introduced work element to advance between the intima and the obstruction, which may also maintain or re-establish blood flow around an obstruction. Such a work element may also be used itself as a temporary stent, advantageously permitting maximal distal flow, as opposed to traditional expanding balloon devices, which in the very best of cases permit only a fraction of normal flows, or to expand a stent placed at its distal terminus inside a vascular structure, or may serve, for example with a perforated cap as its own terminus as a debris screen to catch dislodged debris from another work element. According to another embodiment, distal finger elements configured as free portions of the distal end of living hinges and between adjacent living hinges and tendons may expand outward upon actuation, and serve as an umbrella like screen at the distal end of the work element. Another capability of such a work element may include expansion against the walls of the inner lumen of a vascular structure, and with rotation, to act as a burr-like terminus to gently shave material from the vascular wall as it is progressed forward, according to one embodiment.

Figure 31A:
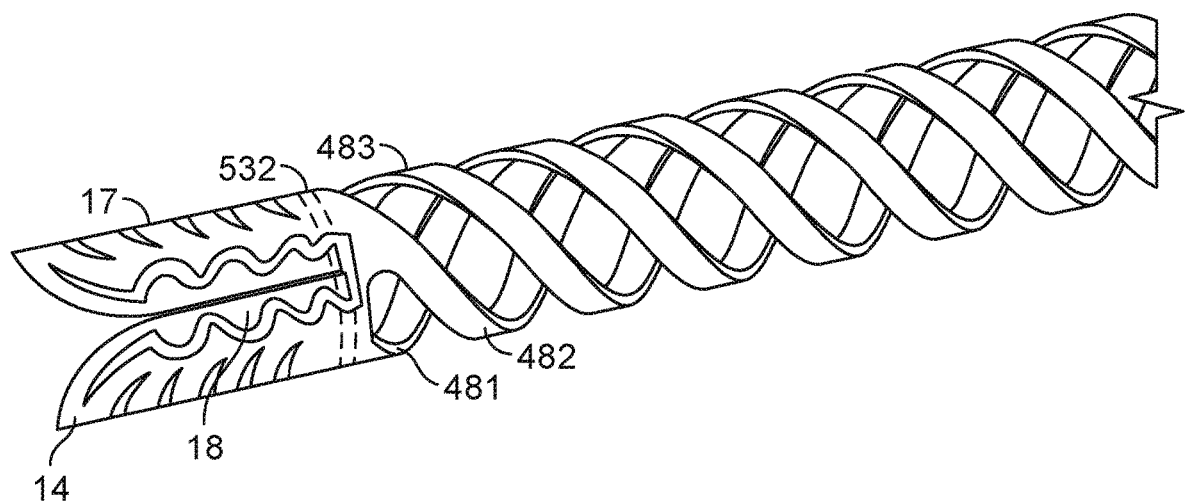
FIG. 31A shows a side view and FIG. 31B shows a top view of a work element of a device, according to one embodiment.
Figure 31B:
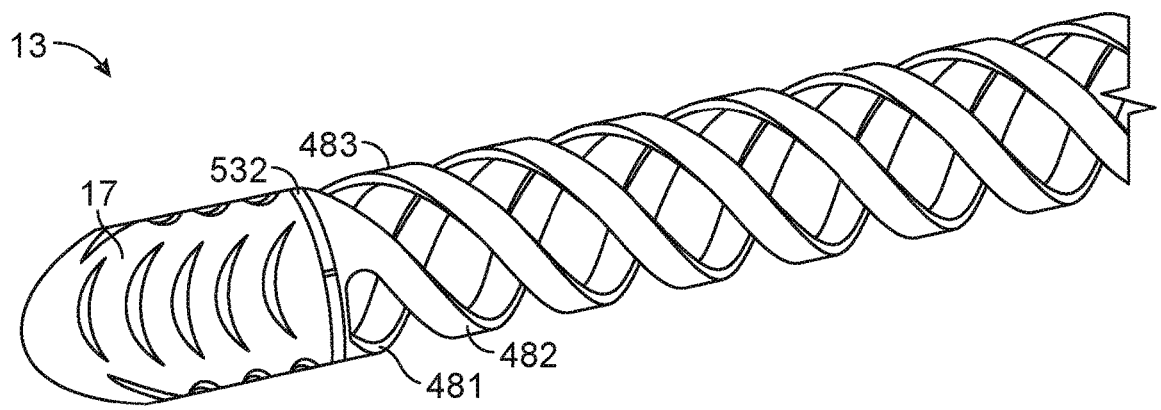

FIG. 31A shows a side view and FIG. 31B shows a top view of a work element of a device according to one embodiment. In this view, it may be seen that the individual elements of living hinge(s) 17, beak(s) 14 and tendon(s) 18 may be monolithically formed from a single tube by cuts defining the respective elements. Thus, forming a work element may be an entirely subtractive process (i.e., removing material therefrom), according to one embodiment. In other embodiments one or more processes used to form a work element may be other than purely subtractive. In any event, in this illustration, twin beaks are shown, but combinations of one or two or more opposing fixed or articulable beaks or scoopulas or a combination thereof are possible in other implementations. Of note also is that the sinusoidal wave-shaped kerfs or laser cuts for the living hinge 17 and tendons 18 are the same, and therefore the living hinges and tendons are directly adjacent to each other. The tip 14 is merely an extension of the living hinge area as defined by the cuts. As such, the delineation between beak, living hinge and tendon is not exact, as one structure may flow seamlessly into another or other structure. Therefore, the beaks, tendons and living hinges may be more accurately defined as areas or portions of a monolithic (i.e., single piece) structure, and such overlap between adjacent functional areas may allow for additional flexibility to be built in to the very distal end of the work element 13. Indeed, if the bilateral tendons 18 are both pulled simultaneously with a proximally-directed force, the beak tips will deflect towards the central lumen of the work element, as shown in other figures. If one tendon corresponding to a beak is pulled proximally, and the other is held stationary or pushed distally, then lateral flexion of the distal end of the work element will result. If one set of tendons only, corresponding to one beak of a work element of opposing beaks, for example, is pulled axially, that beak will tend to force an opposite beak to conform to such opposite flexion, allowing the work element to dive or divert vertically towards a lower spot that may be encountered in a vascular structure, according to another embodiment. With such configurations and controls, the work element may thus be advanced distally inside a vascular structure. A work element so configured and controlled, also possesses the ability to flex laterally or vertically. Moreover, rotating the work element itself on its long axis allows for gentle forward movement or penetration while following natural curves as opposed to resisting them in such a vascular structure. Such a work element may also be foreshortened considerably, as shown in these figures, in ratio of work element length to its inside diameter, to allow for a very compact work element structure at the end of a long, flexible body portion, shown as helical elements 481, 482 and 483, according to embodiments.

Figure 32A:
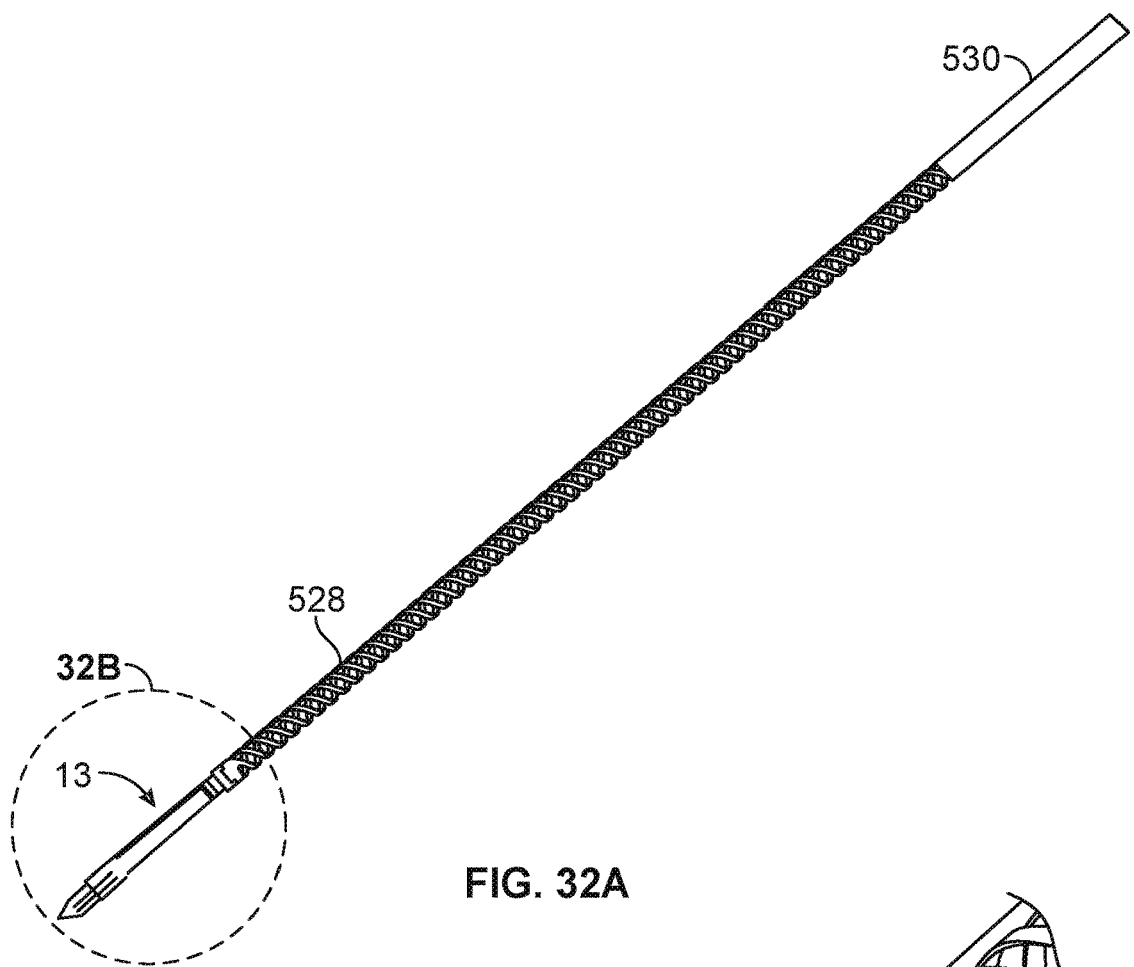
FIGS. 32A and 32B illustrate details of a collar actuation mechanism of a work element of a device, according to one embodiment.
Figure 32B:
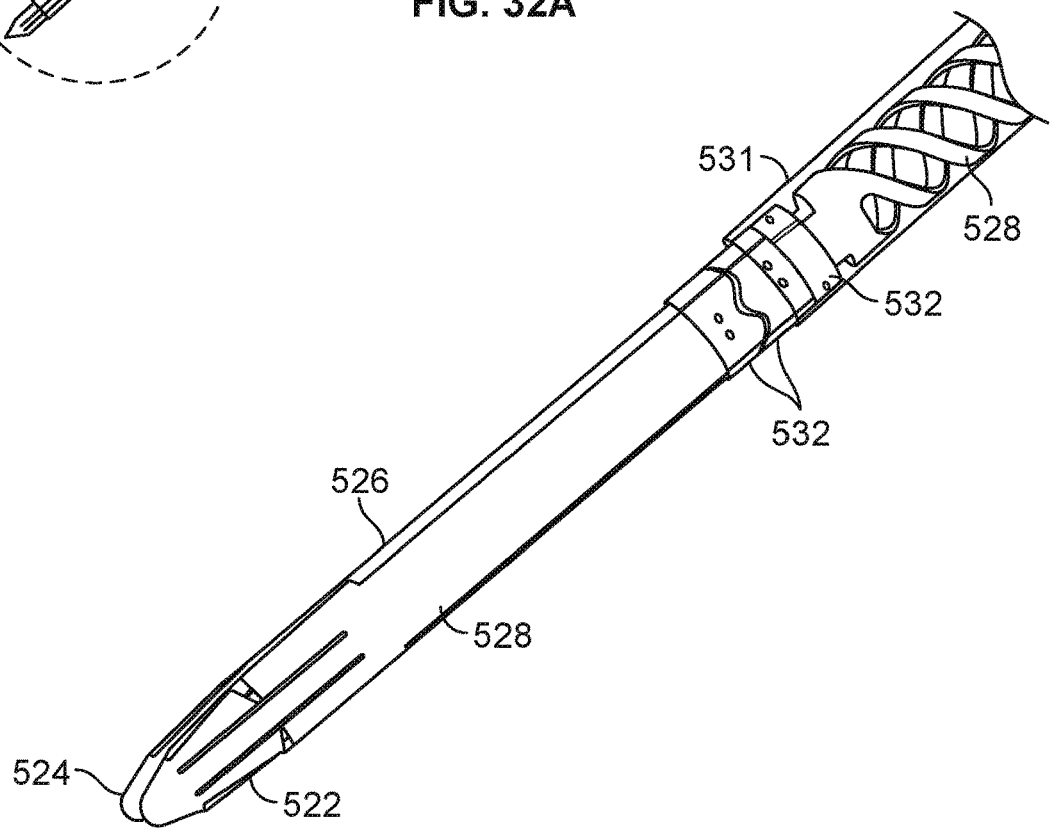

FIGS. 32A and 32B illustrate details of a collar 532 actuation mechanism of a monolithic work element of a device according to one embodiment. Such a collar may be attached to a tendon actuation tab 526, as well as a body portion 528 of a work element, and provides for differential axial movement of a tendon 522, for example, in relation to a body portion 528 of a work element 13, thus allowing for beak actuation. In this figure, a collar 532 may be comprised of three sub-elements, the most distal of which may be attached to, for example, a body portion 528 of a work element, the middle collar attached to a co-axially placed outer tube 531, and the most proximal collar attached to the tendon actuation tab 526. If the outer tube is rotated, the sinusoidal wave around the periphery of the adjacent-most distal collar and middle collar will provide relative axial motion between the body portion 528 of the work element and the tendon actuation tab 526 of the work element, thus actuating the beak tip(s) without allowing the beak tips to twist in relation to one another. Such a configuration may be advantageous in allowing for beak actuation wherein the proximally extended body portion 530 of the inner monolithic work element tube may be, for example, over 3 feet in length and flexible over its length as may commonly be associated with vascular intervention devices. An outer tube 531, also flexible in construction (such as shown in FIG. 32A by the helical structure, but with an opposite twist, for example), would therefore still efficiently translate rotation along its entire length in relation to the inner work element flexible body portion, allowing efficient remote actuation of the work element at its distal end.

Figure 33A:
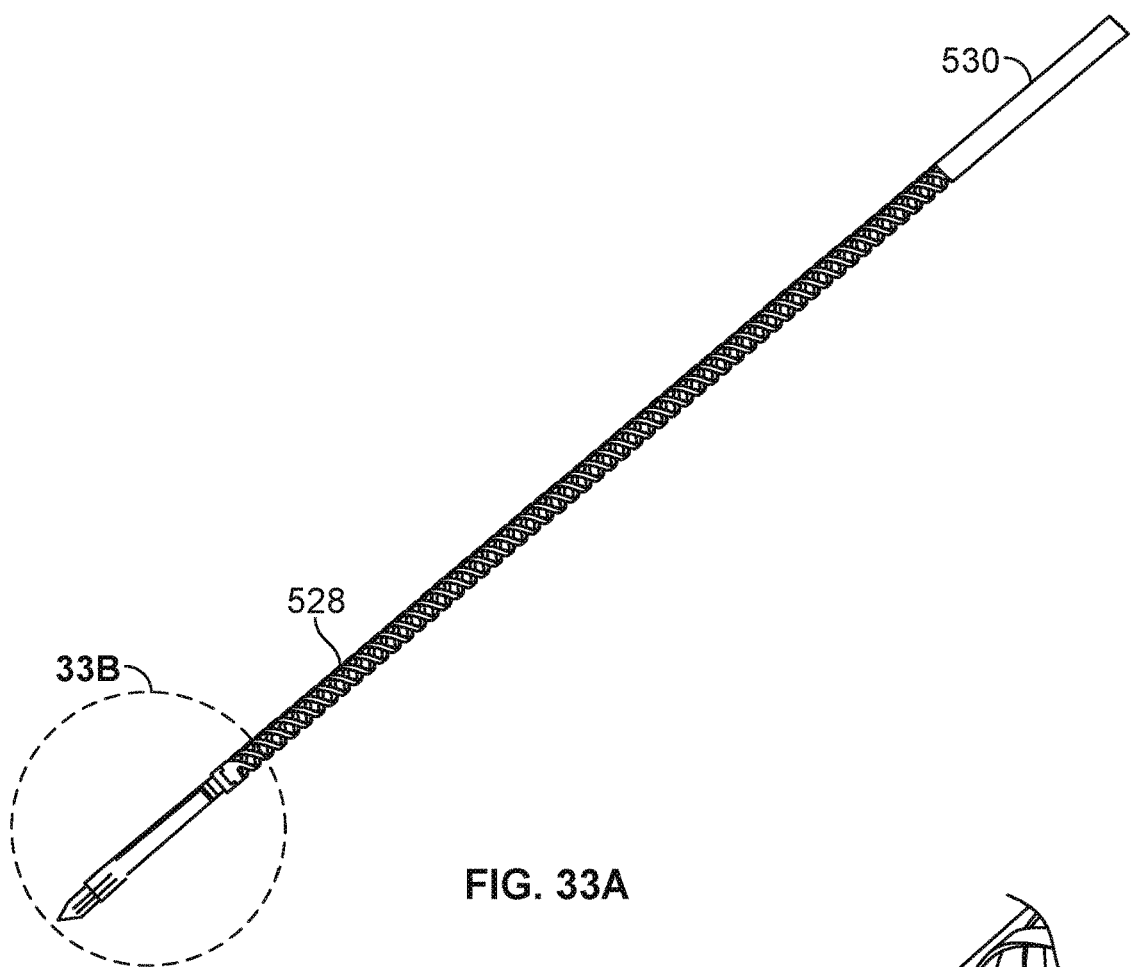
FIGS. 33A and 33B show elements and features of a single flexible tube work element with double articulable beaks or scoopulas, according to embodiments.
Figure 33B:
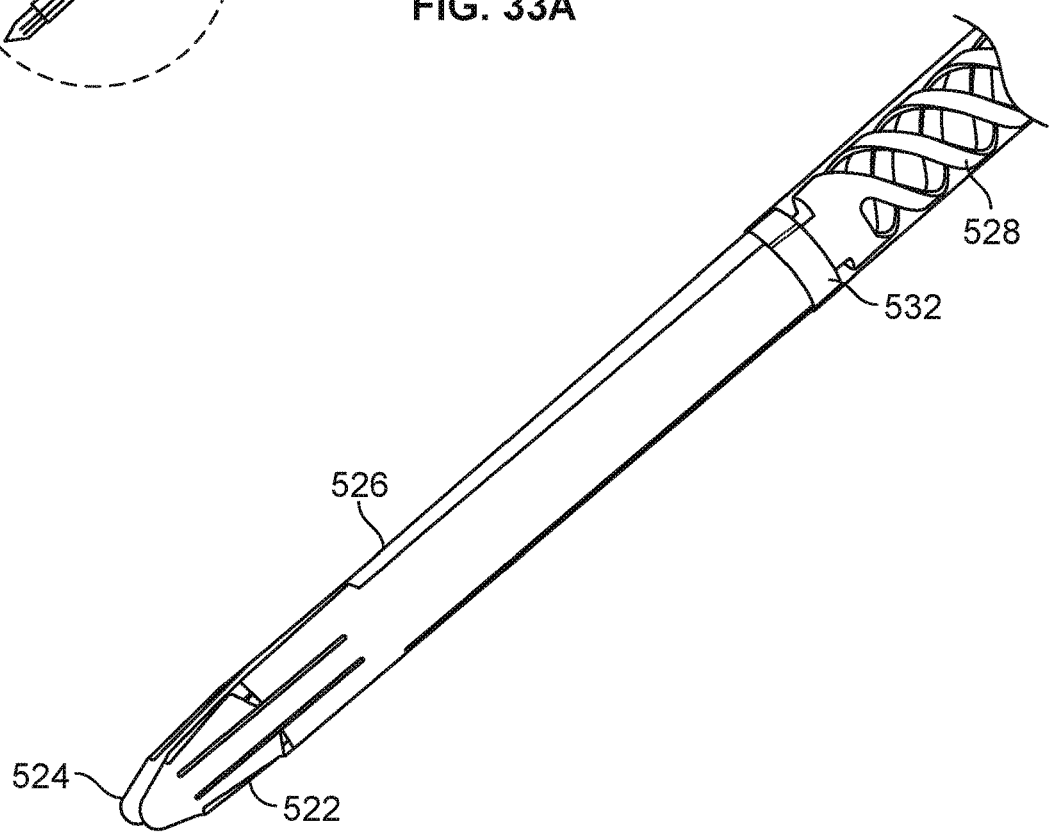

FIGS. 33A and 33B show features and elements of a single monolithic tube 530 of a work element, which may comprise at its distal terminus one or more fixed or articulable beaks or scoopulas, or any combination of the above, according to various embodiments. In one embodiment, a work element is comprised of a single tube 530, which may have a flexible portion 528 or portions disposed along its axial length. In FIG. 33B, details of the distal end of a work element may be seen, with beak or scoopula tip(s) 524, tendon(s) 522, tendon actuation tab(s) 526, a collar element 532 fixed to the tendon actuation tab(s) 526, and a flexible tube portion 528, which may be coated to maintain liquids within its central lumen while remaining flexible. As shown, a proximally-directed force applied to collar 532 while maintaining the body portion 530 fixed would tend to close the beak(s) or scoopula(s) (cause them to flex towards the longitudinal axis of the work element).

Figure 34:
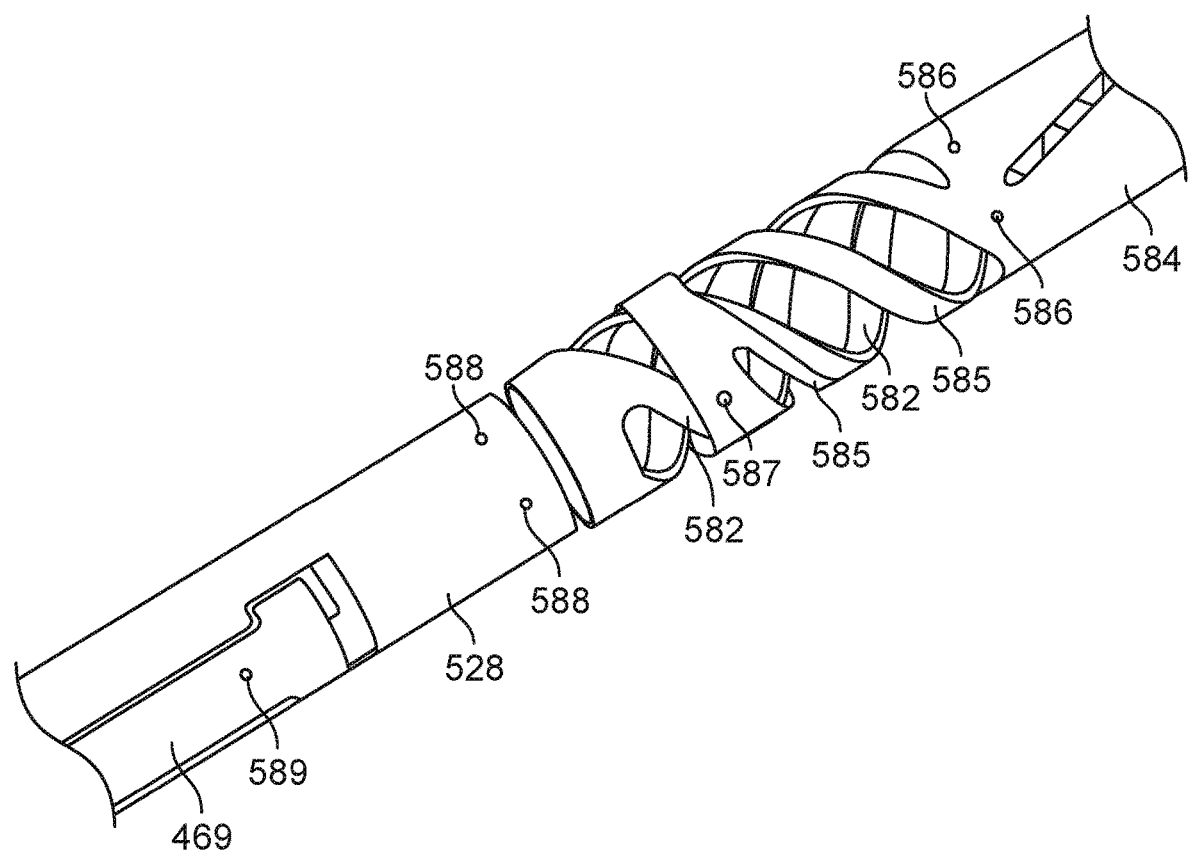
FIG. 34 shows elements of a double tube work element proximal end, according to one embodiment.

FIG. 34 is a side perspective view of elements of a work element, according to one embodiment. In this example, a tendon actuation tab 469 is present, similar to the distal end of the work element of FIG. 33A and similar to element 526 of FIG. 33B. The distal beak or beaks or scoopula or scoopulas are not visible in this illustration. In this illustration these structures are to the left, off the page, whereas the proximal end of the device (comprising the handle and other ancillary structures are to the right, off the page. In this embodiment, an inner tube and an outer tube are coupled to the work element. Elements of the inner tube comprise a tendon actuation tab 469, a tendon actuation tab welding point 589, a body portion 428, body portion welding points 588 and may also feature an extended flexible body portion 1b, which may be either contiguous with body portion 468, or separated as shown in the illustration. Element 1b features a flexible helical shaped portion 582, which may be coated according to one embodiment. An outer tube 2 may also feature a flexible element 585, a spot weld or glue hole 587 which may be matched to weld point 589 of an inner tube, and spot weld or glue holes 586 which may be matched to weld points 588 of an inner tube of a work element. An outer tube may also contain additional features for flexibility along its axial length or cuts such as 584 to enable vacuum or flush functions to be incorporated into a work elements overall function. An outer tube may also have an outer coating, according to one embodiment.

Figure 35:
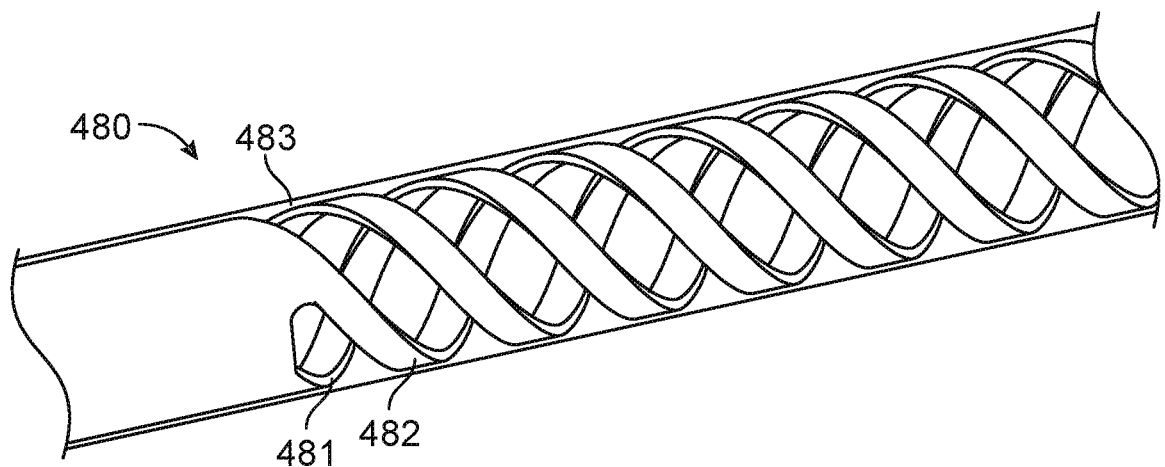
FIG. 35 shows a flexible, coated helical structure for a tube element of a work element, according to one embodiment.

FIG. 35 shows a configuration of a flexible body portion 480 of a work element tube, according to one embodiment. Flexible elements 481 and 482 may be disposed along its length and it may also be coated along part of all of its axial length, as indicated in this illustration.

Figure 36:
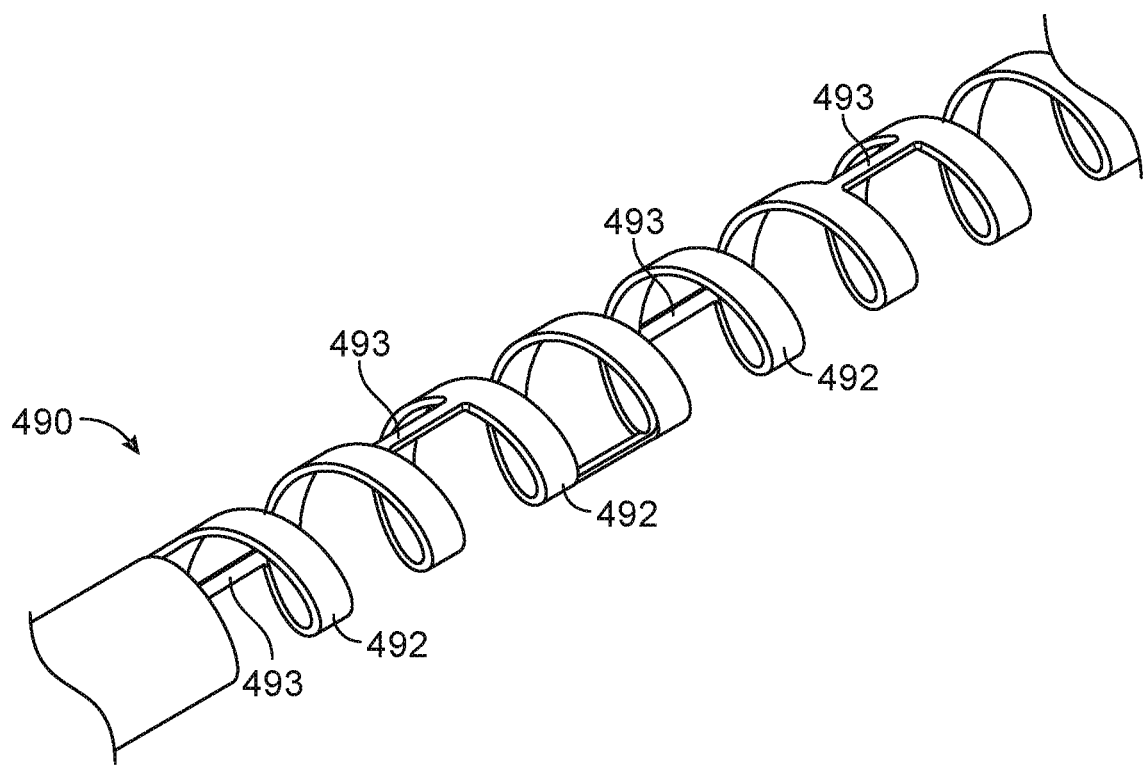
FIG. 36 shows a flexible, axially-constrained tube element of a work element, according to one embodiment.

FIG. 36 is one configuration of a flexible body portion 490 of a work element tube, according to one embodiment. Flexible elements 492 may have one or more linking structures 493 incorporated, and may be formed of a single laser cut hypo-tube, for example. There may be one or more such linking structures 493 for each turn of such a helix structure, which may also join multiple helices such as found in FIG. 35 above, in which case each link would alternately attach one helix to the other. Such linkages may serve to stiffen axial compression characteristics of a tube while still allowing lateral flexibility. Other helical structures to allow a similar latitude of functions may be readily envisioned, and are considered within the scope of this disclosure. A body portion 490 of a work element tube may also be coated or uncoated along part of all of its axial length, according to embodiments.

Figure 37A:
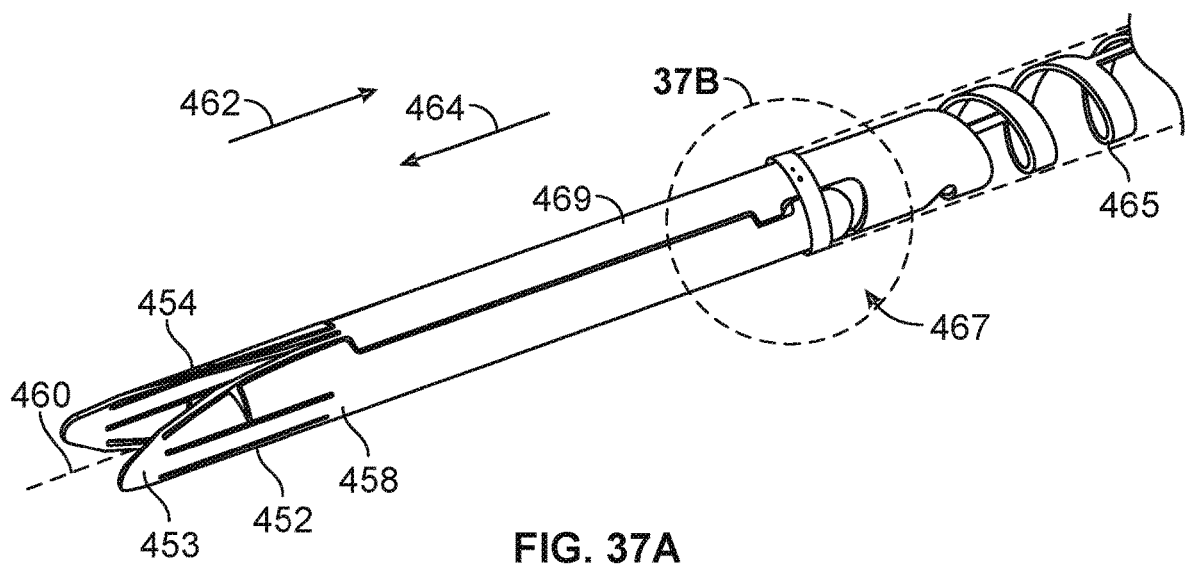
FIGS. 37A and 37B show details of a work element, according to one embodiment.
Figure 37B:
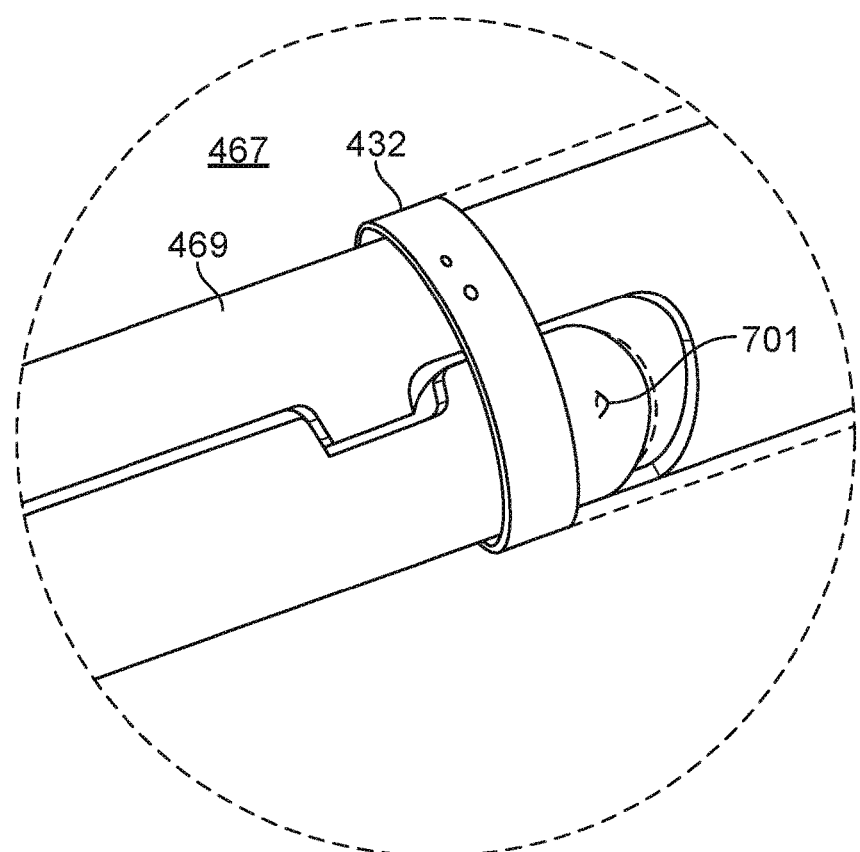

FIGS. 37A and 37B illustrate elements and features of a single tube work element, according to one embodiment. FIG. 37A shows a single tube with a distal work element as a monolithic structure and a proximal flexible extension 465 thereof. Reference numeral 460 illustrates a line of sight through the central lumen of the work element, which features one or more tip element(s) 453 (one of which may be fixed and non-articulable if two or more are present), living hinge(s) 452 formed by kerfs in the work element, tendon(s) 454, a tendon extension element 469 (as opposed to a tendon actuation tab discussed under other embodiments herein) and a body portion 458. Also illustrated is a collar 532, which may be a simple collar or an outer tube serving the same purpose, as suggested by the dashed lines extending proximally. The actions suggested by arrows 462 and 464 represent the action of the work element with differential axial forces acting on the tendon extension element 469 and body portion 458 of a work element, according to this embodiment. If, for example, element 469 is held in place while a distally-directed force 464 is applied to the body portion extension 458, the distal tips of the work element will tend to close and the reverse will be true if a proximally directed force 462 is applied to the work element.

FIG. 37B shows expanded details of portion 467 of FIG. 37A, wherein the collar 532 (or rigid or flexible outer tube, according to other embodiments) is fixed to the tendon extension element 469 by spot welding, for example. Note that in this embodiment, the body portion extension tab element 458 is unconstrained and is free to move axially in either direction within the limits of the aperture from which it is formed in the work element. In this embodiment, one or more dimples 701 may be welded onto the body portion extension tab, and extend under the collar or tube 532, thus pushing the tab slightly into the central lumen of the work element, and allowing it to be abutted by and acted upon by a tube, for instance, that may be placed into the central lumen to actuate the work element tips by pushing against the proximal edge of the body portion tab element 458 from within the work element.

Figure 38:
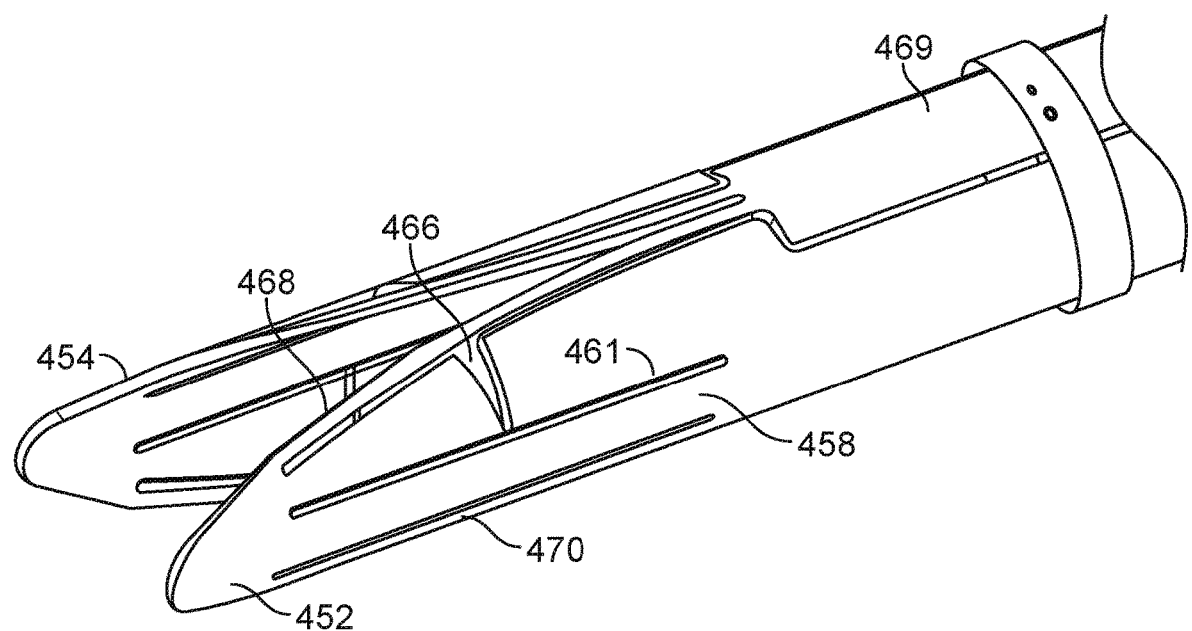
FIG. 38 shows details of a work element, according to one embodiment.

FIG. 38 shows a single tube work element as a monolithic structure, but differing from that of FIGS. 37A and 37B, according to one embodiment. In this figure, it should be noted that the tip 452 or tips 452/454 (as shown, but a single tip would function under the principles discussed herein, or an articulable tip acting against a fixed opposite tip would also be fully functioning, according to embodiments) are joined through tendon(s) 468/470 to a tendon actuation tab 469 (as opposed to a body portion actuation tab element 458 of FIG. 37B) and the tendon actuation tab 469 is attached to a collar 532. A force such as force 462 of FIG. 37A acting on the collar 532 would pull the tendon(s) 468/470 in a proximal direction, forcing the living hinge shown at 458 in this figure to flex and thus close the tip(s) against each other, or flex the single tip into the central lumen, or close one articulable tip against an opposite fixed tip, according to various embodiments. As shown, the forces acting against the tip or tips in this figure are similar to, but distinctly different from, in application, the embodiment of FIG. 37A. In this case, the tendons are pulled distally, pulling the tip(s) inward, whereas in FIG. 37A, the tendons are fixed and the body portion extension tab 458 is pushed distally to pull the tip(s) of that embodiment inward. While the net result is that the tip(s) close as a result of relative axial motion between portions of the single tube structures in each embodiment, the two configurations may be combined as discussed below to form a complex work element with a simple activation mechanism, according to a further embodiment.

FIGS. 37A and 37B illustrate elements and features of a single tube work element, according to one embodiment. FIG. 37A shows a single tube with a distal work element as a monolithic structure and a proximal flexible extension 465 thereof. Reference numeral 460 illustrates a line of sight through the central lumen of the work element, which features one or more tip element(s) 453 (one of which may be fixed and non-articulable if two or more are present), living hinge(s) 452 formed by kerfs in the work element, tendon(s) 454, a tendon extension element 469 (as opposed to a tendon actuation tab discussed under other embodiments herein) and a body portion 458. Also illustrated is a collar 532, which may be a simple collar or an outer tube serving the same purpose, as suggested by the dashed lines extending proximally. The actions suggested by arrows 462 and 464 represent the action of the work element with differential axial forces acting on the tendon extension element 469 and body portion 458 of a work element, according to this embodiment. If, for example, element 469 is held in place while a distally-directed force 464 is applied to the body portion extension 458, the distal tips of the work element will tend to close and the reverse will be true if a proximally directed force 462 is applied to the work element.

FIG. 37B shows expanded details of portion 467 of FIG. 37A, in which the collar 532 (or rigid or flexible outer tube, according to other embodiments) is fixed to the tendon extension element 469 by spot welding, for example. Note that in this embodiment, the body portion extension tab element 458 is unconstrained and is free to move axially in either direction within the limits of the aperture from which it is formed in the work element. In this embodiment, one or more dimples 701 may be welded onto the body portion extension tab, and extend under the collar or tube 532, thus pushing the tab slightly into the central lumen of the work element, and allowing the tab to be abutted by and acted upon by a tube, for instance, that may be placed into the central lumen to actuate the work element tips by pushing against the proximal edge of the body portion tab element 458 from within the work element.

FIG. 38 shows a single tube work element as a monolithic structure, but differing from that of FIGS. 37A and 37B, according to one embodiment. In this figure, it should be noted that the tip 452 or tips 452/454 (as shown, but a single tip would function under the principles discussed herein, or an articulable tip acting against a fixed opposite tip would also be fully functioning, according to embodiments) are joined through tendon(s) 468/470 to a tendon actuation tab 469 (as opposed to a body portion actuation tab element 458 of FIG. 37B) and the tendon actuation tab 469 is attached to a collar 532. IN operation, a force such as force 462 of FIG. 37A acting on the collar 532 would pull the tendon(s) 468/470 in a proximal direction, forcing the living hinge shown at 458 in this figure to flex and thus close the tip(s) against each other, or flex the single tip into the central lumen, or close one articulable tip against an opposite fixed tip, according to various embodiments. In this case, the tendons are pulled distally, pulling the tip(s) inward, whereas in FIG. 37A, the tendons are fixed and the body portion extension tab 458 is pushed distally to pull the tip(s) of that embodiment inward. While the net result is that the tip(s) close as a result of relative axial motion between portions of the single tube structures in each embodiment, the configuration of FIG. 38 and that of FIG. 37A may be combined as discussed below to form a complex work element with a simple activation mechanism, according to a further embodiment.

From the discussions of FIGS. 37A, 37B and 38 above, it may be envisioned that two single tube work elements may be combined to form a complex work element comprising an inner and outer work element, each of single tube configuration that may be independently and differentially extended and/or rotated with reference to each other, according to one embodiment of device 10. Such a device may comprise an outer tube with an independent work element, comprising for example, a single articulable scoopula as its distal tip, and an inner work element, comprising a single scoopula or beak, depending on embodiments. In such a complex work element where two independent work elements are combined, the device of FIG. 37A may serve as the outermost tube work element, and the device of FIG. 38 (having, for example, a single beak element) may serve as the inner tube work element, according to one embodiment. If the outer diameter of the collar 532 of FIG. 38 matches the inner diameter of the central lumen of a device of FIG. 37A, then that collar 532 may act on the body portion extension 458 of FIG. 37A, as it is shown extending partially into the central lumen of a device of FIG. 37A in FIG. 37B, because of the dimples 701 forcing the collar 532 slightly inward. Since a proximally-directed force on collar 532 of the device of FIG. 38 tends to pull on the tendon actuation tab 469 and force its tip(s) inward, and a distally-directed force pushing on the proximal tip of the body portion extension tab 458 (the tip of that tab itself extending into its tube's central lumen slightly), a distally-directed force acting on the inner work element of FIG. 38 would tend to close the tip(s) of the work element of FIG. 38 as well as the tip(s) of the outer work element of FIG. 37A. In this manner, a complex work element may be constructed in which differential rotation of the inner and outer work elements may be independent, but in which simultaneous closing of the tips of both inner and outer work elements may be effected through an axial motion of the tube of the inner work element.

In further embodiments, a single scoopula of an outer device of FIG. 37A, combined with an inner device of FIG. 38, may allow for the inner beak, in the example cited, to nest into the outer already flexed scoopula, which may be advantageous if the outer scoopula work element is used as a downstream barrier while the inner beak work element acts to remove or dislodge material upstream from that point and from, for example, the lumen of an artery. Such an embodiment may also be advantageous, as will be illustrated later, to grasp both edges of an arterial obstruction simultaneously while still allowing one or both work elements to rotate independently of the other. According to one embodiment, a third independent work element, which may comprise a coring excisional device, may also be introduced down the central lumen of the complex work element discussed in this paragraph. In such a method, the complex work element, with its independent work elements, could serve as a complete shield and isolate an inner work area between the two work elements, while a third coring or excisional work element is introduced to selectively retrieve material in the central lumen of such an artificially-created work area, thus protecting sensitive subjacent arterial wall structures from the actions of the excisional work element. Any debris dislodged by the coring or excisional process of the excisional device may then be contained within the work area defined by the complex work element described above, according to embodiments.

Other embodiments of a device 10, comprising complex work elements each of which may be single or double tube work elements, with single or multiple beaks, scoopulas, combinations of the two, and including exchangeable independent work elements or separate devices, introduced into the central lumen of such a device with complex work elements, may be envisioned by one skilled in the art and are thus considered within the scope of this disclosure.

Figure 39A:
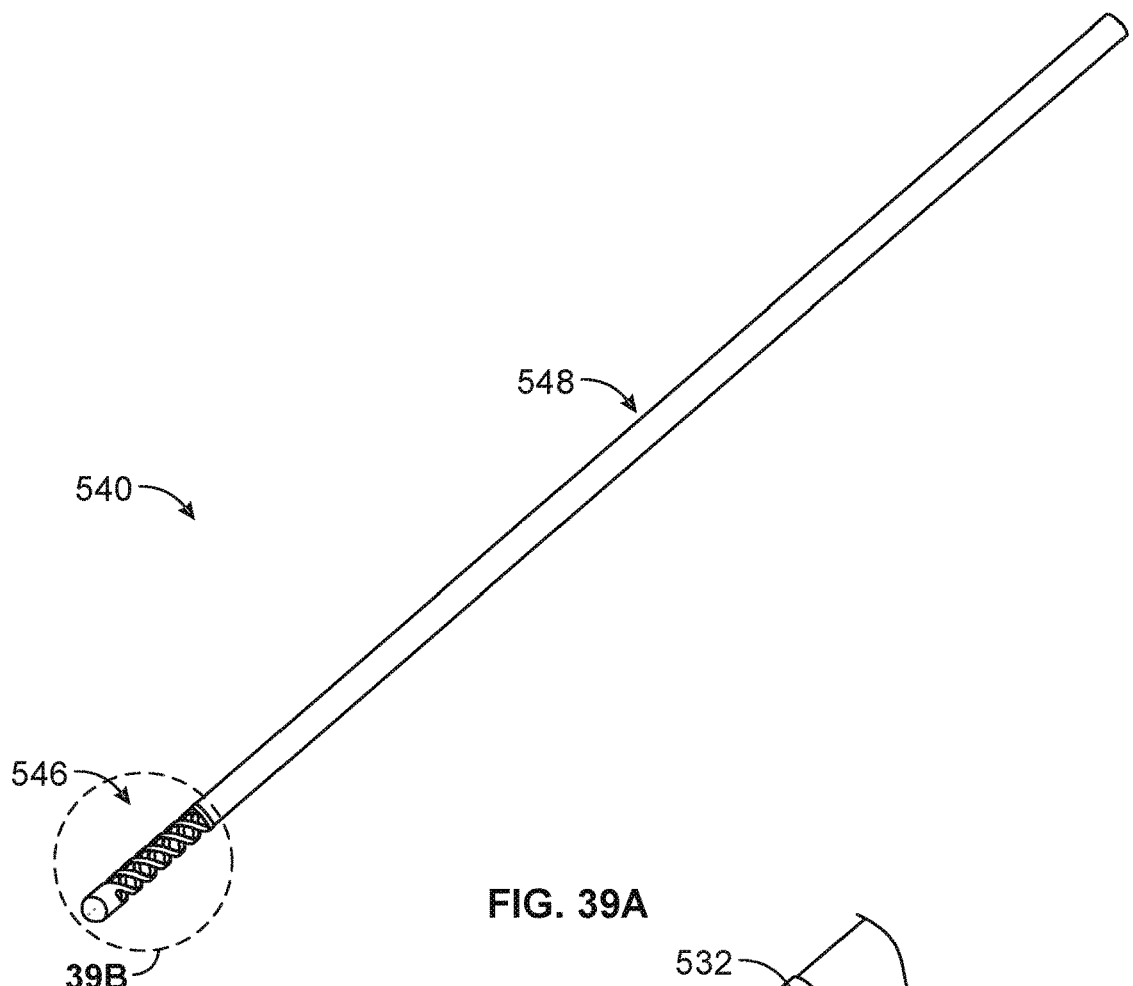
Figure 39B:
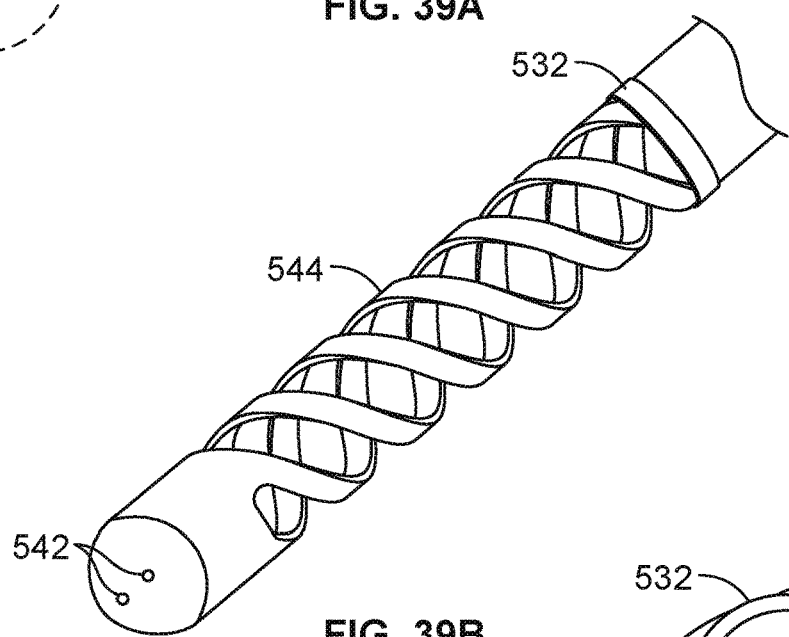

FIGS. 39A and 39B show a monolithic expander element 540, comprising a distal portion 546, a body portion 548 and a collar 532, according to one embodiment. This expander element 540 may have a flexible structure 544 and spot weld holes 542 in its angle cut tip, as shown in FIG. 39B. Such an expander element 540 may, for example, be monolithic and laser cut from a single hypo tube, which may be of any gauge size. For instance, the expander element 540 may be sized in a range of approximately 21 gauge to 12 gauge, for example, and its central lumen may be capable of accommodating a guide wire, imaging modality such as fiber optic cameras or OCT scanners to follow within its axial length and emerge from its unobstructed tip. Collar 532 may be fixed to the body portion 548 by any of a number of methods, including laser spot welding or via an adhesive. The flexible expansion portion 544 may be of a variety of configurations, such as, for example, those illustrated if FIGS. 35 and 36. According to other embodiments, the proximal portion of the expander element 540 may be formed of a tube with a shoulder and second larger diameter, the shoulder being located approximately where the collar 532 is located and functioning in place of a collar element. According to other embodiments either a collar or shoulder element may be located at any point along the proximal body portion of the expander element 540, including at the proximal terminus of the element 540, since a torsional force applied to any point proximal to the flexible structure 544 will result in either an expansion of that flexible structure 544 or in its contraction, depending on the direction of rotation of the torsional force applied to this expander element 540. Indeed, a contraction of the flexible structure 544 may be useful in gripping, for example, a guide wire element introduced through its central lumen.

Figure 39C:
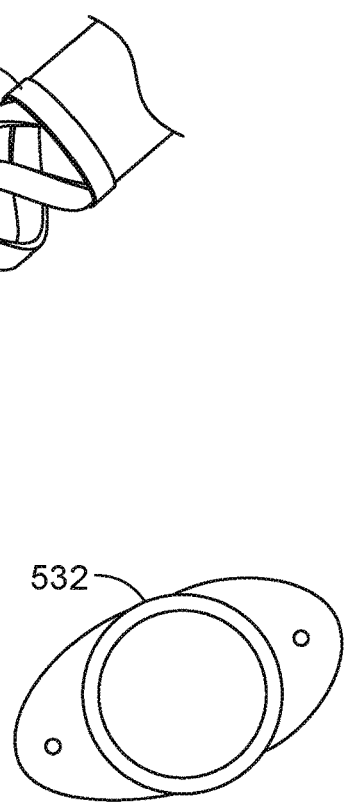

FIG. 39C illustrates a separate ring collar with a flattened plate base 532 and spot weld holes, according to one embodiment. The inner diameter of the ring collar 532 may be of sufficient diameter to pass over the outside diameter of a corresponding gauge size of an expander element 540 of FIG. 39A, and may be spot welded through its spot weld holes to, for example, the outside of an outer tube work element such as in FIG. 37A, such that its proximal face of the collar 532 abuts the distal face of the collar 532 of the expander element 540 of FIG. 39A, according to one embodiment. If an expander element is slid from the proximal side of this fixed collar so that its own collar abuts the proximal face of the fixed collar, and then the expander element's distal tip is also spot welded, for example, near the distal tip of the outer tube of a work element such as that of FIG. 37A, the helical portion 544 of the expander element will be constrained in axial dimension by its own welded tip and the welded collar of FIG. 39C. This configuration still allows rotation of the body portion 548, but not the tip portion at 542 of the expander element. In the configuration shown in FIG. 39A, if a clockwise rotational force, looking from the proximal end of the expander element, is applied to the body portion 548 of the expander element, that the helical coils 544 of the expander element will expand outward as the coils try to unwind from their normal tightly coiled position at rest while the length of the helical section remains unaltered. Conversely, any counter-clockwise rotational force will allow the helical coils 544 to relax or contract back to their original diameter or less, if desired. The outside diameter of the helical coil portion 544 may be established, maintained or changed at any time by the use of differential rotation of the expander element 540 and any external structure to which it is attached.

Such an expander element expands its helical coil 544 structure as a result of rotational force applied while axial movement is constrained, or where rotational force is constrained and axial force is applied, or in any range of degrees of combination of the two forces, which may allow extremely fine tuning of the resultant diameter of the helical coil 544 structure of an expandable element 540 at any point of a procedure, according to embodiments. Any axial forces imposed by torsional force on the body portion 548 of the expander element 540 may, for instance, be constrained by a second collar 532 welded to the outside of an outer work element. Such expansion/contraction actions of an expander element 540 may serve to, for example, allow or re-establish blood flow around an arterial obstruction, for instance over the dorsal portion and outside of an attached work element, while such an attached work element itself may be applied to isolating or removing the obstruction itself, according to methods herein. According to one embodiment, the expander element may be placed or arranged on the exterior of an outer tube work element. It should be noted again that the central lumen of the expander element, thus fixed to another outer tube work element, may allow the outer tube work element to be extended inside a vascular structure along a pre-placed guide wire or imaging modality that may be previously placed into the central lumen of the expander element 540. A guide wire or other imaging modality may also be placed beyond an arterial obstruction by being introduced through the central lumen of a pre-placed work element with attached expander element. The presence of, for example, a guide wire would not obstruct existing or re-established blood flow if the expander element is suitably gauged or expanded during a procedure.

According to another embodiment, as shown in FIG. 39D, in more detail in FIG. 39E, and in an end on view in FIG. 39F, an expander element 540 may be fixed at its distal end to any point along the inside radius of a scoopula portion of a work element, for example, and a proximal tubular portion, which may also be flexible, of expander element 540 may be placed co-axially within the central lumen of such a work element as shown at flexible element 528 and proximal end 530 of such a work element, which may end in a scoopula or scoopulas, or in beaks or any combination thereof. Also shown in FIG. 39D is a centrally placed guide wire which may have imaging capability to serve as a forward looking guide for a procedure. Such a device may take advantage of an elongated open portion of a scoopula, as shown as element 550 in FIG. 39E, which may itself be flexible, as a stable platform from which to expand the expandable element 540 within the open portion of the scoopula. Such a combined work element may be useful, for example, in the case in which the tip of such a scoopula/expander element work element is initially placed at the junction of an obstruction and the inner wall of a vascular structure. Expansion of the expansion element 540 lying in and fixed to the scoopula 550 may be used to gently pry the obstruction from the vascular intima layer in successive stages as the scoopula is gradually advanced between the vascular wall and the obstruction, according to one embodiment. Such a procedure may result in establishment or re-establishment of blood flow along one edge of an obstruction by creation of a temporary artificial alternate flow structure, thus allowing for another separate work element, which may be primarily functionally oriented towards isolating/coring/capturing of obstructive material as described elsewhere herein, to attack the obstruction laterally alongside the scoopula/expander element work element, according to methods.

Another embodiment, as shown in FIG. 39E, may comprise a complex work element comprising an outer tube terminating in a fixed scoopula work element 551, an inner tubular structure, also terminating in a fixed scoopula work element 550, and which is free to rotate independently of the outer work element, and further to which may be fixed a third inner tubular structure, comprising an expander element 540. Such a complex work element may thus use its independently rotatable scoopulas, in for example an oscillating (in relation to one another) forward cutting scissors or shearing action, to separate an obstruction such as a CTO from a vascular wall, and advance along that obstruction/vascular wall junction, successively expanding the thus separated area with the inner expansion element, according to one embodiment. In this manner, the obstruction immediately distal to the two scoopulas may be slightly expanded. This embodiment allows for precise forward cutting action of the two scoopulas biased towards the edge of the obstruction, and thus protects the sensitive vascular wall structure. Successive stages of such a procedure enables the present device to very gently advance distally to establish a temporary blood flow path adjacent to the obstruction. The obstruction may then be attacked and removed by other work elements working laterally alongside and independently of the complex work element described in this paragraph, according to further embodiments. As shown in FIG. 39F, the concentrically-placed outer work element 551 may have the tip and edges of its scoopula distal extension bevel sharpened with an outside bevel, and an inner work element 550 may have its scoopula distal extension tip and edges sharpened with an inside bevel so that the two bevels nest into each other and therefore do not present a very sharp tip to the tissue or obstruction that the combined and aligned tip may encounter. If the two tips of the two scoopulas are separated by a slight repeated back and forth rotation, the cutting action will be largely concentrated at the two tips in a forward-cutting shearing scissors action, which may be a very gentle way to urge the complex work element forward distally between a vascular wall and obstruction, for example. As the two tips oscillate (slightly rotate and return to original position) relative to one another and cut forward, the expander element 540 may be expanded periodically or as desired to anchor the work element at its distal most progress point, according to one embodiment. Further, according to another embodiment, if the outer work element 551 comprises a distal terminus with an articulable scoopula, the articulation of such scoopula may allow the entire complex work element to be slightly angled to fine-tune the penetration path between the vascular wall and obstruction.

According to one embodiment, such a complex work element (a fixed or articulable outer scoopula/fixed inner scoopula with attached inner expander element) may be of very small diameter in relation to an obstruction or inner lumen of a vascular structure or other work elements. The temporary blood flow channel that may be created by this complex work element may thus be outside of the obstruction itself, allowing such an obstruction to be subsequently attacked and removed by other work elements or devices without interfering with their action, according to embodiments. It should be noted that when a temporary blood flow channel is thus established, the expander element 540 helical structure may also serve as a large particle screen to exclude from the blood flow and downstream any debris that may have been dislodged as a result of an adjacent procedure with another work element to core and remove an obstruction. Once a temporary blood flow channel has been established through a procedure using the device of FIG. 39E, any adjacent work element used to core or otherwise remove an obstruction such as a CTO is able to take full advantage of aspiration internal to that adjacent work element or device, since blood flow was established around the obstruction by a temporary blood flow channel, thus increasing the safety of an operation where it may not be desired to lose even very tiny particles dislodged from removal procedures of an obstruction. The embodiment of a tube within a tube within a tube need not be bulky, as the central lumen of such a work element may be extremely small—for instance only large enough to pass a very small gauge guide wire inside, according to embodiments. Such a very small diameter complex work element, however, may be advantageously used to create a temporary blood flow path between an obstruction and vascular wall that may be many times larger in diameter than the outside diameter of the outermost tube of the work element, as a result of the expansion capabilities of the expander element 540 fixed thereto. Once an interventional procedure has been finished, the complex work element described herein may simply be contracted as a result of the expander element 540 returning to its original conformation, and at which point this work element may be withdrawn from the site and removed from the body, according to embodiments.

According to embodiments, a constraining sub-element, such as collar 532 or shoulder area of an expansion element 540, may be located at any point along the proximal portion of such a combined work element/expander element, including at its proximal terminus (i.e., in a handle portion of a device, or otherwise outside the body) and may be controlled by a mechanism that allows for a rotational force to be applied to the inner expander element 540 while the external work element is held stationary, or where there is a differential in rotational speed between the co-axially located inner expander element 540 and outer work element of varying configurations, according to embodiments. Indeed, an expander element 540 fixed to the inner diameter of an open scoopula, according to embodiments, would be limited in the axial or lengthwise extent of its lateral expansion by its fixed distal point or points 542 and the proximal opening of the scoopula to which it may be attached.

Figure 40:
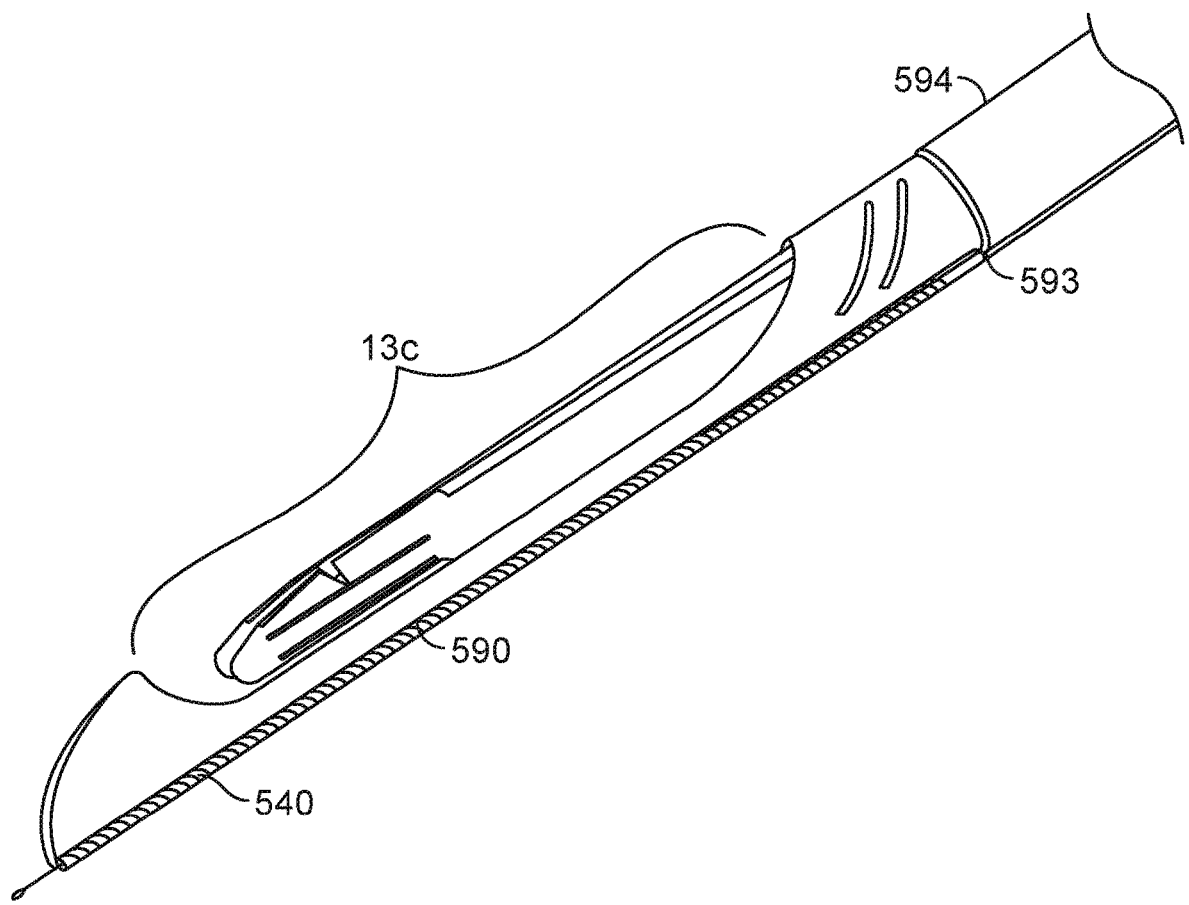
FIG. 40 shows details of an excisional device, according to one embodiment.

FIG. 40 illustrates a device 10 comprising an attached expander element 540 and an independent excisional device in its central lumen, according to one embodiment and method. As shown, the work element of the device comprises a fixed scoopula tip. However, an articulable scoopula tip may be used with for example, a distally extended flat portion, as a portion of a rigid or flexible outer tube 594 with first and second external and internal diameter portions, differentiated by shoulder 593. In this view, an imaging modality such as an OCT scanner on the end of a guide wire has been placed in the central lumen of the expander element 540 fixed to the dorsal portion of the fixed scoopula. The work element may have additional fenestrations along its axial length as suggested in this figure which, in concert with an expanded helix section of an expander element 540, allows blood flow around the work area defined by the open cut out section of work element 594 proximal to the scoopula tip. In this figure, a separate coring or excisional device with its own work element may be introduced down the central lumen of the work element 594 to excise obstructive material from within, for example, the lumen of an artery. The work area thus defined may serve to protect subjacent sensitive wall structures of an artery while the smaller diameter excisional device selectively removes material blocking the artery, as further detailed below. According to one embodiment, the complex work element of FIG. 38 may be placed into this outer tube with fixed scoopula, and may include, in its inner lumen, access for any one of a number of excisional devices. The outer tube and fixed scoopula embodiment shown in FIG. 40 may be first introduced into an arterial structure, and a separate and independent work element, as shown in FIG. 38, may be introduced in its central lumen as a second phase of a method or procedure. In such an implementation, the tip or tips of the second work element of FIG. 38 may be actuated against the shoulder 593 of work element 594. Additionally, according to other embodiments, device of FIG. 40 may itself be the complex work element described relative to FIG. 38, as a second scoopula-equipped work element may be placed in conjunction with work element 594 of FIG. 40, according to one embodiment.

In FIG. 40, work area 13c represents an opening bounded by the tip and that portion of the work element that resumes the generally tubular shape. According to one embodiment, within such a work area 13c, work may be accomplished inside a vascular channel by any one of a number of additional work elements advanced through the central lumen of a first placed work element (in this case a fixed scoopula shaped extremity). For example, a fixed shaped scoopula work element may be first advanced to anchor to an anomaly within a vascular structure, and then a twin beak work element may attack the anomaly using its designed functionalities, according to one embodiment. Other embodiments may utilize advancement of one or more different work elements associated with devices 10 through the central lumen of a first placed work element to accomplish selected different intra-operative procedures in sequence, according to other embodiments.

Figure 41:
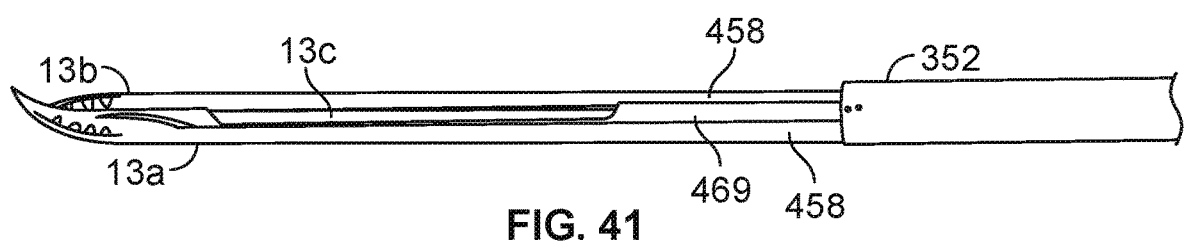
FIG. 41 illustrates a complex device, comprising two independent work elements, according to one embodiment.

FIG. 41 is an illustration of a complex work element according to one embodiment, as discussed relative to FIG. 38. As shown, the two work elements are articulable scoopula-based work elements, which may be rotated independently of one another. Work element 13a is placed first, followed by a subsequently advanced and placed work element 13b. As shown, and as described above in FIG. 38, if work element 13b is advanced to its end point, the action of its collar 532 (not visible in this view) will act on the tube 532 shoulder of work element 13a, resulting in both scoopulas being closed, with work element 13b nested into work element 13a. Body portions 458 of each work element are visible in this figure, as is the tendon extension element 469 of work element 13a, for consistency of understanding. In this illustration, the work area 13c is nearly closed, and may be completely closed by overlap of the inner and outer work elements in order to protect subjacent arterial wall structures. Even though the overlap of the inner and outer work elements may effectively close their respective work area windows, continuing to press one beak element of one work element against the other, i.e., if one or both beaks have a force pressing them together beyond merely allowing them to close against each other, then the work area windows incorporated along their axial lengths will open as a result of the expansion force thus created at the distal end of the complex work element. Such action may be of use to an operator who may desire to locally expand the internal lumen of a vascular structure while also maintaining free flow through and distal to a complex device.

Figure 42:
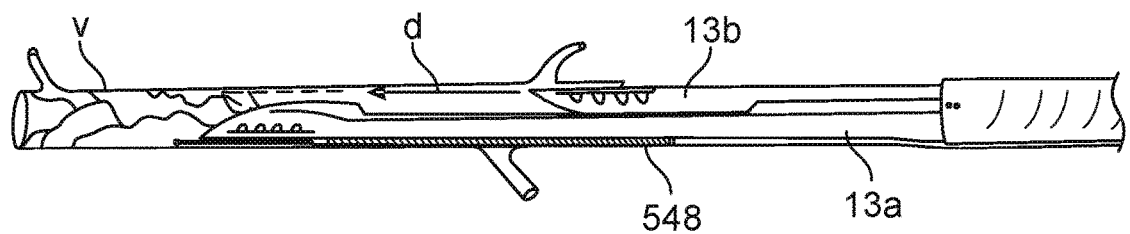
FIG. 42 shows a complex device, comprising two independent work elements in a vascular structure, according to one embodiment.

FIG. 42 shows the complex work element of FIG. 41 advanced into a vascular structure v, in a configuration in which work element 13a has been advanced to the edge of a chronic total occlusion that is to be removed from the vascular structure v. In this view, the work element 13a comprises an expander element 548 coupled to its dorsal structure through which a first placed guide wire with an imaging modality has been placed in proximity to the point where the vascular anomaly touches the vascular intima. Also shown in this figure is the second work element 13b as it advances in the central lumen of 13a to take a place opposite 13a and thus anchor the anomaly in place, according to one embodiment. Once anchored in place, other smaller diameter work elements may be advanced through the central lumen of work element 13b for sequential procedures, as desired by an operator. As previously noted, the complex work element shown in this figure represents only two thin wall tubes concentrically placed relative to one another. With such a device, the handle 12 may be provided with a Vernier scale screw mechanism to precisely establish and determine the degree of closure of the two work elements relative to each other by advancing 13b relative to 13a, while allowing 13b to rotate manually in relation to 13a. Such a handle mechanism allows access to the central lumen of both work elements, for introduction of additional work elements or excisional devices, according to embodiments.

Figure 43A:
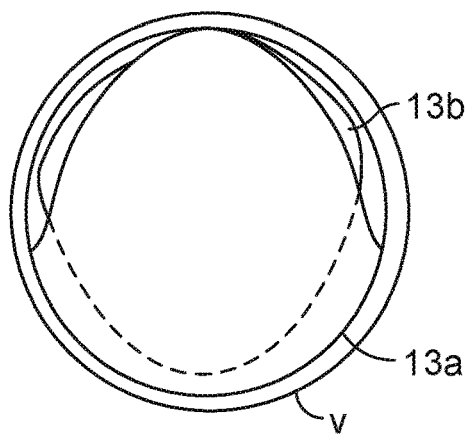
FIGS. 43A, 43B and 43C show end on perspective views of the distal end of a complex device, comprising two independent work elements, according to one embodiment.
Figure 43B:
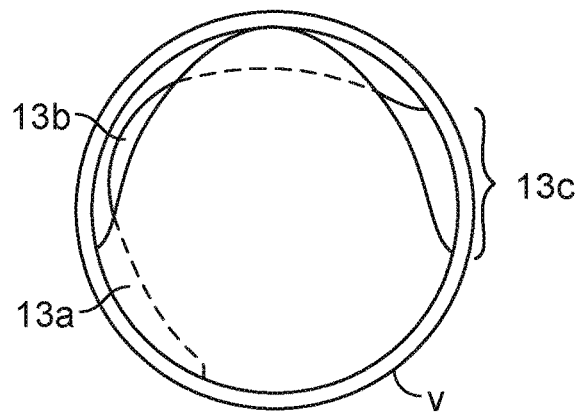
Figure 43C:
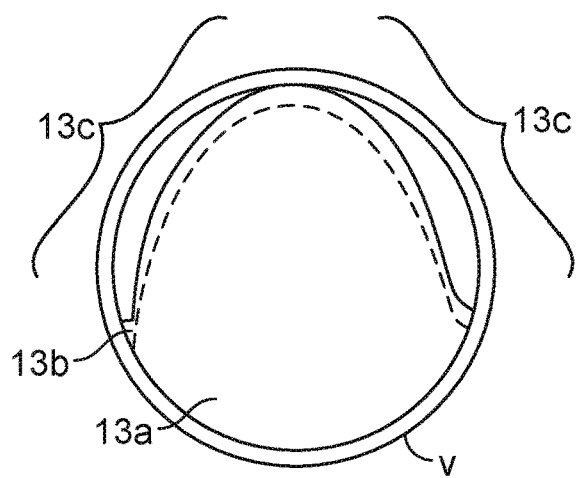

FIGS. 43A, 43B and 43C show end on perspective views of a complex two work element comprising first and second work elements 13a and 13b, working in concert with both scoopulas in closed and nested position, according to one embodiment. In FIG. 43A, the two scoopulas have been placed opposite to each other, effectively closing their respective work areas 13b. In FIG. 43B, the work element 13b has been rotated, opening a joint work area 13c on the right side from this perspective. In FIG. 43C, both work elements 13a and 13b have been aligned by further rotation of work element 13b independently of work element 13a, and thus the combined work areas 13c may be expanded or contracted as desired by an operator. Such rotation may be accomplished independently of the degree of closure of both scoopulas, according to an embodiment.

Figure 44:
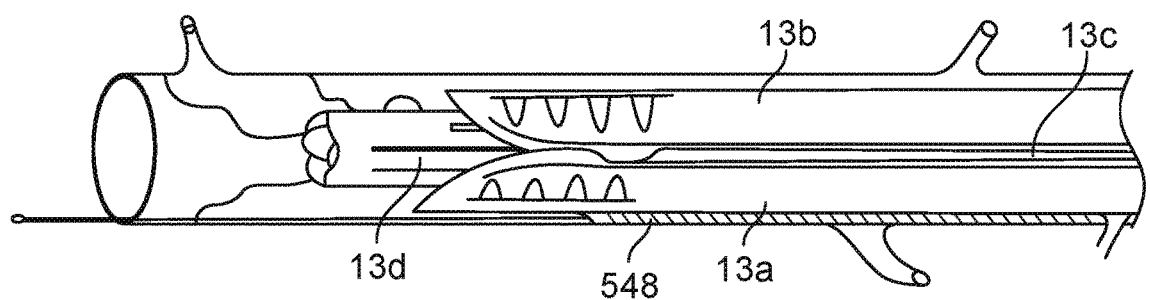
FIG. 44 is a side perspective view of a complex work element assembly of a device in the lumen of a vascular structure, according to one embodiment.

FIG. 44 is a side perspective view of two work elements working in concert, inside a vascular structure, according to one embodiment. It is common to find that the occluding material includes a soft thrombotic cap on the surface of a hard, aged, calcific, mature, underlying plaque. In this view, the two scoopulas are in an open configuration and are grasping the near end of the hard cap structure of a chronic total occlusion. In this view, according to one method, a third element representing the distal end of an excisional device may be seen already having penetrated through the hard cap of the occlusion. This third excisional device may then be withdrawn, according to one embodiment, and the complex work element comprising the two work elements 13a and 13b may be advanced further into the softer occlusion material. Also shown in this figure is the expansion element 548 in its still un-deployed configuration and with a guide wire extending from its central lumen past the occlusion.

Figure 45:
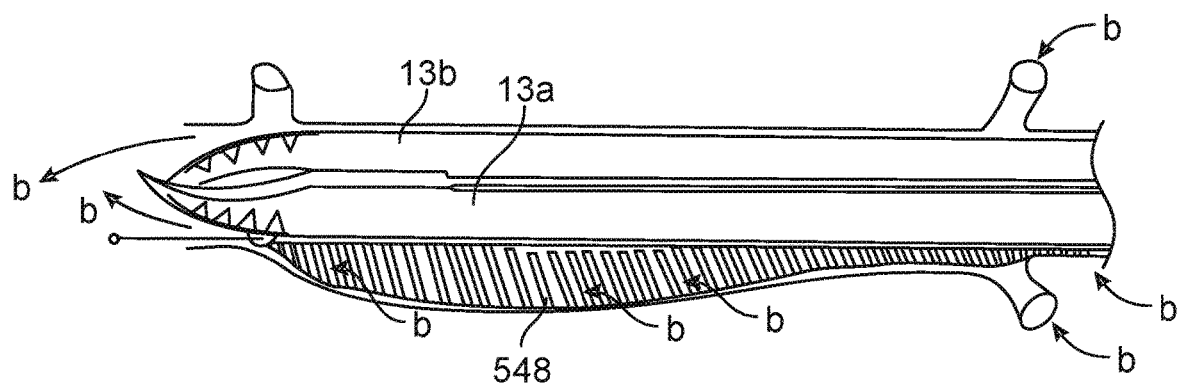
FIG. 45 is a side perspective view of a complex work element assembly and expander element of a device in the lumen of a vascular structure, according to one embodiment.

FIG. 45 is a side perspective view of further aspects of the procedure started in FIG. 44, according to one embodiment. As shown the complex work element comprising work elements 13a and 13b has been advanced to the end of the CTO, and have captured the occlusion in their central lumens, blocking loss of fragmented material downstream. Vacuum may be provided to the central lumen of the complex work element. Alternatively, another excisional device, optionally operating at a comparatively lower speed, may be introduced axially to selectively and securely remove material from the central lumen work area of the complex work assembly 13a/13b. Also shown in this figure, not to scale but deliberately exaggerated, is expansion element 548 having been deployed to allow blood flow, represented by arrows b, to be re-established around the site of the CTO in the vascular structure. This is shown as though it is an ending stage, although it should be noted that deployment/un-deployment of an expansion element 548 may occur at any stage of a procedure, including, if desired, to gently force the vascular wall away from the occlusion in several steps, allowing gentle further advancement of work element 13a along the occlusion. In this figure, the guide wire initially placed is still extended through the central lumen of the expansion element 548.

According to embodiments, one method of clearing a total chronic occlusion may include advancing a guide wire to one edge of such an occlusion, the guide wire being furnished with a guidance modality such as OCT, fiber optic camera element or ultra-sound transponder, for example. Once the guide wire is in place, work element 13a may be advanced by itself over the guide wire or over the guide wire through the central lumen of an attached expansion element 548, if used, to place its scoopula tip on the same edge of the occlusion. Subsequently, an excisional work element of a separate excisional device, such as shown previously in FIG. 40, may be used to attack the hard cap of the occlusion with high speed cutting and coring rotation. Alternatively, work element 13b may be advanced to grip and anchor the opposite side of the occlusion's typically hard cap, followed by a range of optional procedures. All such procedures are now available due to the establishment of access to the occlusion while protecting the subjacent arterial wall structure. Once the hard occlusion cap has been penetrated and removed, the complex work element assembly comprising work elements 13a and 13b may be incrementally advanced, with or without incremental scoopula closures in varying degrees at various steps, which may be useful in incrementally isolating portions of the occlusion to be removed and thus preventing debris from flushing downstream and avoiding complications due to embolic results caused by loose debris.

At any point in a procedure, the expansion element 548 may be deployed to loosen the occlusion from an arterial wall in a gentle manner, and work element 13a may also be rotated to accomplish such action around the 360 degrees of the inner arterial structure. The expansion element 548 may also be used at any time to re-establish blood flow around the occlusion, thus also serving to provide an alternate downstream blood flow away from the isolated work area inside the central lumen of the nest work elements 13a, 13b of the complex work element, according to embodiments. Once the bulk of the occlusion has been removed, work element 13b may be removed and the work area of work element 13a may provide access to and additional shaving or removal of material from the arterial wall. Work element 13a may span the entire inner diameter of the vascular structure v, and thus serve as a dam to prevent debris from such operations from being carried downstream, according to one embodiment.

Figure 46A:
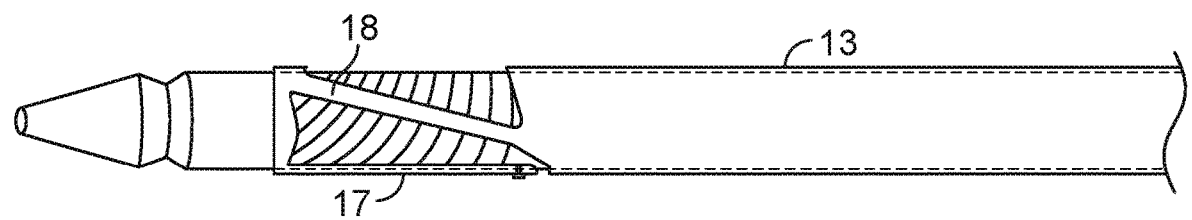
FIGS. 46A and 46B show perspective views of a steerable guide wire or guiding catheter, according to embodiments.
Figure 46B:
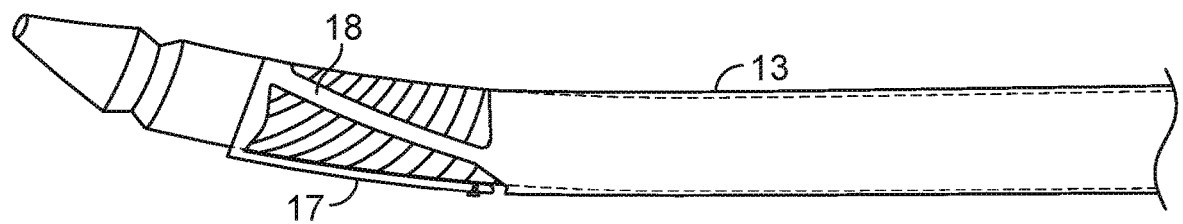

FIGS. 46A and 46B illustrate perspective views of a steerable guide wire or guiding catheter, according to embodiments. FIG. 46A shows a work element 13 comprising a guide wire (or catheter), similar to those shown in FIGS. 13 and 14 whose outer flexible tube or coat includes a living hinge incorporated into it and fused, at the proximal end of the living hinge, to the guide wire inner tube, which may itself comprise any of a number of embodiments such as an OCT scanning terminus, for example. As shown in FIG. 46B, a pair of V-shaped (one is visible in these side views) tendons 18 work opposite the living hinge 17 to bend the guide wire terminus in a desired degree of deflection when a distally-directed axial force is imposed on the inner tube of the guide wire. In use, rotation of the guide wire coupled with this living hinge/tendon combination allows directionality, i.e., for the tip of the guide wire or guiding catheter to be steered around bends as forward (distal) penetration of, for example, an artery is pursued, according to embodiments. This embodiment may be contrasted to that of FIGS. 14A through 14D, where a separate work element is introduced over a guide wire and that work element's living hinge, tendons and beak or scoopula influence the degree of bend in the guide wire. According to other embodiments of work elements, multiple living hinge/tendon sets allow for additional steering axes. According to one embodiment, an outer tube integrated collar may be provided in place of the living hinge(s) 17. Indeed, the device may comprise an outer tube integrated collar such as shown at the distal end of the outer tube of this steerable guide wire illustration of FIG. 46B, with tendons 18 connected acting on one edge of such collar, securely attached (glued, for instance) to the guide wire tube. Such a configuration allows an easy modification (addition of a flexible outer tube with integrated distal collar and tendons attached to one edge of the collar) to any existing guide wire or guiding catheter, transforming it into a steerable work element. In such a case, the flexible guide wire, acting as an inner tube, becomes the living hinge acted upon by an encircling and fused collar, as a result of the tendons action with relative distal force applied to the guide wire while the outer tube is held stationary. Additionally, a membranous element or elements or a meshwork may encircle or partially, selectively cover all or portions of the device according to embodiments, contributing a living hinge element or elements that may enable directional bias as well as adding structural integrity as may be desired.

According to another embodiment, a monolithic outer tube, comprising a series of collars spaced apart from each other, each with a single tendon connecting them in a linear configuration and configured so that only the most distal collar is fixed to the internal tube of a flexible guide wire as described above, would function as a steerable work element. In such a steerable work element, a relative distal force, acting on the inner guide wire while the outer tube is held stationary, may be operative force the distal tip of the combined work element to flex in a controlled manner, allowing for the tip to curve back on itself in a U configuration or even to scribe a circle. In this embodiment again, the guide wire acts as a living hinge, and the tendons between collars work together to enable this movement.

The described embodiments may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a work element 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material delivery or removal device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method, comprising:
   introducing a first work element into a vascular structure, the first work element comprising a lumen, a distal portion defining at least one articulated scoop-like structure;
   isolating a work area within the vascular structure from areas in the vascular structure that are proximal and distal to the at least one articulated scoop-like structure by flexing the at least one articulated scoop-like structure toward and against a wall of the vascular structure;
   introducing a second work element within the lumen in the first work element and into the isolated work area, the second work element comprising a tube of material from which material is removed to form at least one articulable beak, and
   flexing the at least one articulated beak independently of the articulated scoop-like structure and causing the second work element to cut tissue within the isolated work area.

2. The method of claim 1, further comprising moving the first work element within the vascular structure, isolating another work area, and causing the second work element to cut tissue within the isolated another work area.

3. The method of claim 1, wherein isolating comprises inserting the at least one scoop-like structure between an occlusion within the isolated work area and the wall of the vascular structure.

4. The method of claim 1, further comprising enabling blood flow across the isolated work area.

5. The method of claim 1, wherein introducing the first work element is carried out with the first work element being formed of a single tube of material from which material is removed to form the at least one scoop-like structure.

6. The method of claim 1, wherein the second work element comprises at least one tendon and a living hinge coupled between the at least one articulable beak and the least one tendon and wherein the method further comprises applying a distally-directed or a proximally-directed force on the at least one tendon to cause the at least one articulable beak to flex via the at least one living hinge.

7. The method of claim 1, wherein the first work element comprises at least one tendon and a living hinge coupled between the at least one scoop-like structure and the least one tendon and wherein the method further comprises applying a distally-directed or a proximally-directed force on the at least one tendon to cause the at least one scoop-like structure to flex via the at least one living hinge.

8. The method of claim 1, further comprising stabilizing the first work element within the vascular structure, thereby stabilizing the isolated work area.

9. The method of claim 8, wherein stabilizing comprises selectively deploying at least one side load applicator between the first work element and a facing wall of the vascular structure.

* * * * *